(12) United States Patent
So

(10) Patent No.: US 9,422,602 B2
(45) Date of Patent: Aug. 23, 2016

(54) METHODS AND COMPOSITIONS FOR DETERMINING NUCLEIC ACID DEGRADATION

(71) Applicant: Bio-Rad Laboratories, Inc., Hercules, CA (US)

(72) Inventor: Austin So, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 355 days.

(21) Appl. No.: 13/968,365

(22) Filed: Aug. 15, 2013

(65) Prior Publication Data

US 2014/0051595 A1  Feb. 20, 2014

Related U.S. Application Data

(60) Provisional application No. 61/683,672, filed on Aug. 15, 2012.

(51) Int. Cl.
*C12Q 1/68* (2006.01)

(52) U.S. Cl.
CPC ........... *C12Q 1/6851* (2013.01); *C12Q 1/6802* (2013.01); *C12Q 1/6876* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 4,988,617 A | 1/1991 | Landegren et al. | |
| 5,234,809 A | 8/1993 | Boom et al. | |
| 5,242,794 A | 9/1993 | Whiteley et al. | |
| 5,299,491 A | 4/1994 | Kawada et al. | |
| 5,403,711 A | 4/1995 | Walder et al. | |
| 5,494,810 A | 2/1996 | Barany et al. | |
| 5,597,713 A | 1/1997 | Kato et al. | |
| 5,641,658 A | 6/1997 | Adams et al. | |
| 5,705,628 A | 1/1998 | Hawkins | |
| 5,962,272 A | 10/1999 | Chenchik et al. | |
| 6,022,715 A * | 2/2000 | Merenkova | C12N 15/1096 435/6.16 |
| 6,251,247 B1 | 6/2001 | Mitsuhashi et al. | |
| 6,262,490 B1 | 7/2001 | Hsu et al. | |
| 6,582,938 B1 | 6/2003 | Su et al. | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 7,001,724 B1 | 2/2006 | Greenfield | |
| 7,041,481 B2 | 5/2006 | Anderson et al. | |
| 7,270,958 B2 | 9/2007 | Makarov et al. | |
| 7,622,280 B2 | 11/2009 | Holliger et al. | |
| 7,645,581 B2 | 1/2010 | Knapp et al. | |
| 8,399,198 B2 | 3/2013 | Hiddessen et al. | |
| 2006/0063170 A1* | 3/2006 | Erlander | C12Q 1/68 435/6.14 |
| 2006/0257866 A1 | 11/2006 | Welch et al. | |
| 2007/0259340 A1 | 11/2007 | Schramm | |
| 2007/0281336 A1 | 12/2007 | Jendrisak et al. | |
| 2008/0318801 A1* | 12/2008 | Leung | C12Q 1/6844 506/9 |
| 2009/0053719 A1* | 2/2009 | Lo | C12Q 1/6851 435/6.11 |
| 2010/0035249 A1 | 2/2010 | Hayashizaki et al. | |
| 2010/0057371 A1 | 3/2010 | Denisov | |
| 2010/0092973 A1* | 4/2010 | Davies | B01L 3/502784 435/6.19 |
| 2010/0173394 A1 | 7/2010 | Colston, Jr. et al. | |
| 2011/0053798 A1 | 3/2011 | Hindson et al. | |
| 2011/0086780 A1 | 4/2011 | Colston, Jr. et al. | |
| 2011/0092373 A1 | 4/2011 | Colston, Jr. et al. | |
| 2011/0092376 A1 | 4/2011 | Colston, Jr. et al. | |
| 2011/0092392 A1 | 4/2011 | Colston, Jr. et al. | |
| 2011/0104785 A1* | 5/2011 | Vaidyanathan | C12N 15/10 435/196 |
| 2011/0217712 A1 | 9/2011 | Hiddessen et al. | |
| 2011/0244455 A1* | 10/2011 | Larson | C12Q 1/686 435/6.11 |
| 2011/0311978 A1 | 12/2011 | Makarewicz, Jr. et al. | |
| 2012/0021423 A1 | 1/2012 | Colston, Jr. et al. | |
| 2012/0322058 A1* | 12/2012 | Regan | C12Q 1/683 435/6.11 |
| 2013/0309680 A1* | 11/2013 | Morley | C12Q 1/6851 435/6.12 |

FOREIGN PATENT DOCUMENTS

| | | |
|---|---|---|
| WO | WO 00/18957 A1 | 4/2000 |
| WO | WO 01/04286 A1 | 1/2001 |
| WO | WO 03/048387 A1 | 6/2003 |
| WO | WO 2007/117039 A1 | 10/2007 |
| WO | WO 2010/036352 A1 | 4/2010 |
| WO | WO 2011/008990 A1 | 1/2011 |

(Continued)

OTHER PUBLICATIONS

Blewett et al. (A quantitative assay for measuring mRNA decapping by splinted ligation reverse transcription polymerase chain reaction: qSL-RT-PCR, RNA. Mar. 2011;17(3):535-43. doi: 10.1261/rna.2436411. Epub Jan. 10, 2011).*

(Continued)

*Primary Examiner* — Aaron Priest
(74) *Attorney, Agent, or Firm* — Kolisch Hartwell, P.C.

(57) ABSTRACT

Described herein are methods, systems, compositions and kits to enable determination of a level of degradation of nucleic acids in a sample. For example, the determination of the amount of degradation of RNA in a sample can be accomplished by labeling one or both of the intact 5'- and/or 3'-ends of an mRNA molecule by taking advantage of the unique diol moiety present at these structures. Labeled nucleotides can then be partitioned into droplets and the amount of degradation can be determined by detecting label present in the partitions and making quantitative or qualitative comparisons with a reference sample. In some cases, the degree of degradation is also determined by factoring in the total concentration or quantity of RNA in the sample.

18 Claims, 16 Drawing Sheets

(56) References Cited

FOREIGN PATENT DOCUMENTS

| WO | WO 2011/050069 A1 | 4/2011 |
|---|---|---|
| WO | WO 2011/088149 A2 | 7/2011 |
| WO | WO 2011/156434 A2 | 12/2011 |

OTHER PUBLICATIONS

Lau et al. (An Abundant Class of Tiny RNAs with Probable Regulatory Roles in Caenorhabditis elegans, Science. Oct. 26, 2001;294(5543):858-62).*
Bartel Lab Protocol (hereinafter "Bartel"; attached, Jul. 31, 2005).*
Die et al. (Characterization of the 3':5' ratio for reliable determination of RNA quality, Anal Biochem. Dec. 15, 2011;419(2):336-8. Epub Aug. 16, 2011).*
Vermeulen et al. (Measurable impact of RNA quality on gene expression results from quantitative PCR, Nucleic Acids Res. May 2011;39(9):e63. Epub Feb. 11, 2011).*
Clontech (RNA/cDNA Quality Assay User Manual, attached, Jan. 19, 2011).*
Sigma-Aldrich (the 3'/5' Assay for Analysis of RNA Integrity Protocol, available at http://www.sigmaaldrich.com/technical-documents/protocols/biology/3-5-assay-for-analysis-of-rna-integrity.html, accessed Jan. 30, 2016).*
Mullen et al. (Degradation of histone mRNA requires oligouridylation followed by decapping and simultaneous degradation of the mRNA both 5' to 3' and 3' to 5', Genes Dev. Jan. 1, 2008; 22(1):50-65).*
Couttet et al. (Messenger RNA deadenylylation precedes decapping in mammalian cells, Proc Natl Acad Sci U S A. May 27, 1997; 94(11):5628-5633).*
Takano et al. (A multiplex endpoint RT-PCR assay for quality assessment of RNA extracted from formalin-fixed paraffin-embedded tissues, BMC Biotechnol. Dec. 17, 2010;10:89. doi: 10.1186/1472-6750-10-89).*
Blum et al. (Polyadenylation Promotes Degradation of 3*-Structured RNA by the *Escherichia coli* mRNA Degradosome in Vitro, J Biol Chem. Feb. 12, 1999;274(7):4009-16).*
Promega (Methods of RNA Quality Assessment, attached, Oct. 31, 2012).*
Adessi, et al. Solid phase DNA amplification: characterisation of primer attachment and amplification mechanisms. Nucleic Acids Res. Oct. 15, 2000;28(20):E87.
Banerjee. 5'-terminal cap structure in eucaryotic messenger ribonucleic acids. Microbiol Rev. Jun. 1980;44(2):175-205.
Bisaillon, et al. Viral and cellular enzymes involved in synthesis of mRNA cap structure. Virology. Sep. 15, 1997;236(1):1-7.
Brouzes, et al. Droplet microfluidic technology for single-cell high-throughput screening Proc Natl Acad Sci U S A. Aug. 25, 2009;106(34):14195-200.
Czworkowski, et al. Fluorescence study of the topology of messenger RNA bound to the 30S ribosomal subunit of *Escherichia coli*. Biochemistry. May 14, 1991;30(19):4821-30.
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Fahy, et al. Self-sustained sequence replication (3SR): an isothermal transcription-based amplification system alternative to PCR. PCR Methods Appl. Aug. 1991;1(1):25-33.
Fromont-Racine, et al. A highly sensitive method for mapping the 5' termini of mRNAs. Nucleic Acids Res. Apr. 11, 1993;21(7):1683-4.

Hansske, et al. Modification of the 3' terminus of tRNA by periodate oxidation and subsequent reaction with hydrazides. Methods Enzymol. 1979;59:172-81.
Harbers. Addressing mRNA Complexity: Utilizing the 5' Cap Structure of mRNA for Transcriptome Analysis. DNAform precision gene technologies. Presentation at Brown University on Apr. 18, 2011.
Hileman, et al. Synthesis and characterization of conjugates formed between periodate-oxidized ribonucleotides and amine-containing fluorophores. Bioconjug Chem. Sep.-Oct. 1994;5(5):436-44.
Joo, et al. Advances in single-molecule fluorescence methods for molecular biology. Annu Rev Biochem. 2008;77:51-76. doi: 10.1146/annurev.biochem.77.070606.101543.
Leamon, et al. A massively parallel PicoTiterPlate based platform for discrete picoliter-scale polymerase chain reactions. Electrophoresis. Nov. 2003;24(21):3769-77.
Lizardi, et al. Mutation detection and single-molecule counting using isothermal rolling-circle amplification. Nat Genet. Jul. 1998;19(3):225-32.
Maruyama, et al. Oligo-capping: a simple method to replace the cap structure of eukaryotic mRNAs with oligoribonucleotides. Gene. Jan. 28, 1994;138(1-2):171-4.
Mitra, et al. In situ localized amplification and contact replication of many individual DNA molecules. Nucleic Acids Res. Dec. 15, 1999;27(24):e34.
Nicolaou, et al. An expedient procedure for the oxidative cleavage of olefinic bonds with PhI(OAc)2, NMO, and catalytic OsO4. Org Lett. Apr. 2, 2010;12(7):1552-5. doi: 10.1021/o1100290a.
Ochman, et al. Genetic applications of an inverse polymerase chain reaction. Genetics. Nov. 1988;120(3):621-3.
Odom, et al. Distances between 3' ends of ribosomal ribonucleic acids reassembled into *Escherichia coli* ribosomes. Biochemistry. Dec. 23, 1980;19(26):5947-54.
Pierce, et al. Linear-after-the-exponential polymerase chain reaction and allied technologies. Real-time detection strategies for rapid, reliable diagnosis from single cells. Methods Mol Med. 2007;132:65-85.
Proudnikov, et al. Chemical methods of DNA and RNA fluorescent labeling. Nucleic Acids Res. Nov. 15, 1996;24(22):4535-42.
Saiki, et al. Analysis of enzymatically amplified beta-globin and HLA-DQ alpha DNA with allele-specific oligonucleotide probes. Nature. Nov. 13-19, 1986;324(6093):163-6.
Shuman. Capping enzyme in eukaryotic mRNA synthesis. Prog Nucleic Acid Res Mol Biol. 1995;50:101-29.
Shuman. Structure, mechanism, and evolution of the mRNA capping apparatus. Prog Nucleic Acid Res Mol Biol. 2001;66:1-40.
Stemmer, et al. Single-step assembly of a gene and entire plasmid from large numbers of oligodeoxyribonucleotides. Gene. Oct. 16, 1995;164(1):49-53.
Suzuki, et al. Construction and characterization of a full length-enriched and a 5'-end-enriched cDNA library. Gene. Oct. 24, 1997;200(1-2):149-56.
Suzuki, et al. Construction of full-length-enriched cDNA libraries. The oligo-capping method. Methods Mol Biol. 2001;175:143-53.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995;23(21):4407-14.
Walker, et al. Strand displacement amplification—an isothermal, in vitro DNA amplification technique. Nucleic Acids Res. Apr. 11, 1992;20(7):1691-6.
Westin, et al. Anchored multiplex amplification on a microelectronic chip array. Nat Biotechnol. Feb. 2000;18(2):199-204.
Wu, et al. A fluorescence-labeling method for sequencing small RNA on polyacrylamide gel. Nucleic Acids Res. Sep. 1, 1996;24(17):3472-3.

* cited by examiner

Figure 11
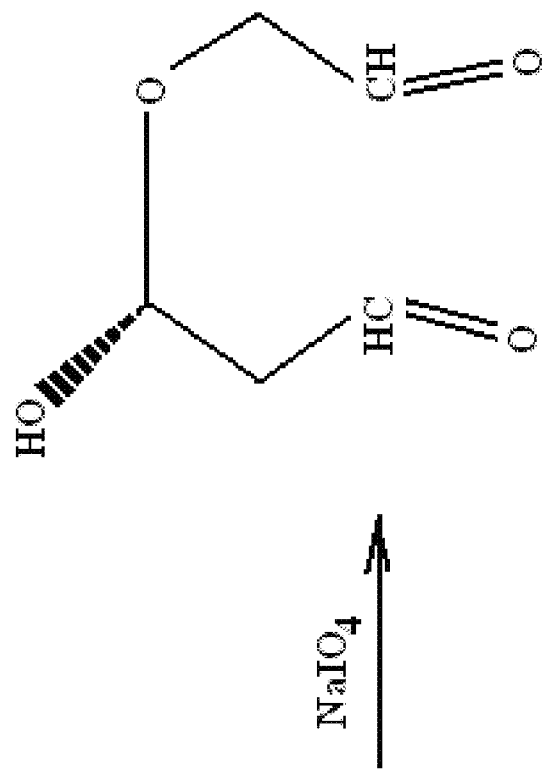
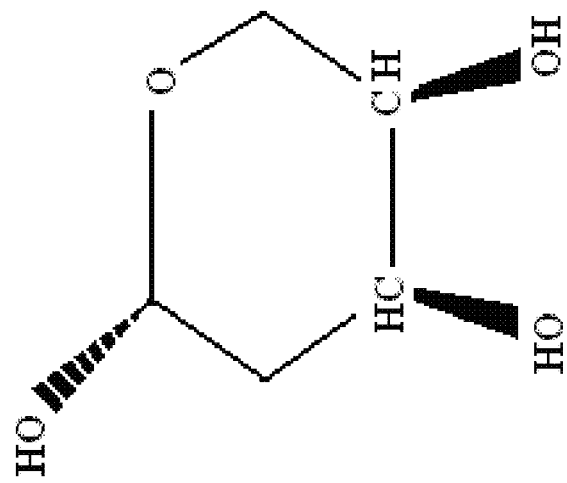

Figure 15
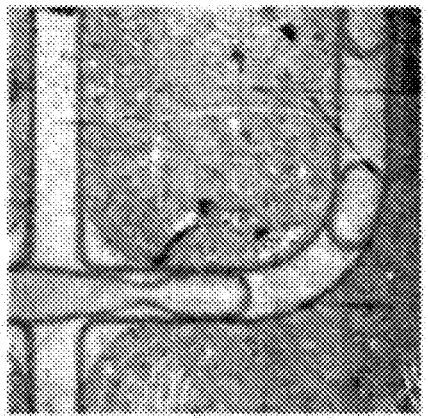
A
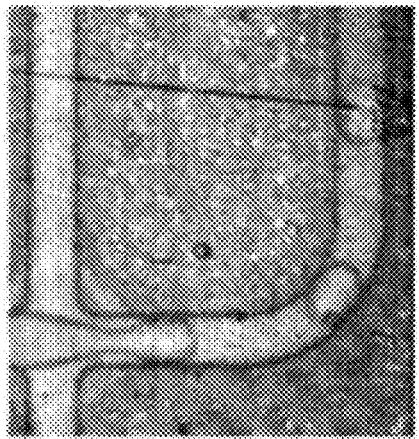
B

METHODS AND COMPOSITIONS FOR DETERMINING NUCLEIC ACID DEGRADATION

CROSS-REFERENCE

This application claims the benefit of U.S. Provisional Application No. 61/683,672, filed Aug. 15, 2012, which is hereby incorporated by reference in its entirety

BACKGROUND

Ribonucleic acid (RNA) molecules are chains of nucleotides, each nucleotide containing a ribose, a nucleoside base, and a phosphate group. Messenger RNA (mRNA) plays a central role in the coding of genetic information and in converting the genetic code into proteins that carry out essential cellular functions. Thus, assays for the analysis of RNA molecules within cell or tissue samples are widely used by biologists to understand the molecular underpinnings of life. One of the challenges of these assays is the relative instability of RNA molecules leading to degradation. Assays to determine the quality of RNA samples can depend on a ratiometric determination of 28S to 18S RNA—however, such determinations only provide an approximation of RNA degradation status. Methods that provide accurate measurements of RNA degradation in a sample would be useful for a wide range of clinical and research applications.

Accurate measures of data obtained from mRNA, such as gene expression, depend on the state of the mRNA sample being qualified. Generally, the degradation state of an mRNA population can be assessed by using a single mRNA species as a surrogate molecule. Using two Taqman assays designed to target this mRNA at the 3'- and the 5'-end of the molecule, the mRNA population can be converted to cDNA either through random priming or oligo(dT) priming and the cDNA population can be interrogated simultaneously with these two assay. The linked:unlinked ratio between the two assays can then be used to provide an index of degradation state. The reliability of this assay however, depends on the processivity of the reverse transcriptase utilized, which can convolute any indices of degradation state.

SUMMARY

In an aspect, a method of detecting degradation of a nucleic acid comprises contacting a sample comprising a nucleic acid with at least one agent that is capable of facilitating labeling an end of the nucleic acid, wherein the nucleic acid has a first end with a first end structure and a second end with a second end structure; labeling the first and/or second end structures with one or more labels; separating the sample contacted with the agent into a plurality of spatially isolated partitions; enumerating a number of spatially isolated partitions comprising the first or the second label; and determining an amount of degradation for the nucleic acid based on the enumerating. In some embodiments, the first end is a 5'-end, the second end is a 3'-end, or the first end is a 5'-end and the second end is a 3'-end. In some embodiments, the first end structure is intact, modified, or blocked. In some embodiments, the second end structure is intact, modified, or blocked. In some embodiments, the at least one agent that is capable of facilitating labeling an end of the nucleic acid comprises an enzyme, a compound, or a combination thereof. In some embodiments, a first agent of the at least one agents facilitates the labeling of the first end of the nucleic acid and a second agent of the at least one agents facilitates the labeling of the second end of the nucleic acid. In some embodiments, the one or more labels comprise a detectable signal, a nucleotide, a polypeptide, or a combination thereof. In some embodiments, one of the one or more labels is capable of labeling the first end and the second end of the nucleic acid. In some embodiments, at least one of the one or more labels is capable of labeling the first end but not the second end, at least one of the one or more labels is capable of labeling the second end but not the first end, or a combination thereof. In some embodiments, the one or more labels comprise a first label specific to the first end structure, a second label specific to the second end structure, or a combination thereof. In some embodiments, the nucleic acids comprise fully degraded nucleic acids, partially degraded nucleic acids, substantially not degraded nucleic acids, and combinations thereof. In some embodiments, the separating is randomized. In some embodiments, the separating is independent of the size of the nucleic acid. In some embodiments, the spatially isolated partitions are droplets within an emulsion. In some embodiments, the nucleic acid is RNA. In some embodiments, the nucleic acid is mRNA. In some embodiments, the nucleic acids are present at an average concentration of less than about five molecules per partition. In some embodiments, the nucleic acids are present at an average concentration of from 0 to 2 molecules per partition.

In some embodiments, the first end structure is intact, modified, or blocked and the second end structure is intact, modified, or blocked. In some embodiments, the first end structure is intact and the second end structure is intact. In some embodiments, the first end structure is modified and the second end structure is intact, modified, or blocked. In some embodiments, the first end structure comprises an intact 5'-cap. In some embodiments, the first end structure comprises a 7-methylguanosine nucleotide. In some embodiments, the second end structure comprises an intact 3'-poly (A) tail. In some embodiments, the first end structure comprises a diol. In some embodiments, the second end structure comprises a diol. In some embodiments, the first end structure and the second end structure comprise a diol. In some embodiments, the first end structure comprises a 5'-end phosphate group. In some embodiments, the first end structure and/or second end structure comprises a 5'-phosphate, a 2'-phosphate, a 3'-phosphate or a 2'-3'-linked phosphate group. In some embodiments, any first or second ends with 5'-phosphate, 2'-phosphate, 3'-phosphate or 2'-3'-linked phosphate groups remain substantially unlabeled with the one or more labels. In some embodiments, the first end structure and/or second end structure comprises an oxidized diol. In some embodiments, the first end structure and/or second end structure comprises an oxidized ribose diol. In some embodiments, the first end structure and/or second end structure comprises an amine group. In some embodiments, the first end structure and/or second end structure comprises an oligonucleotide In some embodiments, the at least one agent is an enzyme. In some embodiments, the at least one agent comprises a ligase. In some embodiments, the at least one agent comprises an RNA ligase. In some embodiments, the at least one agent comprises a T4 RNA ligase. In some embodiments, the at least one agent comprises a kinase. In some embodiments, the at least one agent comprises a polynucleotide kinase. In some embodiments, the at least one agent comprises a T4 polynucleotide kinase. In some embodiments, the at least one agent comprises a phosphatase. In some embodiments, the at least one agent comprises a pyrophosphatase. In some embodiments, the at least one agent comprises a Tobacco Acid Pyrophosphatase (TAP). In some embodiments, the at least one agent comprises an alkaline phosphatase (AP) or calf intestinal phosphatase (CIP). In some embodiments, the at least one agent comprises a decapping enzyme. In some embodiments, the at least one agent comprises a yeast decapping enzyme, mammalian decapping enzyme, *Arabidopsis thaliana* decapping enzyme, or vaccinia virus decapping enzyme. In some embodiments, the at least one agent comprises a ribonuclease. In some embodiments, the at least one agent comprises an exoribonuclease. In some embodiments, the at least one agent comprises a 5'-exoribonuclease. In some embodiments, the at least one agent comprises Dcp2, Dcp1, or a combination thereof. In some embodiments, the at least one agent hydrolyzes a phosphoric acid anhydride bond in a triphosphate bridge of a 5'-cap of the nucleic acid. In some embodiments, the at least one agent causes formation of a 5'-monophosphate group. In some embodiments, the at least one agent targets a product, or modified product, of a reaction catalyzed by a capping enzyme. In some embodiments, the at least one agent targets a product, or modified product, of a reaction catalyzed by an RNA triphosphatase, an RNA guanylyltransferase, an RNA (guanine N7) methyltransferase, or a combination thereof. In some embodiments, the at least one agent causes formation of an aldehyde on the nucleic acid. In some embodiments, the at least one agent causes formation of a dialdehyde on the nucleic acid. In some embodiments, the dialdehyde is a 2',3'-dialdehyde. In some embodiments, the at least one agent comprises an oxidation agent. In some embodiments, the oxidation agent oxidizes a diol group. In some embodiments, the oxidizing agent targets ribose diols. In some embodiments, the oxidizing agent facilitates oxidization of the ribose diol groups to aldehydes. In some embodiments, the aldehydes facilitate the labeling of the first end and/or second end. In some embodiments, the oxidation agent does not oxidize a 2'-linked phosphate group, 3'-linked phosphate group, or a 2'-3'-linked phosphate group. In some embodiments, the oxidation agent oxidizes a diol group and does not oxidize a 2'-linked phosphate group, 3'-linked phosphate group, or a 2'-3'-linked phosphate group. In some embodiments, the oxidation agent comprises periodate, lead tetraacetate, $PhI(OAc)_2$, or a combination thereof.

In some embodiments, the labeling is covalent. In some embodiments, the labeling is non-covalent. In some embodiments, the labeling forms a hydrogen bond, an ionic bond, a bond held together by van der Waals forces, a hydrophobic bond, or a combination thereof. In some embodiments, the labeling forms an oligonucleotide comprising a double stranded region. In some embodiments, the labeling is not sequence specific. In some embodiments, the labeling is sequence specific. In some embodiments, the first end is degraded, the second end is degraded, or both the first end and the second end are degraded. In some embodiments, the first label and/or the second label do not target the degraded first end or the degraded second end. In some embodiments, the one or more labels is one label. In some embodiments, the one or more labels comprise at least two different labels. In some embodiments, the one or more labels comprise a fluorescent molecule. In some embodiments, the labeling comprises a hydrazine linkage. In some embodiments, the one or more labels comprise an oligonucleotide. In some embodiments, the oligonucleotide comprises a 5'-adenylated end. In some embodiments, the oligonucleotide comprises a 5'-adenylated end that is blocked at the 3'-end. In some embodiments, the oligonucleotide comprises a 5'-adenylated end that is blocked at the 3'-end and a target sequence for an amplification reaction. In some embodiments, the one or more labels comprise an antibody to the first end structure, an antibody to the second end structure, or both. In some embodiments, the antibody comprises a dye or reporter molecule. In some embodiments, the antibody comprises an anti-7-methylguanosine antibody. In some embodiments, the antibody comprises an anti-tri-methyl guanosine cap (3mG Cap) antibody.

In some embodiments, the method further comprises amplifying the first label, the second label, or both.

In some embodiments, the nucleic acids or fragments thereof, comprise identical sequences. In some embodiments, the nucleic acids have different sequences. In some embodiments, the nucleic acid is correlated with a disease or disorder.

In some embodiments, the method further comprises enumerating the number of spatially isolated partitions comprising a nucleic acid from a reference sample. In some embodiments, the nucleic acid from the reference sample is present at a known concentration. In some embodiments, the nucleic acid from the reference sample comprises a known concentration of fully degraded nucleic acids. In some embodiments, the nucleic acid from the reference sample comprises a known concentration of partially degraded nucleic acids. In some embodiments, the nucleic acid from the reference sample comprises a known concentration of substantially not degraded nucleic acids. In some embodiments, determining an amount of degradation for the nucleic acid based on the enumerating comprises comparing the number of spatially isolated partitions comprising the first and/or the second label to the number of spatially isolated partitions comprising the first or the second label from the reference sample. In some embodiments, a control agent reaction is performed to measure the efficiency of modification of the nucleic acid by the at least one agent. In some embodiments, a control labeling reaction is performed to measure the efficiency of labeling of the nucleic acid by the one or more labels.

In some embodiments, a percentage of the nucleic acids that are degraded in the sample is determined. In some embodiments, the nucleic acids that are degraded are fully degraded nucleic acids. In some embodiments, the nucleic acids that are degraded are partially degraded nucleic acids. In some embodiments, a percentage of the nucleic acids that are substantially not degraded in the sample is determined. In some embodiments, a percentage of the nucleic acids that are labeled with one of the one or more labels is determined. In some embodiments, a percentage of the nucleic acids that are labeled with a first label of the one or more labels is determined, and a percentage of nucleic acids that are labeled with a second label of the one or more labels is determined. In some embodiments, a percentage of nucleic acids that are labeled with a first label of the one or more labels and a second label of the one or more labels is determined. In some embodiments, the nucleic acids that are labeled with one of the one or more labels are substantially not degraded nucleic acids, partially degraded nucleic acids, or a combination thereof. In some embodiments, the nucleic acids that are labeled with a first label of the one or more labels are substantially not degraded nucleic acids, partially degraded nucleic acids, or a combination thereof, and wherein the nucleic acids that are labeled with a second label of the one or more labels are substantially not degraded nucleic acids, partially degraded nucleic acids, or a combination thereof. In some embodiments, the nucleic acids that are labeled with a first label of the one or more labels and a second label of the one or more labels are substantially not degraded nucleic acids.

In some embodiments, any of the first ends or second ends with 5'-phosphate, 2'-phosphate, 3'-phosphate or 2'-3'-linked phosphate groups remain substantially unlabeled with one or more labels. In some embodiments, any of the first ends or second end with ribose diol groups are substantially labeled with the one or more labels. In some embodiments, the method does not comprise converting mRNA to cDNA. In some embodiments, mRNA is not converted to cDNA.

In some embodiments, the determining the amount of degradation for the nucleic acid comprises: enumerating a number of spatially isolated partitions comprising only one label; enumerating a number of spatially isolated partitions comprising two labels; and comparing the number of spatially isolated partitions comprising two labels, and the number of spatially isolated partitions comprising only one label. In some embodiments, the determining is accomplished using an algorithm. In some embodiments, the method further comprises determining the concentration of the nucleic acid in the sample.

In some embodiments, the nucleic acid is obtained from a source selected from the group consisting of a serum sample, a plasma sample, a cell sample, a tissue sample, an organ sample, a cultured cell line, a biopsy sample, and a fluid sample containing a cell. In some embodiments, the nucleic acid is obtained from a source selected from the group consisting of a plant sample, an animal sample, a fungi sample, a protest sample, a moneran sample, a virus sample, a mitochondrial sample, and a chloroplast sample. In some embodiments, the nucleic acid is obtained from a human.

In some embodiments, the labeling of the first and second end structures with one or more labels comprises labeling the first end structure with a first label specific to the first end structure and the second end with a second label specific to the second end structure. In some embodiments, the amplification reaction is ddPCR.

In some embodiments, each of the one or more labels are different. In some embodiments, the sample is divided into two or more subsamples. In some embodiments, the amounts of degradation for the nucleic acid of the two or more subsamples are compared. In some embodiments, a linkage between the amounts of degradation for the nucleic acid of the two or more subsamples is determined.

In some aspects, a kit comprises at least one agent that is capable of facilitating labeling a ribose diol group at an end of a nucleic acid, a first labeling molecule, an enzyme that is capable of removing a 5'-end cap from an RNA, and an amine reactive label. In some aspects, a kit comprises an enzyme that is capable of removing a 5'-end cap from an RNA, an RNA ligase, a first oligonucleotide, wherein the oligonucleotide is blocked at the 3'-end and wherein the first oligonucleotide comprises a primer binding sequence, and an amine reactive label. In some aspects, a kit comprises at least one agent that is capable of facilitating labeling a ribose diol group at an end of a nucleic acid, a first labeling molecule, an enzyme that is capable of removing a 5'-end cap from an RNA, and an RNA ligase, and an oligonucleotide tag, wherein the oligonucleotide tag comprises a primer binding sequence. In some aspects, a kit comprises an enzyme that is capable of removing a 5'-end cap from an RNA, an RNA ligase, a first oligonucleotide, wherein the first oligonucleotide is blocked at the 3'-end and wherein the first oligonucleotide comprises a first primer binding sequence, and an oligonucleotide tag, wherein the oligonucleotide tag comprises a second primer binding sequence. In some embodiments, the amine reactive label comprises a fluorophore: In some embodiments, the first labeling molecule comprises a fluorophore. In some embodiments, the RNA ligase is T4 RNA ligase. In some embodiments, the kit further comprises an RNA dependent polymerase. In some embodiments, the kit further comprises a surfactant. In some embodiments, the kit further comprises a surfactant an oil In some embodiments, the kit further comprises instructions for performing a method for detecting degradation of a nucleic acid.

In some aspects, a plurality of droplets comprises nucleic acids, wherein the nucleic acids are selectively labeled such that non-degraded nucleic acids comprising a 5'-cap structure are selectively labeled with a first selected label. In some aspects, a plurality of droplets comprises nucleic acids, wherein the nucleic acids are conjugated to a label with selectivity, wherein the selectivity is towards non-degraded nucleic acid ends. In some embodiments, nucleic acids comprising 3'-ribose diols are selectively labeled with a second selected label.

In some embodiments, the selectivity is further towards non-degraded nucleic acids comprising 3'-ribose diols. In some embodiments, the selectivity is further towards non-degraded nucleic acids comprising 5'-caps.

In some aspects, the disclosure provides for a method of detecting degradation of a nucleic acid comprising contacting a sample comprising a nucleic acid with at least one agent that is capable of facilitating labeling an end of the nucleic acid, wherein the nucleic acid has a first end with a first end structure and a second end with a second end structure, labeling the first and second end structures with one or more labels, separating the sample contacted with the agent into a plurality of spatially isolated partitions, enumerating a number of spatially isolated partitions comprising the first or the second label, and determining an amount of degradation for the nucleic acid based on said enumerating. In some embodiments, the separating is randomized. In some embodiments, the separating is independent of the size of the nucleic acid. In some embodiments, the labeling is covalent. In some embodiments, the labeling is not sequence specific. In some embodiments, the one or more labels are capable of labeling either the first end or the second end of the nucleic acid. In some embodiments, the one or more labels comprise at least two different labels. In some embodiments, any first or second ends with 5' phosphate, 2' phosphate, 3' phosphate or 2'-3'-linked phosphate groups remain substantially unlabeled with one or more labels. In some embodiments, the at least one agent that is capable of facilitating labeling an end of the nucleic acid comprises an oxidizing agent. In some embodiments, the oxidizing agent targets ribose diols. In some embodiments, the oxidizing agent facilitates oxidization of the ribose diol groups to aldehydes. In some embodiments, the aldehydes facilitate the labeling of the ends. In some embodiments, the labeling comprises a hydrazine linkage. In some embodiments, any first or second end structures with ribose diol groups are substantially labeled with the one or more labels. In some embodiments, the nucleic acid comprises mRNA or cDNA. In some embodiments, the nucleic acid comprises mRNA. In some embodiments, the method does not comprise converting mRNA to cDNA. In some embodiments, the first end structure comprises a 5'-end cap. In some embodiments, the spatially isolated partitions are droplets within an emulsion. In some embodiments, the nucleic acid is present at an average concentration of not greater than about 5 copies per droplet. In some embodiments, the determining the amount of degradation for the nucleic acid comprises enumerating a number of spatially isolated partitions comprising only one label, enumerating a number of spatially isolated partitions comprising two labels; and comparing the number of spatially isolated partitions comprising two labels, and the number of spatially isolated partitions comprising only one label. In some embodiments, the determining is accomplished using an algorithm. In some embodiments, at least one of the one or more labels is a fluorescent label. In some embodiments, a first agent facilitates the labeling of a first end of the nucleic acid and a second agent facilitates the labeling of a second end of the nucleic acid. In some embodiments, the agent facilitates oxidization of ribose diol groups to aldehydes. In some embodiments, the nucleic acid is obtained from a source selected from the group consisting of a serum sample, a plasma sample, a cell sample, a tissue sample, an organ sample, a cultured cell line, a biopsy sample, and a fluid sample containing a cell. In some embodiments, the nucleic acid is obtained from a source selected from the group consisting of a plant sample, an animal sample, a fungi sample, a protest sample, a moneran sample, a virus sample, a mitochondrial sample, and a chloroplast sample. In some embodiments, the nucleic acid is obtained from a human. In some embodiments, the labeling of the first and second end structures with one or more labels comprises labeling the first end with a first label specific to the first end structure and the second end with a second label specific to the second end structure. In some embodiments, the at least one agent that is capable of facilitating an end of the nucleic acid comprises T4 ligase. In some embodiments, the method further comprises contacting the sample comprising the nucleic acid with a 5'-adenylated oligonucleotide that is blocked at the 3'-end. In some embodiments, the 5'-adenylated oligonucleotide that is blocked at the 3'-end comprises a target sequence for an amplification reaction. In some embodiments, the amplification reaction is ddPCR. In some embodiments, the first label and the second label are different.

In some aspects, the disclosure provides for a kit comprising at least one agent that is capable of facilitating labeling a ribose diol group at an end of a nucleic acid, a first labeling molecule, an enzyme that is capable of removing a 5'-end cap from an RNA, and an amine reactive label.

In some aspects, the disclosure provides for a kit comprising an enzyme that is capable of removing a 5'-end cap from an RNA, an RNA ligase, a first oligonucleotide, wherein the oligonucleotide is blocked at the 3'-end and wherein the first oligonucleotide comprises a primer binding sequence, and an amine reactive label.

In some aspects, the disclosure provides for a kit comprising at least one agent that is capable of facilitating labeling a ribose diol group at an end of a nucleic acid, a first labeling molecule, an enzyme that is capable of removing a 5'-end cap from an RNA, and an RNA ligase, and an oligonucleotide tag, wherein the oligonucleotide tag comprises a primer binding sequence.

In some aspects, the disclosure provides for a kit comprising an enzyme that is capable of removing a 5'-end cap from an RNA, an RNA ligase, a first oligonucleotide, wherein the first oligonucleotide is blocked at the 3'-end and wherein the first oligonucleotide comprises a first primer binding sequence, and an oligonucleotide tag, wherein the oligonucleotide tag comprises a second primer binding sequence.

In some embodiments, the amine reactive label comprises a fluorophore. In some embodiments, the first labeling molecule comprises a fluorophore. In some embodiments, the RNA ligase is T4 RNA ligase. In some embodiments, the kit further comprises an RNA dependent polymerase.

In some aspects, the disclosure provides for a plurality of droplets comprising nucleic acids, wherein the nucleic acids are selectively labeled such that non-degraded nucleic acids comprising a 5'-cap structure are selectively labeled with a first selected label. In some embodiments, nucleic acids comprising 3'-ribose diols are selectively labeled with a second selected label.

In some aspects, the disclosure provides for a plurality of droplets comprising nucleic acids, wherein the nucleic acids are conjugated to a label with selectivity, wherein the selectivity is towards non-degraded nucleic acid ends. In some embodiments, the selectivity is further towards non-degraded nucleic acids comprising 3'-ribose diols. In some embodiments, the selectivity is further towards non-degraded nucleic acids comprising 5'-caps.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11 depicts the oxidation of the diol moiety of an intact mRNA end to aldehydes using sodium periodate.

FIG. 15A displays droplet formation as a droplet is pinched by inflow of oil from the sides in a droplet generator.

FIG. 15B displays stretching/necking down as the droplet pulls away from the bulk fluid using a droplet generator.

DETAILED DESCRIPTION

General

Figure 1:
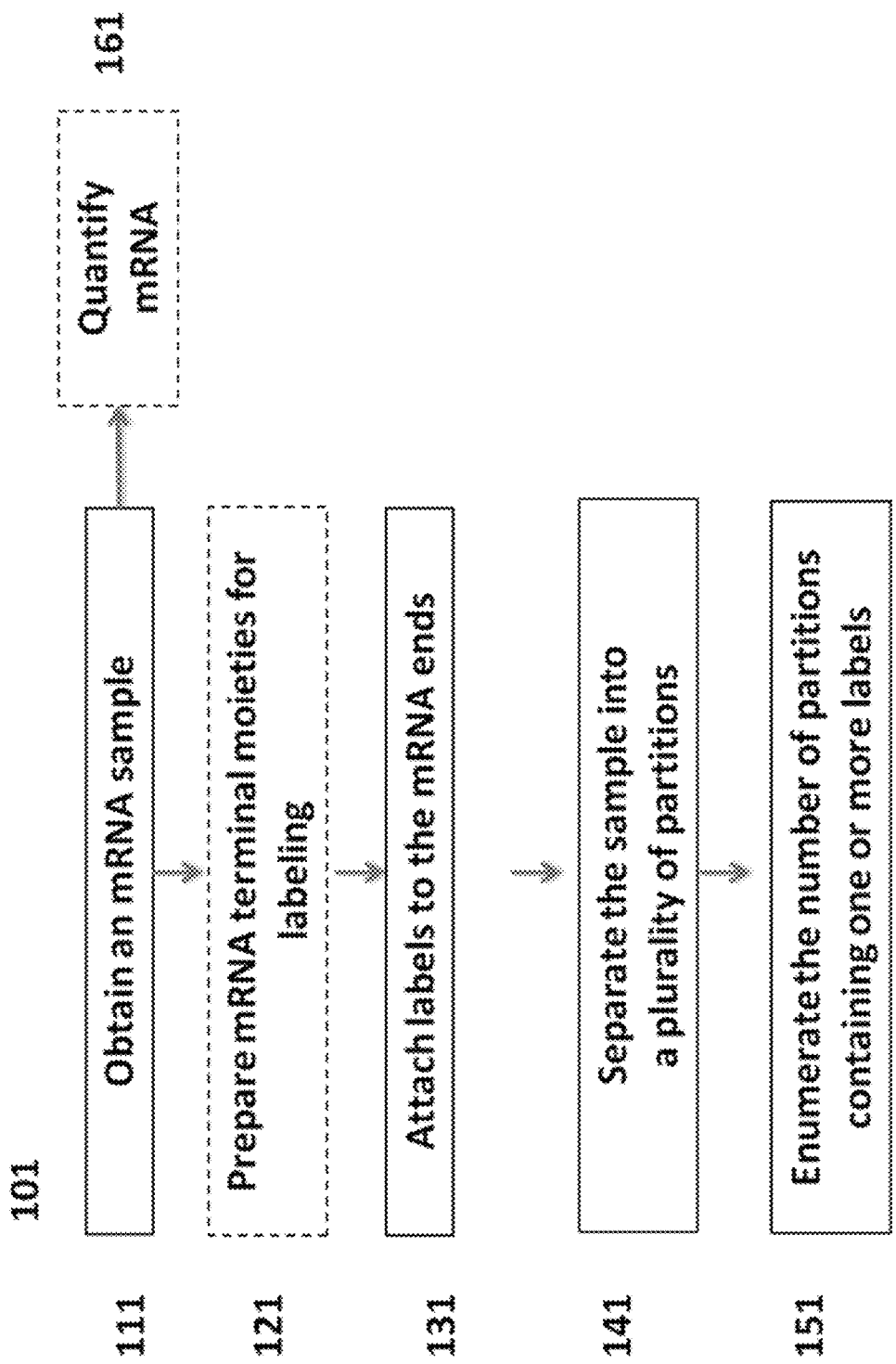
FIG. 1 illustrates a flowchart for the assessment of RNA degradation in a sample.

As used herein, the term "intact," when referring to an end of nucleotide, includes nucleotide end molecules with a diol moiety and includes nucleotide end molecules that had their diol moiety oxidized into aldehyde groups.

As used herein, the terms "derivative," and "modified" when referring to an end of nucleotide, include nucleotide end molecules, such as intact or other modified ends or derivatives, treated with an agent, such as a chemical or an enzyme, that no longer contain a diol, such as a ribose diol.

This disclosure provides methods, compositions and kits for detecting and evaluating various characteristics relating to nucleic acids. More particularly, it provides methods of detecting and evaluating nucleic acid degradation or fragmentation in a sample. Degradation can often be catalyzed by an enzyme, such as an RNAse. An enzyme can be an endogenous enzyme or an enzyme exogenously introduced, such as through a process of handling or manipulating a sample.

Methods, compositions, and kits described herein can improve reliability of accurate measures of data obtained from mRNA, such as gene expression data, by exploiting structural features of mRNA to assay its degradation state prior to analysis.

Substantially all non-degraded mRNA possess two common sites, a 3'-polyadenylated tail ("poly(A) tail") and a 5'-end cap sequence ("5'-cap"), each site comprising terminal riboses with diol moieties. Diol moieties of 5'- and/or 3'-ends can be oxidized to aldehydes and coupled to a reporter molecule, such as biotin or a fluorescent molecule, through a linkage, such as a hydrazine linkage. In some embodiments, a 5'-end and a 3'-end can be non-selectively labeled. In some embodiments, a 5'-end and a 3'-end can be selectively labeled. A reporter molecule can be a compound or set of compounds that reports a condition of something else, such as an extent of a reaction or efficiency of a reaction. Exemplary reporters comprise one or more labels dye, such as a fluorescent dye or an energy transfer pair, and/or one or more labels oligonucleotide.

In some embodiments, chemical groups associated with both ends of an mRNA molecule with intact 5'- and 3'-ends can be modified or labeled simultaneously and/or nonspecifically. In some embodiments, chemical groups associated with one end of an mRNA molecule with intact 5'- and 3'-ends can be excluded from modifying or labeling reactions, while another end is modified and/or labeled.

In some embodiments, various chemistries at 5'-ends of mRNA molecules can be available for modifying or labeling, while 3'-ends can be unavailable for modifying or labeling. For example, an intact 5'-end of mRNA molecule can be oxidized or labeled, while a 3'-poly(A) tail is specifically blocked from any oxidation or labeling. An intact 5'-end of an mRNA molecule can be oxidized or labeled, while a 3'-end is blocked from any oxidation or labeling, for example, because the 3'-end does not contain a terminal ribose comprising a diol moiety, such as due to the lack of an intact poly(A) tail comprising a terminal ribose comprising a diol moiety.

In some embodiments, various chemistries at 3'-ends of degraded mRNA molecules can be available for modifying or labeling, while their 5'-ends can be unavailable for modifying or labeling. For example, a 3'-end of an intact mRNA molecule can be oxidized or labeled, while a 5'-end cap structure is specifically blocked from any oxidation or labeling. As another example, a 3'-end of a cleaved or degraded mRNA molecule can be oxidized or labeled, while a 5'-end is blocked from any oxidation or labeling, for example, because the 5'-end does not contain a terminal ribose comprising a diol moiety, such as due to a lack of an intact 5'-cap structure comprising a terminal ribose comprising a diol moiety.

In some embodiments, an intact 5'-end cap can be removed chemically or enzymatically, leaving a 5'-end phosphate group. In some embodiments, an intact 5'-end cap can be removed specifically using a chemical or enzyme. The 3'-end diol can then be modified, such as oxidized, allowing selective labeling of a poly(A) tail with a unique label. Alternatively, a 5'-adenylated oligonucleotide that is blocked at a 3'-end (e.g., a ddA or a $NH_2$ blocking group) containing a target sequence for ddPCR can be introduced (e.g., via T4 RNA ligase). This method has been utilized for the purification and cloning of miRNAs. Subsequently, a 5'-end phosphate can be used as a site to introduce a second unique label (e,g., an amine reactive label via amine modification), or a second oligonucleotide tag containing a second target sequence (e.g., for ddPCR) can be introduced (e.g., using T4 RNA ligase).

An mRNA population can then partitioned into droplets and a linkage between these 2 assays can be assessed. If a modification is chemical, then they can be analyzed directly. If a modification contains assay sequences, ddPCR can be employed. As in the canonical milepost assay, if both assays are present in the same droplet, this can imply that there is little to no degradation of mRNA. If both assays are separated, then degradation may have occurred. Thus, fractional linkage can provide an index of mRNA degradation state.

Many of the methods provided herein can further comprise comparing nucleic acids within a test sample with those within a reference sample. A reference sample can be, for example, a sample with a known quantity of degraded nucleotides, a sample that substantially contains no degraded nucleotides, or a sample with essentially no non-degraded nucleotides. A method can also involve use of an algorithm or measure of probability in order to compare a test sample with results that would be predicted for a particular level of degradation.

A method can further comprise a reference step that involves contacting a reference sample with a known level of mRNA degradation with the same detectable labels. A method can further comprise partitioning a sample and/or a reference sample into a number of sample volumes or spatially isolated partitions and then detecting the detectable labels in the partitions. In some cases, a method further comprises enumerating a number of spatially isolated partitions comprising a first or a second label; and determining an amount of degradation for a mRNA based on the enumerating step. In many embodiments, droplet digital polymerase chain reaction (ddPCR) is used to partition and quantitate the sample nucleic acids (e.g., RNA).

Generally, a method can comprise evaluating a level of mRNA degradation in a sample by contacting a sample with the same detectable label or at least two different detectable labels that preferentially label mRNA molecules with an intact 5'- and/or 3'-end, or a derivative of an intact 5'- and/or 3'-end other than a degradation derivative. A label can be an identifying and/or distinguishing marker or identifier connected to or incorporated into any entity, such as a molecule, molecular complex, compound, biological particle, or droplet. The label can be described as labeling a particular entity to produce a labeled entity. A label can be, for example, a dye (e.g., fluorescent dye) that renders an entity optically detectable or more optically detectable, or otherwise enhances a signal generated by an entity. Exemplary dyes used for labeling are fluorescent dyes (fluorophores) and fluorescence quenchers. In some cases, labels comprise specific nucleic acid sequences.

One or more labels can be capable of selectively or non-selectively the ends of a nucleic acid (e.g., mRNA). One or more labels can be capable of labeling either a first end or a second end of a nucleic acid, or both ends. In an example of non-selective labeling, ends of nucleic acids can be randomly labeled with one or more labels. In some cases, any first or second end structures with ribose diol groups are substantially labeled with one or more labels. In other cases, a 5'-end or a 3'-end is selectively labeled with a detectable label. In some cases, an intact 5'-end or an intact 3'-end of a nucleic acid is selectively modified to allow particular labeling of that modified end, thereby facilitating selective end-labeling. In some cases, a 5'-end or a 3'-end of a nucleic acid is manipulated to preclude labeling of that particular end, thereby facilitating selective end-labeling The methods provided herein can also comprising detecting or determining a concentration of a nucleic acid in a sample, and possibly using that measure to also aid a determination of a degree of degradation of nucleic acids in a sample. Concentration is generally a measure of a quantity or amount of nucleotides (e.g. relative to a solvent, such as water) in a sample. If a concentration is low, a test may not have enough nucleotides to detect or obtain any measurement. Methods can further comprise evaluating the quality of a nucleic acid in a sample. The quality of a nucleotide can relate to whether a nucleotide has been contaminated with other types of molecules or foreign nucleic acids from a different sample. For example, if a sample includes different types of molecules (e.g., other molecules that are the same size as the nucleotides of interest), a sample may not have good quality when one is only interested in one or a few of the nucleotides.

In some embodiments, methods can be used to analyze mRNA degradation caused by ribonucleases (RNAs). When RNA is cleaved or degraded, such as by RNAse enzymes, neither of the resulting degraded mRNA cleavage products can contain terminal ribose diol moieties on both the 3'- and 5'-ends. For example, a degraded mRNA molecule can contain a 3'-end with a 3'-terminal ribose comprising a diol moiety, such as an intact 3'-poly(A) tail, and not contain a 5'-end with a 5'-terminal ribose comprising a diol moiety, such as an intact 5'-end cap structure. As another example, a degraded mRNA molecule can contain a 5'-end with a terminal ribose comprising a diol moiety, such as an intact 5'-end cap structure, and not contain a 3'-end with a terminal ribose comprising a diol moiety, such as an intact 3'-poly(A) tail. As another example, a degraded mRNA molecule may not contain a 3'-end with a 3'-terminal ribose comprising a diol moiety and does not contain a 5'-end comprising a 5'-terminal ribose comprising a diol moiety.

Figure 12:
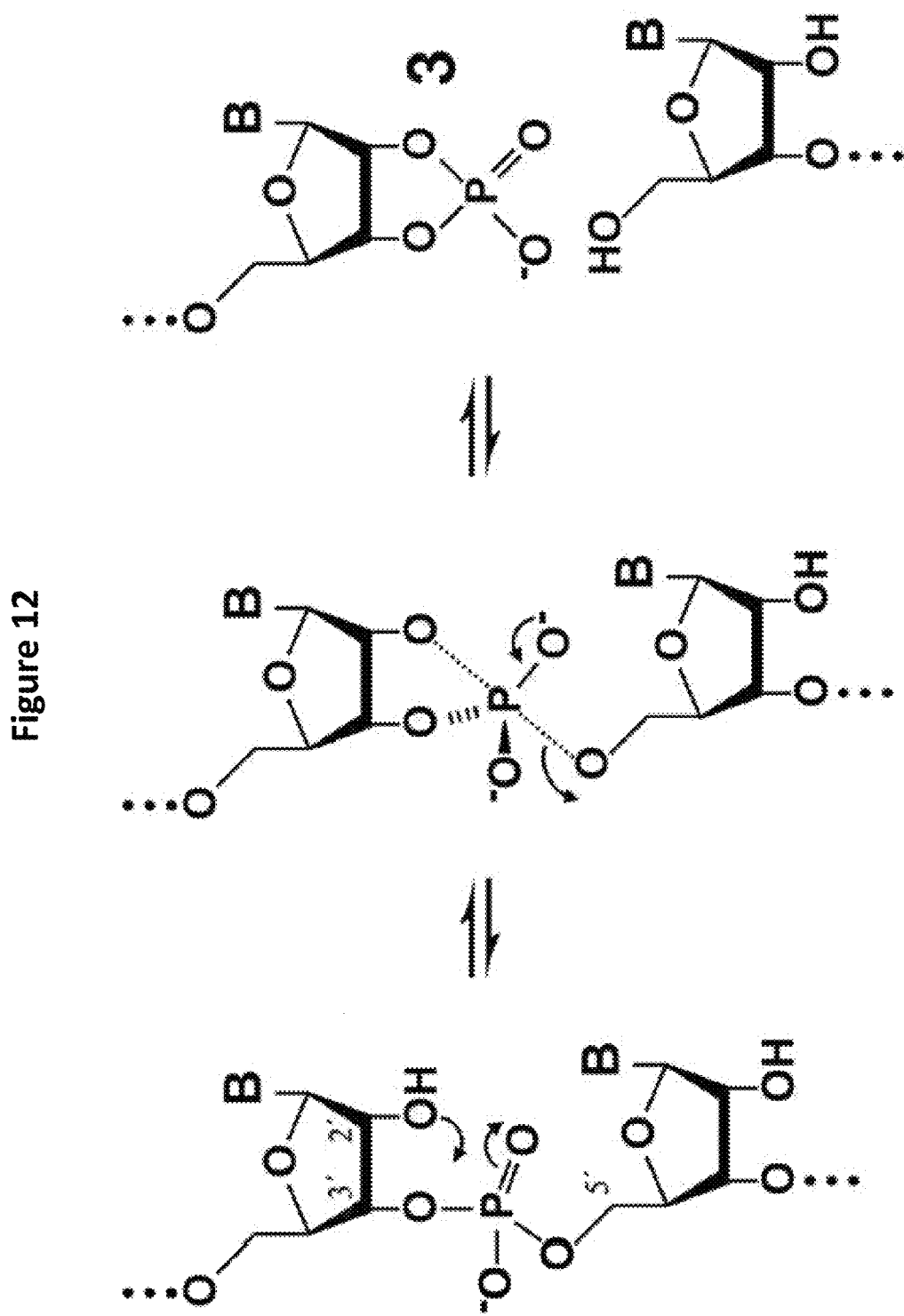
FIG. 12 depicts a mechanism of RNA degradation.
Figure 13:
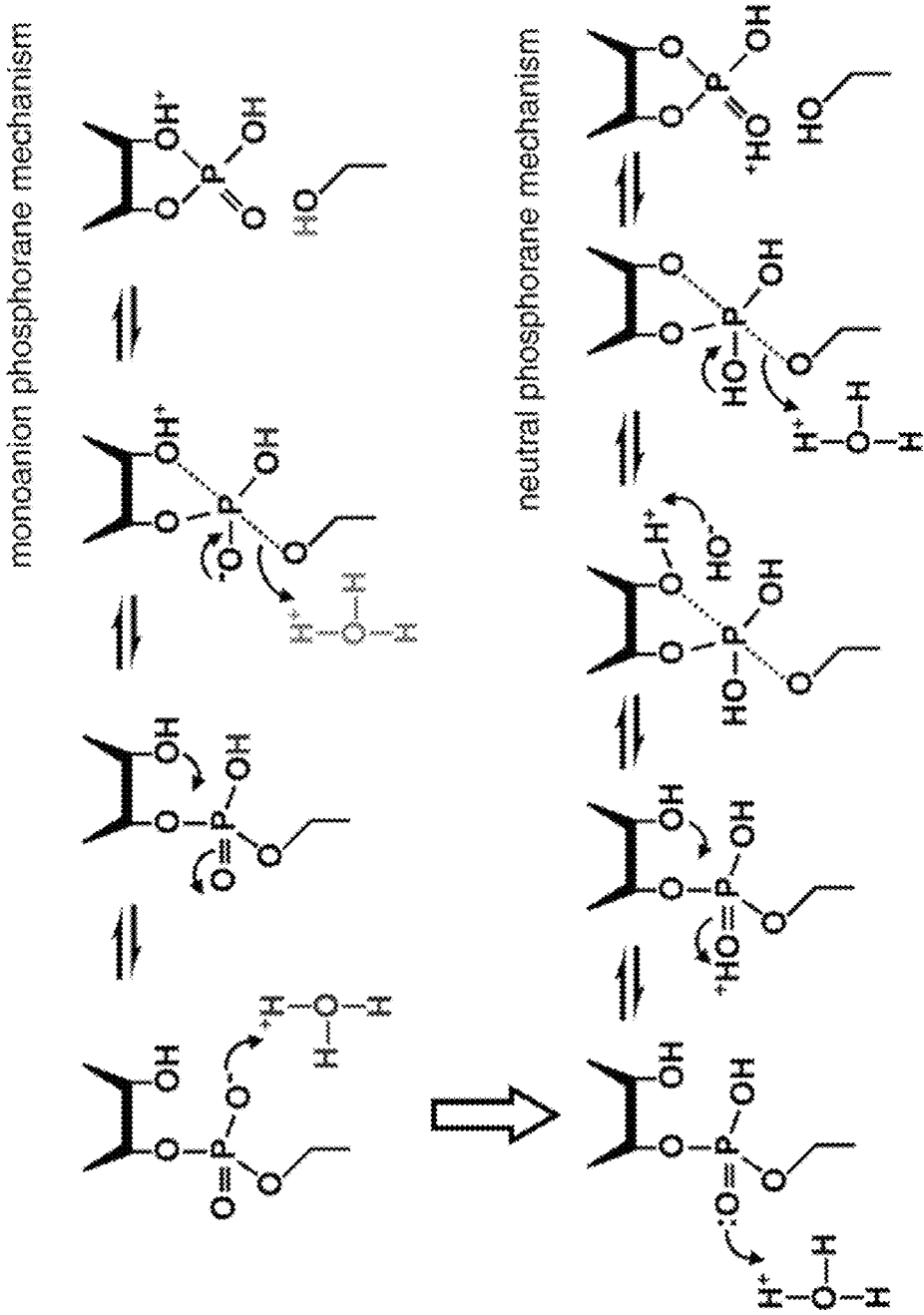
FIG. 13 depicts a mechanism of RNA degradation.

A non-limiting mechanism for RNA cleavage can involve internal phosphoester transfer, wherein a 2'-oxygen atom carries out an SN2-like nucleophilic attack on an adjacent phosphorus center (transesterification), such as catalyzed by ribonucleases, such as RNAses (FIGS. 12 and 13). This reaction can proceed when a 2'-oxygen atom in a ribose moiety of RNA adjacent to a given internucleotide linkage executes a nucleophilic attack on the phosphorus center of a 3'-phosphate group. Spontaneous cleavage of RNA typically occurs with a rate constant of ~$10^{-7}$ $min^{-1}$ (Li and Breaker 1999). In comparison, enzymes, such as RNAses, can accelerate this phosphoester transfer reaction by many orders of magnitude (Adams et al. 1992; Raines 1998).

The cleavage products created by this reaction can comprise a 3'-end comprising a ribose with a 2' phosphate linkage, 3'-phosphate linkage, or 2',3'-cyclic phosphate linkage. Such cleavage products do not contain a 3'-terminal ribose comprising a diol moiety. Thus, the 3'- or 2' hydroxyl groups of a cleavage product with a 3'-end containing a ribose with a 2' phosphate linkage or a 3'-phosphate linkage, are less likely to be oxidized to aldehydes and thus less likely to be capable of being labeled using any of the labels described herein. The 3'-end of a cleavage product comprising a 3'-end with a ribose comprising a 2',3'-cyclic phosphate linkage is also less likely to be oxidized to aldehydes and thus less likely to be capable of being labeled using one or more of the labels described herein. Cleavage products created by this reaction can comprise a ribose with a 5'-hydroxyl terminus and a 3'-phosphate linkage. Such a cleavage product does not contain a 5'-terminal ribose comprising a diol moiety. Thus, 2' or 5'-hydroxyl groups of a cleavage product with a 5'-end comprising a 5'-hydroxyl terminus and ribose with a 3'-phosphate linkage are less likely to be oxidized to aldehydes and thus less likely to be capable of being labeled using one or more of the labels described herein. Thus, in some embodiments, any first or second ends of the nucleic acid with 5'-phosphate, 5'-hydroxyl, 2' phosphate, 3'-phosphate, or 2'-3'-linked phosphate groups can remain substantially unlabeled with one or more labels.

In some embodiments, a label can target an intact 3'- or 5'-end of an mRNA molecule with a ribose-diol and not label a 3' or 5' end of an mRNA molecule with an end ribose comprising a 2',3'-cyclic phosphate linkage or derivative thereof. In some embodiments, a label can target an intact 3'- or 5'-end of an mRNA molecule with a ribose-diol more efficiently than a 3'- or 5'-end of an mRNA molecule with a 3'- or 5'-end ribose comprising a 2',3'-cyclic phosphate linkage or derivative thereof. For example, a label can target an intact 3'- or 5'-end of an mRNA molecule with a ribose-diol at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 3'- or 5'- of an mRNA molecule with a 3'- or 5'-end ribose comprising a 2',3'-cyclic phosphate linkage or derivative thereof.

In some embodiments, a label can target an intact 3'- or 5'-end of an mRNA molecule with a ribose-diol and not label a 3' or 5' end of an mRNA molecule with an end ribose comprising a 2' phosphate linkage, 3'-phosphate linkage, or derivative thereof. In some embodiments, a label can target an intact 3'- or 5'-end of an mRNA molecule with a ribose-diol more efficiently than a 3'- or 5'-end of an mRNA molecule with 2' phosphate linkage, 3'-phosphate linkage, or derivative thereof. For example, a label can target an intact 3'- or 5'-end of an mRNA molecule with a ribose-diol at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 3'- or 5'- of an mRNA molecule with a 2' phosphate linkage, 3'-phosphate linkage, or derivative thereof.

In some embodiments, a label can target an intact 3'- or 5'-end of an mRNA molecule with a ribose-diol and not label a 3' or 5' end of an mRNA molecule with an end ribose comprising a 5'-phosphate, 5'-hydroxyl, or derivative thereof. In some embodiments, a label can target a derivative of an intact 3'- or 5'-end of an mRNA molecule with a ribose-diol more efficiently than a 3'- or 5'-end of an mRNA molecule with 5'-phosphate, 5'-hydroxyl, or derivative thereof. For example, a label can target an intact 3'- or 5'-end of an mRNA molecule with a ribose-diol at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 3'- or 5'- of an mRNA molecule with a 5'-phosphate, 5'-hydroxyl, or derivative thereof.

Non-Selective End Labeling

Provided herein are methods for detecting degraded or fragmented nucleic acids (e.g., RNA), comprising non-selectively end-labeling the nucleic acids. Non-selective labeling can involve exploiting the differential terminal chemistry between intact mRNA molecules and degraded RNA, such as RNA degraded by RNAses. An intact mRNA molecule can be labeled by a labeling chemistry that non-selectively labels either one or both intact termini of an mRNA molecule. Although a label can be capable of labeling an intact terminus of the mRNA, often it is not capable of labeling a degraded terminus, such as a terminus without a ribose diol. In some embodiments, a label can target an intact terminus of the mRNA more efficiently than it labels a degraded terminus. For example, a label can target an intact terminus of the mRNA at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than it targets a degraded terminus. In some cases, a single label is used; in some cases, more than one label is used (e.g., 2, 3, 4, 5, 6, 7, 8, 9, or 10, 15, 20 or more labels). In some cases, at least two different labels can be used. Although, each of one or more labels can be capable of labeling an intact terminus of the mRNA, they can label an intact terminus of the mRNA more efficiently than they label a degraded terminus. For example, each of one or more labels can label an intact terminus of the mRNA at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than label a degraded terminus. For example, a first label can label an intact terminus of the mRNA at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a degraded terminus, and a second label can label an intact terminus of the mRNA at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a degraded terminus.

FIG. 1 illustrates a general overview according to some embodiments of the invention for estimation of mRNA degradation in a sample (101). This figure and remaining figures provided in the present disclosure are for illustrative purposes only and are not intended to limit the invention. The steps in FIG. 1 can be performed in any suitable order and combination, and can also be combined with any other steps of the present disclosure. According to some embodiments, a sample comprising mRNA is obtained (111). The mRNA can be from any suitable source known in the art and many exemplary sources are described elsewhere in this application. The mRNA terminal moieties within the sample can be subjected to a preparative chemical step to facilitate labeling (121), such as a conversion of terminal ribose diols to aldehydes, which is further detailed in FIG. 3 and elsewhere in the application. In some cases, the method uses non-selective end labeling of the termini. In some cases, labels can be attached to intact mRNA terminal ends (131) as described herein. In some embodiments, labels cannot be attached to degraded mRNA ends, such as ends lacking a 5'-cap or 3'-poly(A) tail, or ends lacking a ribose diol.

In alternative embodiments, a label can target degraded mRNA ends at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than intact mRNA ends.

Labels can comprise a reporter moiety, such as a fluorescent moiety. Fluorescent dyes can include, but are not limited to, DAPI, 5-FAM, 6-FAM, 5(6)-FAM, 5-ROX, 6-ROX, 5,6-ROX, 5-TAMRA, 6-TAMRA, 5(6)-TAMRA SYBR, TET, JOE, VIC, HEX, R6G, Cy3, NED, Cy3.5, Texas Red, Cy5, and Cy5.5. In some embodiments, a reporter quencher pair can be utilized, for example, one on each end of the mRNA. In some embodiments, a Foerster resonance energy transfer (FRET) or fluorescence transfer energy transfer donor/acceptor pair can be utilized in labels on the opposite ends of a mRNA. In some embodiments, a label comprises an affinity molecule, such as biotin. In some embodiments, an affinity molecule can be attached to a reporter moiety, such as those described above. In some embodiments, an affinity molecule is not attached to a reporter moiety.

A sample containing mRNA can be separated into a plurality of partitions (141) using any suitable method known in the art, such as methods using microdroplets, microfluidic devices, microwells, or capillary structures. In some embodiments, a separation can be before labeling. In some embodiments, separation can be after labeling. In some cases, a sample is diluted. A dilution step can be guided by the amount of total mRNA in the sample, in some cases by quantifying the total mRNA in the sample (161). The total mRNA can be determined by any known method in the art, such as spectroscopy, use of an Agilent 2100 Bioanalyzer, NanoDrop, or use of a dye, such as DAPI, Hoechst Dyes, PicoGreen, RiboGreen, OliGreen, Alexa dyes, and cyanine dyes such as YO-YO, ethidium bromide, and SybrGreen. For example, using UV spectroscopy, the absorbance of a RNA sample can be measured at 260 nm and 280 nm. Nucleic acid concentration can then be calculated using the Beer-Lambert law, which predicts a linear change in absorbance with concentration. Total mRNA levels and concentration can be determined by comparing a signal from a test sample to that of a reference sample with a known concentration of mRNA.

The number of partitions can be adjusted to contain an optimal concentration or amount of mRNA in a given volume. For example, a dilution can result in on average less than 1 mRNA molecule per partition, per microdoplet, per length of capillary, or per unit volume. Following partitioning, the number of partitions containing one or more labels can be assessed (151). In some cases, a total signal from a measurement indicates the total amount of label in a diluted sample volume. In some embodiments, separate ends of an mRNA molecule are labeled with different reporter moieties and the presence of none, one, or more of the moieties is detected. In some cases, a quantity of each reporter from a given sample volume can be detected.

Following enumerating the number of partitions containing one or more labels (151), an analysis step can be conducted to evaluate a level of degradation or fragmentation of nucleic acids (e.g., RNA) in a sample. A single label can be used to label RNA, or more than one label can be used. In cases where a single label is used, an analysis step can comprise determining a relative signal or fluorescence of the individual partitions. Partitions that comprise completely fragmented RNA and empty partitions generally can have relatively low, or no fluorescence compared to other partitions. Partitions comprising an RNA strand that is partially degraded (e.g., at one terminus) can emit a moderately higher signal or fluorescence than the empty partitions; partitions containing the partially degraded sample thus can be referred to as "moderate signalers." Partitions with intact RNA can generally have an even higher signal than partitions containing partially-degraded nucleic acids, possibly about double the signal or even greater and can be referred to as "high signalers". Enumerating relative quantity of empty partitions, moderate signaler partitions, and high signaler partitions can enable determination of level of degradation of RNA in a sample. For example, a relative decrease in high signalers, particularly when compared to moderate signalers, can indicate increased degradation. The determination of the level of degradation of RNA in a sample can further comprise, or be enabled by, (a) a comparison to a reference sample or (b) calculation or normalization based on the total concentration of RNA in the target partitions. A reference sample can be, for example, a sample with a known ratio of intact:degraded nucleic acids; a sample with a known quantity of degraded nucleic acids, a sample that substantially contains no degraded nucleic acids, or a sample with substantially no non-degraded nucleic acids.

In cases where more than one label is used to label RNA, an analysis step can also comprise determining the relative signal or fluorescence of the individual partitions. For example, if two fluorescent labels are used, such as a red label and a green label, partitions that comprise completely fragmented RNA and empty partitions generally can again have relatively low fluorescence compared to other partitions. Partitions comprising an RNA strand that is partially degraded (e.g., at one terminus) can comprise a single color, such as either green or red; partitions containing the partially degraded sample thus can be referred to as "single positive". Partitions with intact RNA can comprise either: (1) a single color if both ends are labeled with the same color "single positive" or (2) "double positive", if each end is labeled with a different color. Furthermore, partitions with intact RNA, assuming similar labeling efficiencies and a random distribution of colors, would be expected to be present in a 1:2:1 ratio of color-A:double-positive:color-B partitions. Enumerating a relative quantity of empty partitions, single-positive partitions, and double-positive partitions can then help determine a level of degradation in the sample. For example, a relative decrease in double-positive partitions, particularly when compared to single-positive partitions, or to the expected 1:2 distribution per color, can indicate increased degradation. Determination of a level of degradation of RNA in a sample can further comprise, or be enabled by, (a) a comparison to a reference sample or (b) calculation or normalization based on the total concentration of RNA in all of the partitions. The reference sample can be, for example, a sample with a known ratio of intact:degraded nucleic acids; a sample with a known quantity of degraded nucleic acids, a sample that substantially contains no degraded nucleic acids, or a sample with essentially no non-degraded nucleic acids.

As mentioned above, determining the total or starting concentration of the nucleic acid (e.g., RNA) can be a step in many of the methods herein. The concentration can be used to normalize or further help quantify the amount of RNA degradation. For example, if the sample comprised RNA that is highly degraded such that neither terminus is labeled following a labeling step described herein, it can be difficult to determine whether a low-signaling partition comprises no nucleic acids or completely degraded nucleic acids. Similarly, if the RNA is degraded at both ends, there can be a reduced number of, for example, single positive and double-positive partitions, but the relative number may not necessarily be changed. However, if the starting concentration is known, one can be able to calculate the total number of partitions expected to comprise RNA.

Optionally, the amount of mRNA in the sample can be quantified (161) using any suitable method known in the art, such as spectroscopy, use of an Agilent 2100 Bioanalyzer, NanoDrop, and/or use of a dye, such as DAPI, Hoechst Dyes, PicoGreen, RiboGreen, OliGreen, Alexa dyes, and cyanine dyes such as YO-YO, ethidium bromide, and SybrGreen. For example, using UV spectroscopy, the absorbance of a RNA sample can be measured at 260 nm and 280 nm. The nucleic acid concentration can then be calculated using the Beer-Lambert law, which predicts a linear change in absorbance with concentration. In some embodiments, the total mRNA can be determined by comparing a signal from a test sample to that of a reference sample with a known concentration of mRNA. A signal can be a detectable and/or detected energy and/or information. Any signals detected, after detection, can be described as signals and/or data. For example, detected droplet signals can provide test signals and test data, control signals or control data, reference signals and reference data, calibration signals and calibration data, transformed signals and transformed data, or any combination thereof, among others. Signals can be detected from droplets. Signals can include test signals, control signals, reference signals, calibration signals, or any combination thereof. Signals can be analyzed. Analysis can include transforming test signals. Analysis also or alternatively can include comparing test signals and/or transformed test signals to a signal threshold to assign individual droplets as being positive or negative for amplification of a nucleic acid target. A number and/or fraction of target-positive droplets can be determined based on results of the comparison. Analysis further can include estimating a presence of a label and/or nucleic acid target in the sample. An estimated presence can be no target in the sample. Estimation of a presence may (or may not) be performed using Poisson statistics.

Figure 2:
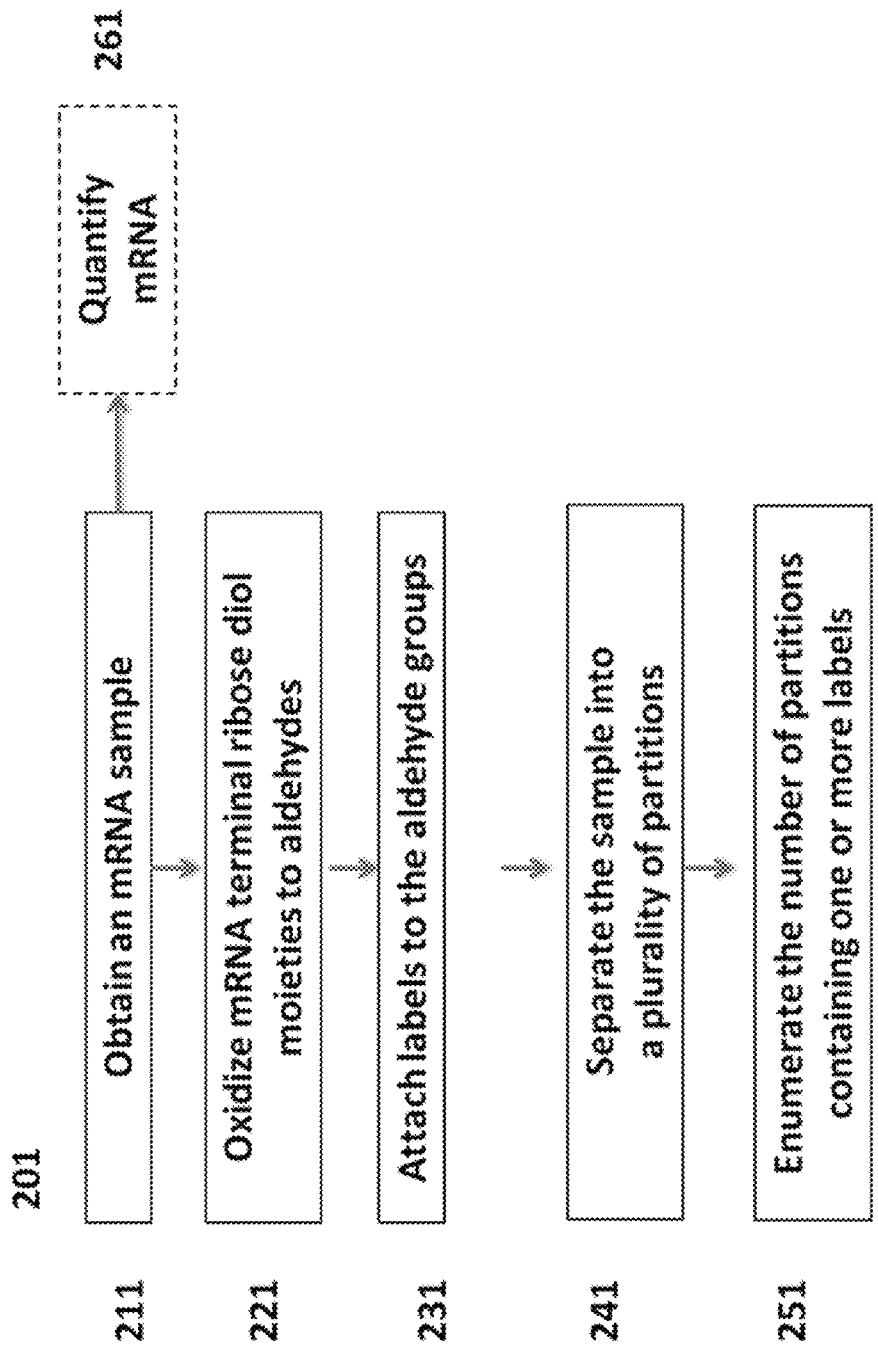
FIG. 2 illustrates a flowchart for a particular embodiment of the assessment of RNA degradation in a sample.

Non-selective labeling can be accomplished in any of a number of methods, including by methods that specifically label intact, but not degraded, termini. For example, intact mRNA termini often comprise terminal ribose diol moieties, while the fragmented termini do not comprise such moieties. The terminal ribose diol moieties can be converted to aldehydes through non-selective oxidization to facilitate labeling of intact RNA fragments. FIG. 2 illustrates a particular embodiment of the method described in FIG. 1 (201). A sample comprising mRNA can be obtained (211). Ribose diol moieties from intact 5'- and 3'-termini can be oxidized to aldehydes (221). In various embodiments, the diol to aldehyde conversion does not occur on any degraded mRNA molecules lacking the terminal ribose diols. In various embodiments, an aldehyde conversion occurs on degraded mRNA molecules lacking the terminal ribose diols less efficiently than the diol to aldehyde conversion occurs on intact mRNA ends containing terminal ribose diols. For example, the aldehyde conversion occurs on degraded mRNA molecules lacking the terminal ribose diols at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than the diol to aldehyde conversion occurs on intact mRNA ends containing terminal ribose diols.

Labels can be attached to the aldehyde groups (231). Any of the labeling groups discussed elsewhere in the application or any other suitable labeling groups can be utilized to label the mRNA molecules. A sample can be separated into a plurality of partitions (241). A separation step (or dilution) can be before or after labeling. A separation or dilution step can be guided by the total amount of mRNA in the sample, in some cases by optionally quantifying the total mRNA in the sample (261). The dilution or the number of partitions can be adjusted to contain an optimal concentration or amount of mRNA in a given volume. For example, a dilution can result in approximately on average less than 1, 2, 3, 4, or 5 mRNA molecules per partition, per length of capillary, or per unit volume. The number of partitions containing one or more labels can be assessed (251). In some embodiments, a total signal from a measurement indicates the total amount of label in a diluted sample volume. In some embodiments, separate ends of an mRNA molecule are labeled with different reporter moieties and the presence of none, one, or more of the moieties is detected. In some cases, a quantity of each reporter from a given sample volume can be detected. A number of partitions containing one or more labels can be assessed (251).

Figure 3:
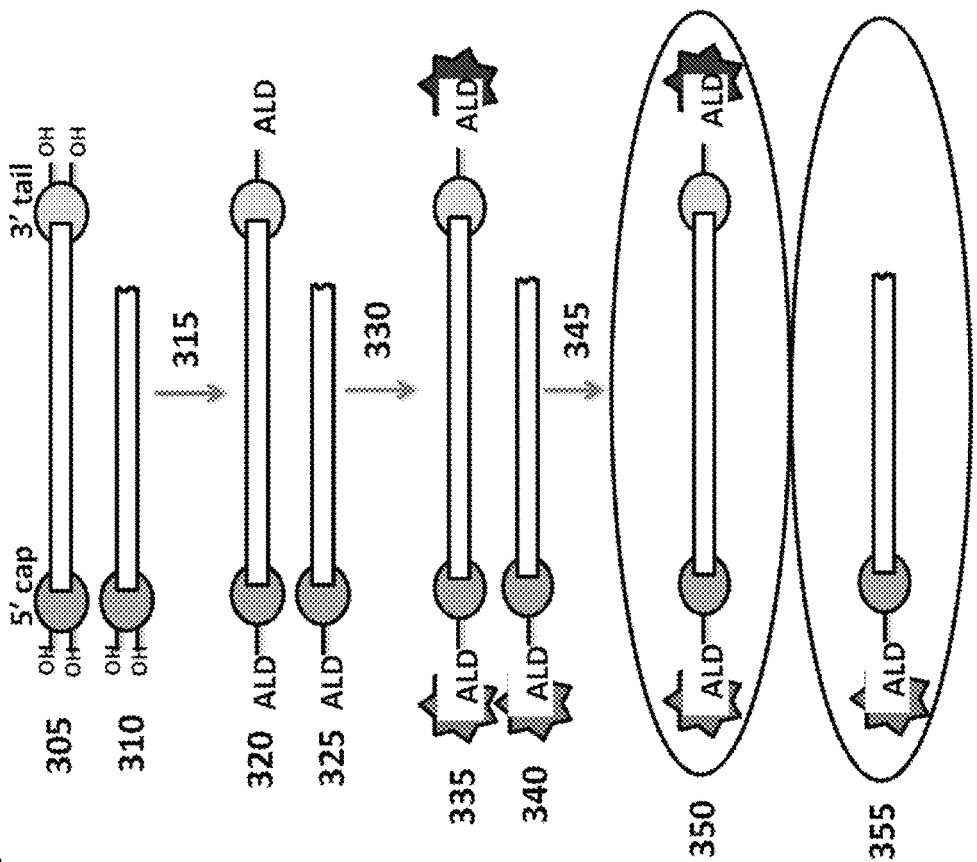
FIG. 3 illustrates an example of the method described in FIG. 2, using an mRNA sample that contains an intact mRNA molecule and a partially degraded mRNA molecule.

FIG. 3 illustrates an example of the method described in FIG. 2 (301), using an mRNA sample that contains an intact mRNA molecule (305) and a partially degraded mRNA molecule (310). In some embodiments, the intact mRNA comprises ribose diol moieties at its 5'-cap and 3'-tail ends, whereas the partially degraded mRNA comprises only one ribose diol moiety, for example at its 5'-cap or 3'-tail end.

Degraded mRNA molecules can lack ribose diols on both ends as well (not shown). The ribose diol moieties can be oxidized to aldehydes (315) such as in FIG. 11, which can result in an intact mRNA molecule with aldehydes at both ends (320) and the partially degraded mRNA molecule with only one aldehyde group (325). A sample can then be subjected to a labeling step (330), such as by contacting the sample with equimolar concentrations of two fluorophores that react with the aldehyde groups. In some embodiments, a sample can then be subjected to a labeling step (330), such as by contacting the sample with a first concentration of a first fluorophore and a second concentration of a second fluorophore such that each of the fluorophores react with the aldehyde groups substantially equally. For example, the concentrations of each of the fluorophores can be adjusted based on their labeling efficiencies. Under similar labeling efficiencies, or adjusted fluorophore concentrations as described above, on average, about 50% of the intact mRNA molecules can have a separate fluorophore on each end. A degraded mRNA molecule with a single ribose diol can on average have the first fluorophore on the ribose diol end about 50% of the time and the second fluorophore about 50%, while an end lacking the ribose diol would remain substantially unlabeled. In some cases, a labeling step results in an intact mRNA molecule with two different labels (335) on each end or the same label on each end (not shown) and a partially degraded mRNA molecule with only one label (340). A sample can be separated into a plurality of partitions (345). The partitioning step can result in a partition, such as a droplet, containing two labels, which can indicate an intact mRNA molecule (350), and can result in an additional partition containing only one label, which can indicate a partially degraded mRNA molecule (355). In some embodiments, partitions are droplets. Partitions containing the first label, the second label, both labels, and/or no labels can be counted. The ratio of intact versus degraded mRNA can be determined by comparing experimental results to predicted or controlled reference numbers or fractions of partitions of various label types. In some embodiments, label associated signals originating from the partitions are quantified. In some embodiments, there is only one type of label. In some embodiments, there are two types of labels. In some embodiments, there are two more types of labels. In some embodiments, the ratio of intact versus degraded mRNA in the original sample is determined using the amount of signal from each partition. In some embodiments, the ratio of intact versus degraded mRNA in the original sample is determined by comparing the amount of signal from each partition to a reference partition or sample, such as a partition containing a known ratio of intact versus degraded mRNA.

A method provided herein can comprise labeling an end of a nucleic acid, such as RNA. One or more labels agent capable of facilitating labeling of the ends can be used to facilitate labeling of a nucleic acid. For example, 1, 2, 3, 4, 5, 6, 7, 8, 9, 10 or more agents capable of facilitating labeling of the ends can be used to facilitate labeling of a nucleic acid. In some embodiments, one or more labels agent capable of facilitating labeling of the ends can be an agent that forms a derivative of an intact 3'-end and a derivative of an intact 5'-end. In some embodiments, at least two agents capable of facilitating labeling of the ends can be used to facilitate labeling of a nucleic acid. In some embodiments, an agent that is capable of facilitating labeling of an end of the nucleic acid can be an oxidizing agent. In some cases, one or more labels agent capable of facilitating labeling of the ends, such as an oxidizing agent, can target ribose diols. In some embodiments, one or more labels agent capable of facilitating labeling of the ends, such as an oxidizing agent, facilitates oxidization of one or more ribose diol groups to aldehydes. In some embodiments, the aldehydes can facilitate the labeling of the ends.

The non-selective end-labeling methods described herein generally apply to non-selectively labeling either the 5'- or 3'-end with the same, or different labels. However, as mentioned above, the methods can also comprise selectively labeling intact RNA termini over degraded RNA termini. A degraded RNA molecule originating from an mRNA molecule can have one or none of the mRNA specific end structures. For example, a degraded RNA molecule originating from an mRNA molecule may not have an intact 5'-cap and may not have an intact 3'-poly(A) tail. As another example, a degraded RNA molecule originating from an mRNA molecule may not have an intact 5'-cap, but may have an intact 3'-poly(A) tail. As another example, a degraded RNA molecule originating from an mRNA molecule may have an intact 5'-cap, but may not have an intact 3'-poly(A) tail. Thus, labeling methods can be selected such that both ends of an intact mRNA molecule are labeled and only one or no end of a degraded mRNA molecule is labeled.

In some embodiments, one or more labels agent capable of facilitating labeling of the ends, such as an oxidizing agent, does not target degraded 3'- or 5'-mRNA ends. In some embodiments, one or more labels agent capable of facilitating labeling of the ends, such as an oxidizing agent, targets degraded 3'- or 5'-mRNA ends less efficiently than intact 3'- and 5'-mRNA ends. For example, one or more labels agent capable of facilitating labeling of the ends, such as an oxidizing agent, targets degraded 3'- or 5'-mRNA ends at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than intact 3'- and 5'-mRNA ends.

In some embodiments, one or more labels agent capable of facilitating labeling of the ends, such as an oxidizing agent, targets degraded 3'- or 5'-mRNA ends less efficiently than 3'- and 5'-mRNA ends containing a ribose diol. For example, one or more labels agent capable of facilitating labeling of the ends, such as an oxidizing agent, targets degraded 3'- or 5'-mRNA ends at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than 3'- and 5'-mRNA ends containing a ribose diol.

Figure 9:
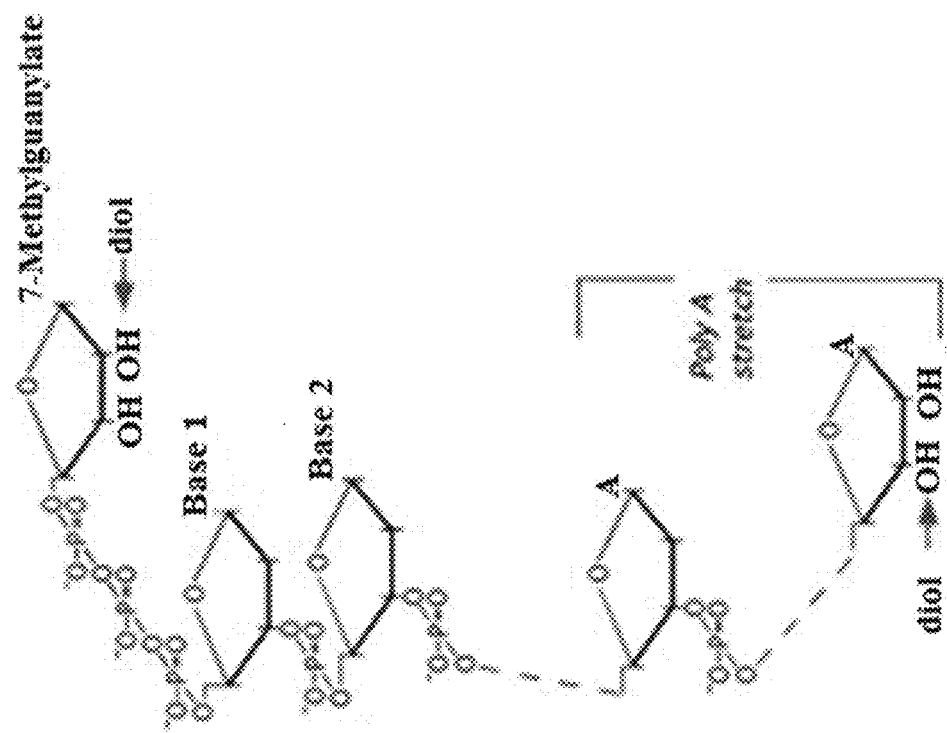
FIG. 9 depicts the diol ends of intact mRNA molecules.
Figure 10:
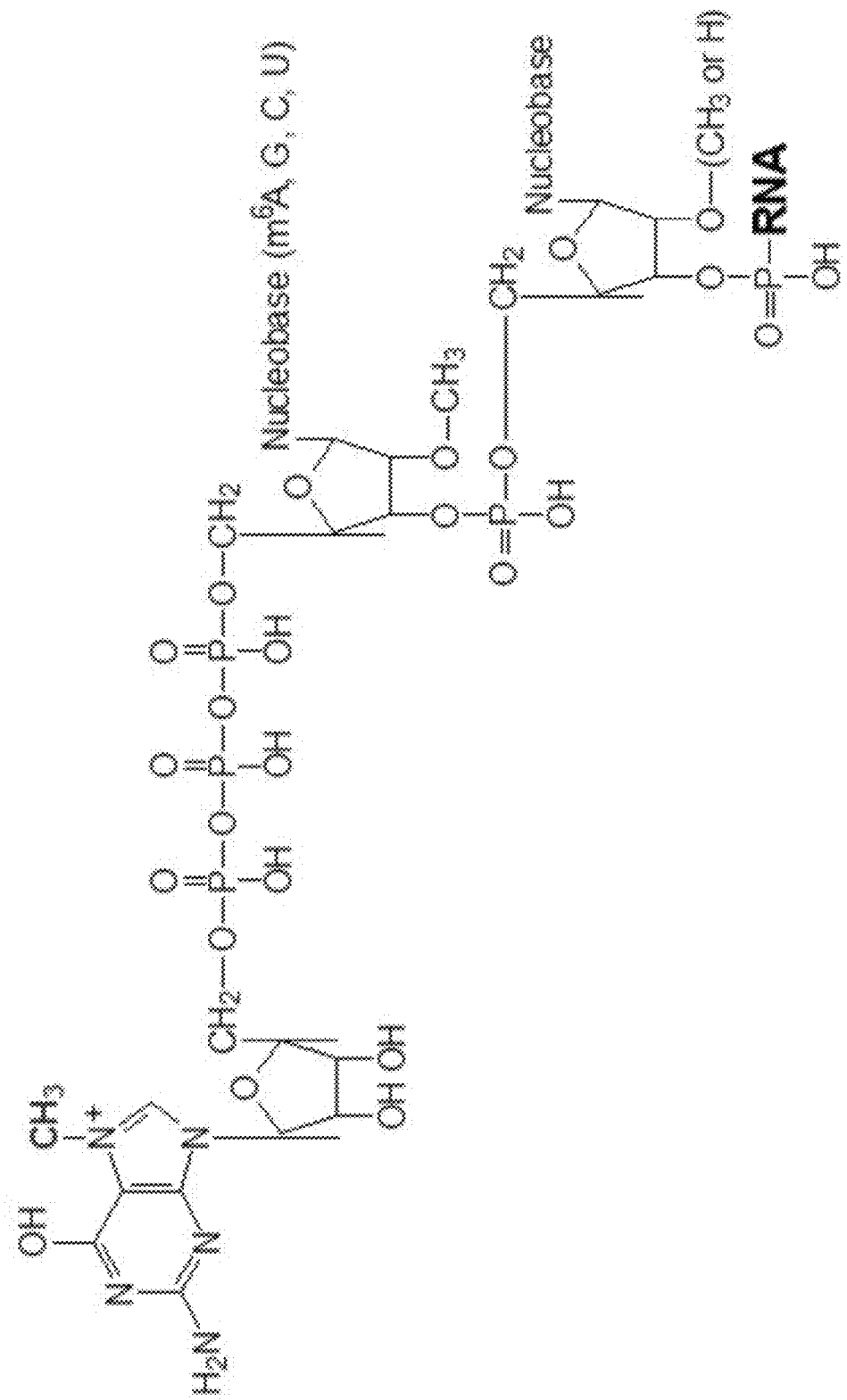
FIG. 10 depicts the structure of a 5'-cap of an mRNA molecule.
Figure 14:
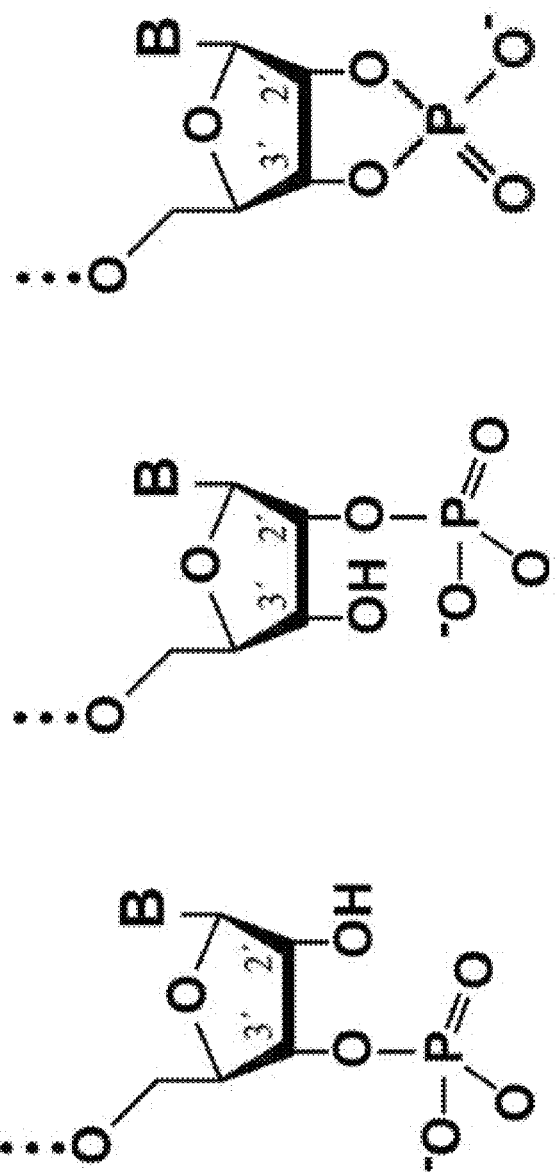
FIG. 14 depicts 3'-RNA ends generated by specific mechanism of degradation.

In various embodiments, the invention relates to methods, compositions, systems, and kits for determining the level of degradation of mRNA in a sample. Intact mRNA molecules have chemical motifs marking the ends of the mRNA, such as 5'-cap structures, 3'-poly(A) tails, and any further relevant motifs (FIGS. 9 and 10). On the other hand, degraded mRNA molecules generally have a different chemistry at one or both ends. A single breakage in an mRNA molecule can result in two RNA molecules, one comprising a 5'-cap and one of many possible 3'-end chemistries, such as a 2', 3'- or 2'-3'-linked phosphate groups (FIG. 14), another comprising a 3'-poly(A) tail and one of various 5'-end chemistries, such as 5'-linked hydroxyl groups, and 5'-linked phosphate groups. Multiple breakages can produce RNA molecules of various chemistries that are generally different, at least on one terminus, from an intact mRNA molecule.

In some embodiments, one or more labels agent capable of facilitating labeling of the ends, such as an oxidizing agent, does not target 2',3'- and/or 2'-3'-linked phosphate groups. In some embodiments, one or more labels agent capable of facilitating labeling of the ends, such as an oxidizing agent, targets 2',3'- and/or 2'-3'-linked phosphate groups less efficiently than intact 3'- or 5'-ends. In some embodiments, one or more labels agent capable of facilitating labeling of the ends, such as an oxidizing agent, targets 2',3'- and/or 2'-3'-linked phosphate groups at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than intact 3'- or 5'-ends. In some embodiments, one or more labels agent capable of facilitating labeling of the ends, such as an oxidizing agent, targets 2',3'- and/or 2'-3'-linked phosphate groups less efficiently than ribose diol groups. In some embodiments, one or more labels agent capable of facilitating labeling of the ends, such as an oxidizing agent, targets 2',3'- and/or 2'-3'-linked phosphate groups at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than ribose diol groups.

In some embodiments, one or more labels agent capable of facilitating labeling of the ends, such as an oxidizing agent, does not target 5'-linked hydroxyl groups and/or 5'-linked phosphate groups. In some embodiments one or more labels agent capable of facilitating labeling of the ends, such as an oxidizing agent, targets 5'-linked hydroxyl groups and/or 5'-linked phosphate groups less efficiently than intact 3'- or 5'-ends. In some embodiments, one or more labels agent capable of facilitating labeling of the ends, such as an oxidizing agent, targets 5'-linked hydroxyl groups and/or 5'-linked phosphate groups at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than intact 3'- or 5'-ends. In some embodiments, one or more labels agent capable of facilitating labeling of the ends, such as an oxidizing agent, targets 5'-linked hydroxyl groups and/or 5'-linked phosphate groups less efficiently than ribose diol groups. In some embodiments, one or more labels agent capable of facilitating labeling of the ends, such as an oxidizing agent, targets 5'-linked hydroxyl groups and/or 5'-linked phosphate groups at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than ribose diol groups.

An oxidizing agent used in the methods described herein can be any oxidizing agent that oxidizes a diol group, but not a 2',3'- or 2'-3'-linked phosphate group, to a group that can be labeled. In some cases, an oxidizing agent used in the methods described herein can be periodate or lead tetraacetate. Other non-limiting examples of agents capable of facilitating labeling of the ends generally include oxidizing agents. The use of PhI(OAc)$_2$ in dichloromethane can be used to perform oxidative cleavage of 1,2-diols to aldehydes. In the presence of OsO$_4$ as catalyst, NMO and 2,6-lutidine, olefinic bonds can be cleaved in acetone/water to yield the corresponding carbonyl compounds. (K. C. Nicolaou, V. A. Adsool, C. R. H. Hale, Org. Lett., 2010, 12, 1552-1555). Other non-limiting examples of agents capable of facilitating labeling of the ends generally include oxidizing agents that target ribose diol groups or intact 3'- and 5'-mRNA ends more efficiently than 5'-linked hydroxyl groups and/or 5'-linked phosphate groups. Other non-limiting examples of agents capable of facilitating labeling of the ends generally include oxidizing agents that target ribose diol groups or intact 3'- and 5'-mRNA ends more efficiently than 2',3'- and/or 2'-3'-linked phosphate groups.

In some cases, an agent suitable to modify an intact 5'-cap structure of an mRNA molecule would not be suitable to modify a degraded 5'-end of an mRNA molecule lacking a 5'-cap structure. An agent can target an mRNA molecule with a 5'-cap structure but not target the 5'-end of a degraded mRNA that lacks a 5'-cap structure. An agent can target an intact 5'-cap structure of an mRNA molecule more efficiently than a degraded 5'-end of an mRNA molecule lacking a 5'-cap structure. For example, an agent can target a 5'-cap structure of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a degraded 5'-end of an mRNA molecule that lacks a 5'-cap structure.

In some cases, a agent suitable to modify an intact 3'-poly(A) tail end structure of an mRNA molecule would not be suitable to modify a degraded 3'-end of an mRNA molecule lacking an intact 3'-poly(A) tail end structure. In some embodiments, an agent can target an intact 3'-poly(A) tail end structure of an mRNA and cannot target a degraded 3'-end of an mRNA molecule lacking a 3'-poly(A) tail end structure. In some embodiments, an agent label can target an intact 3'-poly(A) tail end structure of an mRNA more efficiently than a degraded 3'-end of an mRNA molecule lacking a 3'-poly(A) tail end structure. For example, an agent can target an intact 3'-poly(A) tail end structure of an mRNA at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a degraded 3'-end of an mRNA molecule lacking a 3'-poly(A) tail end structure.

In some embodiments, an agent suitable to modify an intact 3'-poly(A) tail end structure of an mRNA that would not be suitable to modify a degraded 3'-end of an mRNA molecule lacking an intact 3'-poly(A) tail end structure can also be suitable to modify an intact 5'-cap structure of an mRNA molecule. In some embodiments, an agent suitable to modify an intact 5'-cap structure of an mRNA molecule that would not be suitable to modify a degraded 5'-end of an mRNA molecule lacking an intact 5'-cap structure can also be suitable to modify an intact 3'-poly(A) tail end structure of an mRNA molecule.

Labeled mRNA molecules can be tested for the presence of one or both labeled ends per molecule. A sample can be diluted such labeled and/or unlabeled mRNA molecules can be probed at as few as one at a time. A dilution can comprise separating mRNA molecules into partitions. In some embodiments, partitions contain, on average, 1 or fewer mRNA molecules. In some embodiments, partitions contain, on average, 1 or fewer intact mRNA molecules. Detection of labels on both ends of an mRNA molecule in the same partition can indicate that the mRNA molecule is not degraded. If labels are present on a single end of an mRNA molecule in the same partition, this can indicate the mRNA molecule is degraded. If labels are not present on either end of an mRNA molecule in the same partition, this can indicate the mRNA molecule is degraded.

Selective End Labeling

As described above, all mRNA possess two common sites, the poly(A) tail and the 5'-cap, in which the terminal riboses have diol moieties. These can be non-selectively oxidized to aldehydes and coupled to a reporter molecule (e.g. biotin) through a hydrazine linkage. Sites at which RNA degradation has occurred on the molecule can be tailed with a 2'- or 3'-phosphates or a 2'-3'-linked phosphate group and can be less likely to undergo this reaction. Introduction of 2 labels at equimolar concentration will randomly label either end of the mRNA species, resulting in a normal distribution of linked and unlinked labeled molecules. If labeling is applied to a degraded RNA sample, fully unlinked molecules will be observed, providing an index of degradation state.

Ideally, however, a method to selectively modify each end of the mRNA molecule is desirable.

In some embodiments of the invention, an intact end of an mRNA molecule can be selectively modified using an agent, such as an enzyme or compound, which selectively modifies a particular terminus of the intact mRNA (e.g., an intact 5'- or 3'-terminus). In some embodiments of the invention, a modified end of an mRNA molecule can be selectively modified using an agent, such as an enzyme or compound, which selectively modifies a particular terminus of a modified mRNA (e.g., a previously modified 5'- or 3'-terminus).

In some embodiments of the invention, a first agent can facilitate the labeling of a modified first end structure of the nucleic acid and, optionally, a second agent can facilitate the labeling of an intact second end of the nucleic acid. Labeling of the modified first end structure and intact second end structure with one or more labels can comprise labeling the modified first end with a first label specific to a modified first end structure and the second end with a second label specific to an intact second end structure.

In some embodiments, a first agent can facilitate labeling of a modified first end structure of a nucleic acid, and, optionally, a second agent can facilitate labeling of a modified second end structure of a nucleic acid. In some embodiments, labeling of a modified first end structure and a modified second end structure with one or more labels can comprise labeling a modified first end with a first label specific to a modified first end structure and a modified second end with a second label specific to a modified second end structure.

In some embodiments, a derivative of a first end of a nucleic acid molecule, such as mRNA, is different than a derivative of a second end of a nucleic acid molecule. For example, a derivative of a 3'-end can be different than a derivative of a 5'-end. The different chemistries associated with the first and second modified ends can be used to selectively label the ends. In some embodiments, a derivative of a first end of a nucleic acid molecule, such as mRNA, is different than an intact second end of a nucleic acid molecule. For example, a derivative of a 3'-end can be different than an intact 5'-end. For example, a derivative of a 5'-end can be different than an intact 3'-end. The different chemistries associated with the modified first end and intact second end can be used to selectively label the ends. In some embodiments, a derivative of a first end of a nucleic acid molecule, such as mRNA, is different than a degraded second end of a nucleic acid molecule. For example, a derivative of a 3'-end can be different than a degraded 5'-end. For example, a derivative of a 5'-end can be different than a degraded 3'-end. The different chemistries associated with the modified first end and degraded second end can be used to selectively, or non-selectively, to label the ends.

Thus, an intact mRNA molecule can be labeled using a labeling chemistry that selectively targets a particular terminus of the intact mRNA (e.g., an intact or modified 5'- or 3'-terminus). Thus, an intact mRNA molecule can be labeled by using a label or labeling chemistry that is specific to one terminus of the intact mRNA and/or using another label or labeling chemistry that is specific to the other terminus of the intact mRNA.

In some embodiments, a derivative of an intact end of an mRNA molecule can be selectively labeled using a label which selectively targets a particular derivative of an intact terminus of an mRNA (e.g., a derivative of a 5'- or 3'-terminus). In some embodiments, a label can target a derivative of a first end of a nucleic acid molecule, such as mRNA, and not target an intact second end of a nucleic acid molecule. For example, a label can target a derivative of a 3'-end and not target an intact 5'-end. For example, a label can target a derivative of a 5'-end and not target an intact 3'-end. In some embodiments, a label can target a derivative of a first end of a nucleic acid molecule, such as mRNA, and not target a derivative of a second end of a nucleic acid molecule. For example, a label can target a derivative of a 3'-end and not target a derivative of a 5'-end. For example, a label can target a derivative of a 5'-end and not target a derivative of a 3'-end. The selective modifications and/or different chemistries associated with the first and/or second modified ends can be used to selectively label the ends.

In some embodiments, a label can target a derivative of a first end of a nucleic acid molecule, such as mRNA, and not target a degraded second end of a nucleic acid molecule. For example, a label can target a derivative of a 3'-end of a nucleic acid molecule, such as mRNA, and not target a degraded 5'-end. For example, a label can target a derivative of a 5'-end of a nucleic acid molecule, such as mRNA, and not target a degraded 3'-end. The different chemistries associated with the modified first end and a degraded second end can be used to selectively label one or both ends.

Labeling methods can be selected such that both ends of an intact mRNA molecule are each specifically labeled and only one or no end of a degraded mRNA molecule is labeled. Any label described herein, such as those mentioned above for non-selective labeling can be used. In some embodiments, to achieve selective end labeling of mRNA, two labels can be used, such that each of the labels are specific to only one of the mRNA end structures, or derivatives thereof. In some embodiments, to achieve selective end labeling of mRNA, a first population of labels comprising two or more labels and a second populations of labels comprising two or more labels can be used, such that each of the two or more labels of each populations of labels are specific to only one of the intact mRNA end structures, or derivatives thereof.

In some embodiments, a first and a second end of an mRNA molecule can be selectively labeled using a first label which selectively targets the first end (e.g., an intact 5'- or 3'-terminus or derivative of an intact 5'- or 3'-terminus) and a second label which selectively targets the second end (e.g., an intact 5'- or 3'-terminus or derivative of an intact 5'- or 3'-terminus).

In some embodiments, a modified end and an intact end of an mRNA molecule can be selectively labeled using a first label which selectively targets the modified end and a second label which selectively targets the intact end. For example, a modified 3'-end and an intact 5'-end of an mRNA molecule can be selectively labeled using a first label which selectively targets the modified 3'-end and a second label which selectively targets the intact 5'-end. For example, a modified 5'-end and an intact 3'-end of an mRNA molecule can be selectively labeled using a first label which selectively targets the modified 5'-end and a second label which selectively targets the intact 3'-end.

In some embodiments, the first label does not target the intact end. For example, the first label does not target an intact 3'-end. For example, the first label does not target an intact 5'-end.

In some embodiments, the second label does not target the modified end. For example, the second label does not target a modified 3'-end. For example, the first label does not target a modified 5'-end. In some embodiments, the first label does not target a degraded end. In preferred embodiments, the first label and the second label do not target a degraded end.

In some embodiments, a first modified end and second modified end of an mRNA molecule can be selectively labeled using a first label which selectively targets the first modified end and a second label which selectively targets the second modified end. For example, a modified 3'-end and a modified 5'-end of an mRNA molecule can be selectively labeled using a first label which selectively targets the modified 3'-end and a second label which selectively targets the modified 5'-end. For example, a modified 5'-end and a modified 3'-end of an mRNA molecule can be selectively labeled using a first label which selectively targets the modified 5'-end and a second label which selectively targets the modified 3'-end. In some embodiments, the first label does not target the second modified end. For example, the first label does not target a modified 3'-end. For example, the first label does not target a modified 5'-end. In some embodiments, the second label does not target the first modified end. For example, the second label does not target a modified 3'-end. For example, the second label does not target a modified 5'-end. In some embodiments, the first label does not target a degraded end. In some embodiments, the second label does not target a degraded end. In preferred embodiments, the first label and the second label do not target a degraded end.

In some cases, an intact mRNA molecule can be labeled by utilizing a label or labeling chemistry that is specific to the 5'-cap and/or utilizing another label or labeling chemistry that is specific to the 3'-poly(A) tail. For example, an intact mRNA molecule can be labeled by utilizing a label or labeling chemistry that is specific to a derivative of the 5'-cap and/or utilizing another label or labeling chemistry that is specific to the 3'-poly(A) tail or a derivative of the 3'-poly(A) tail. For example, an intact mRNA molecule can be labeled by utilizing a label or labeling chemistry that is specific to a derivative of the 3'-poly(A) tail and/or utilizing another label or labeling chemistry that is specific to the 5'-cap or a derivative of the 5'-cap. Thus, in some embodiments, a first agent can facilitate the labeling of a first end of the nucleic acid and a second agent can facilitate the labeling of a second end of the nucleic acid. In some embodiments, labeling of the first and second end structures with one or more labels comprises labeling the first end with a first label specific to the first end structure and the second end with a second label specific to the second end structure.

Thus, a first label used can be specific to the 5'-cap structure and a second label used can be specific to the 3'-poly(A) tail structure. A first label used can be specific to a derivative of the 5'-cap structure and a second label used can be specific to the 3'-poly(A) tail structure. A first label used can be specific to the 5'-cap structure and a second label used can be specific to a derivative of the 3'-poly(A) tail structure. A first label used can be specific to a derivative of the 5'-cap structure and a second label used can be specific to a derivative of the 3'-poly(A) tail structure.

Figure 4:
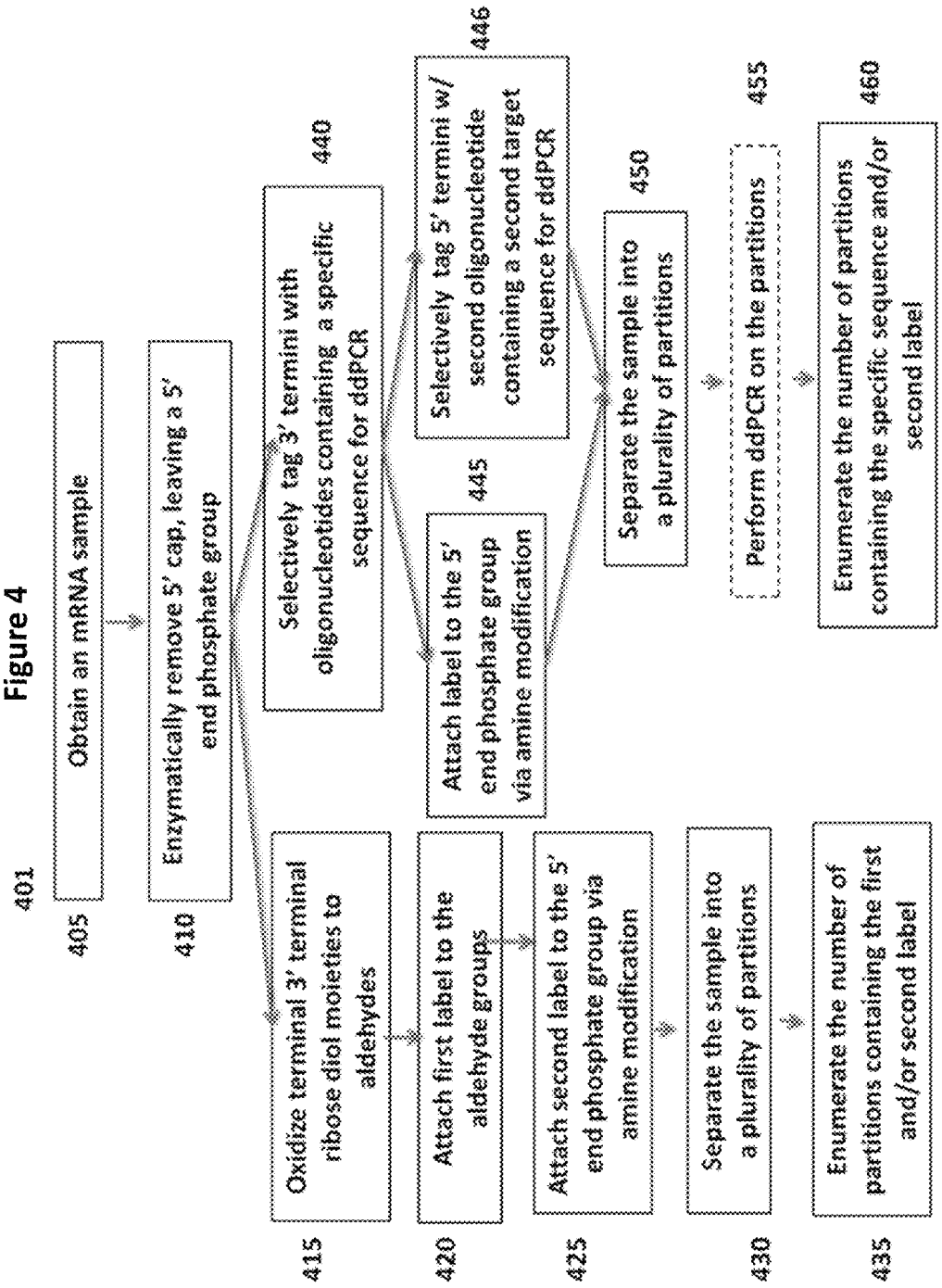
FIG. 4 illustrates a flowchart for the assessment of RNA degradation in a sample, using selective labeling of 5'- and 3'-termini.

FIG. 4 illustrates a workflow of a method for the estimation of mRNA degradation, using selective labeling of the 5'- and 3'-ends (401). A sample comprising mRNA can be obtained (405). 5'-caps can be enzymatically removed, which can leave 5'-phosphates at the 5'-termini (410). The ribose diol moieties can be oxidized to aldehydes (415). A first label can be attached to the aldehyde groups (420). A second label can be attached to the 5'-end phosphate groups, such as by amine modification (425). The sample can be separated into a plurality of partitions (430). The number of partitions containing the first and/or second label can be enumerated (435). Alternatively, after step 410, the 3'-termini can be tagged with oligonucleotides containing a specific sequence for ddPCR (440). A label can then be attached to the 5'-end phosphate groups, such as by amine modification (445).

Figure 5:
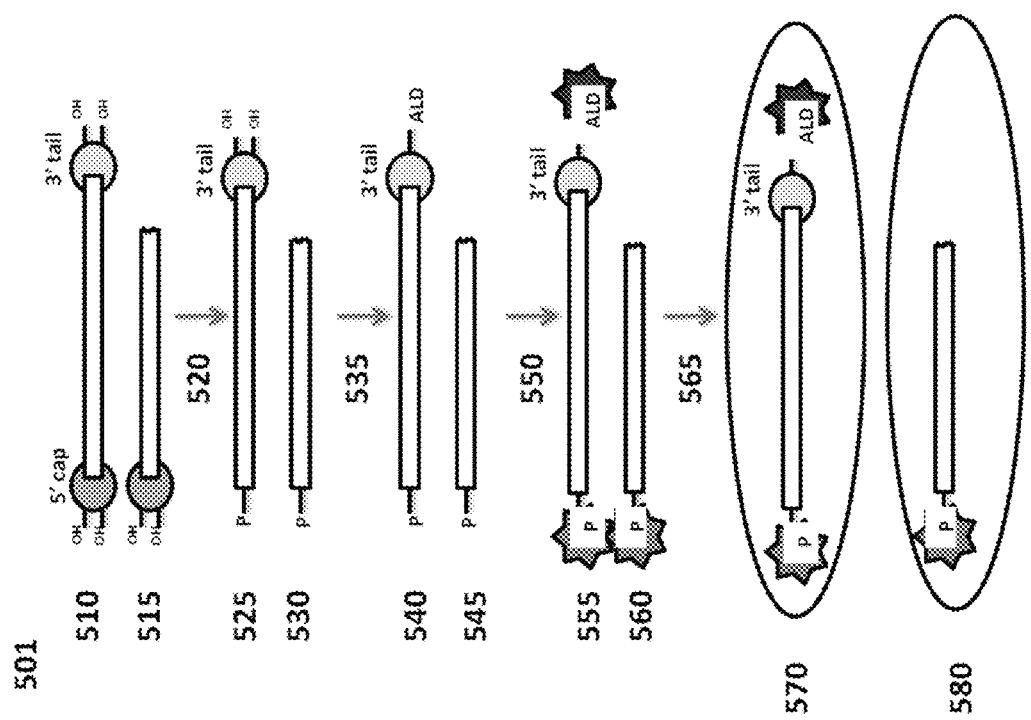
FIG. 5 illustrates an example of the method described in FIG. 3.
Figure 6:
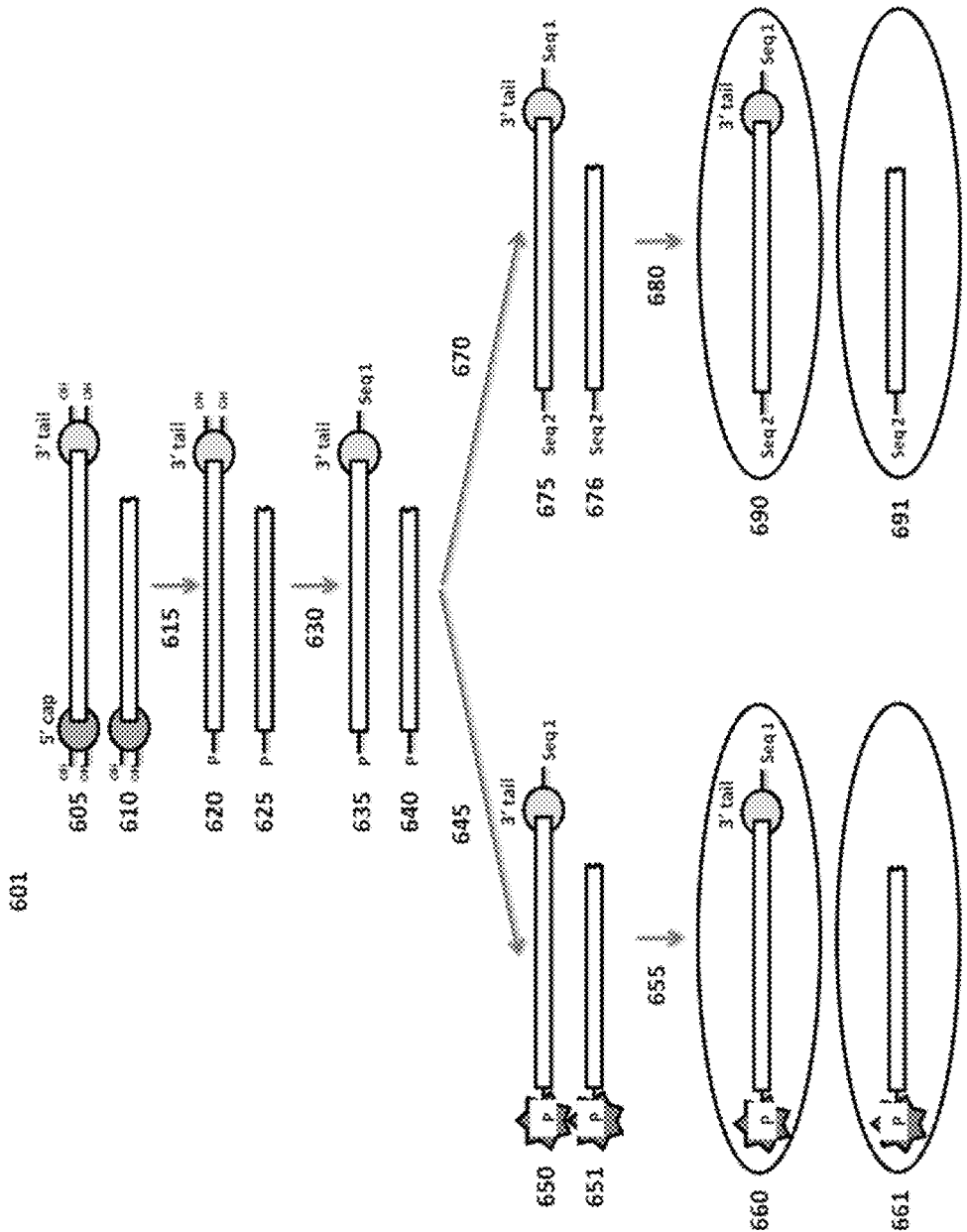
FIG. 6 depicts an analysis of linked assays as a function of high-temperature incubation, which is associated with mRNA degradation.
Figure 7:
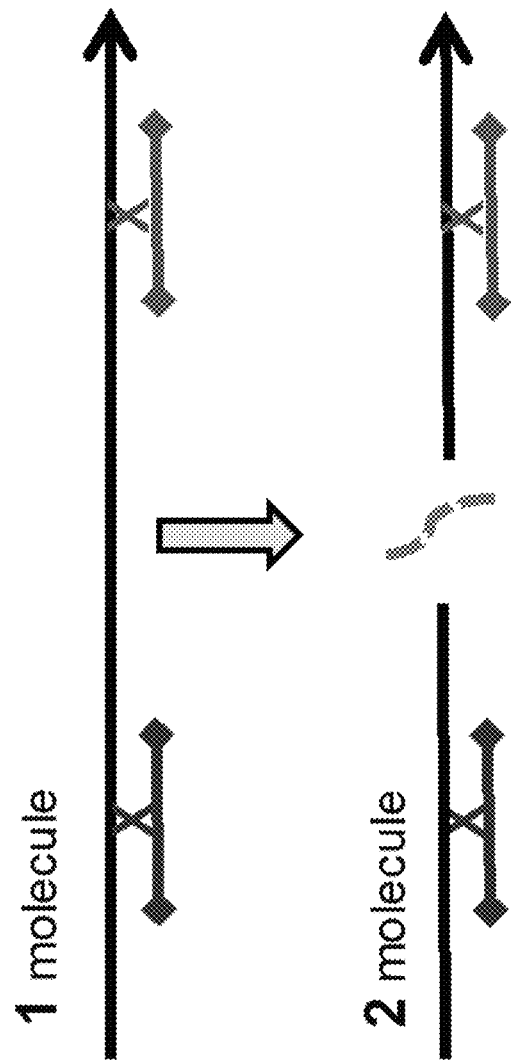
FIG. 7 is a depiction showing RNA degradation can cause an increase in cDNA detection using a FAM-FAM dual assay.
Figure 8:
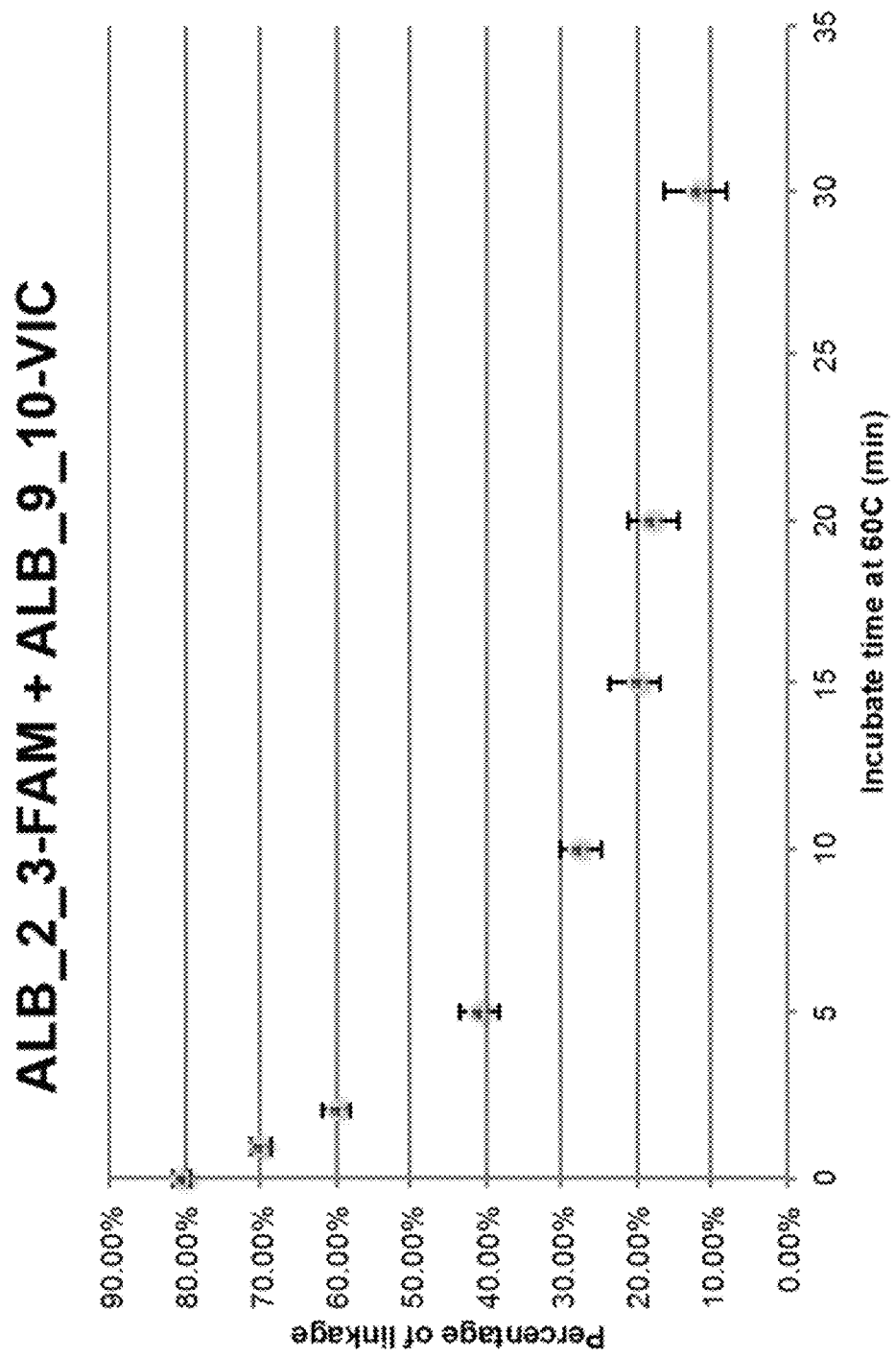
FIG. 8 is a graphical depiction showing the percentage of linkage of RNA can decrease over time.

Alternatively, the 5'-phosphate end can be tagged with oligonucleotides containing a second specific sequence for ddPCR (446). The sample can be separated into a plurality of partitions (450). ddPCR can be performed within the droplets, amplifying the first and/or second sequences (455). The number of partitions containing the first specific sequence and/or the label or second specific sequence can be enumerated (460). FIG. 5 provides a schematic of a method comprising enzymatic removal of a 5'-cap. Here, an intact RNA molecule (510) and degraded RNA molecule (515) are each subjected to enzymatic removal of the 5'-caps (525), (530). The 3'-terminal ribose diol moieties are then selectively oxidized to aldehydes (540), followed by labeling of the aldehyde groups and attachment of a second label to the 5'-end phosphate group by amine modification (555, 560). The method can then comprise enumerating the partitions comprising first and/or second labels.

In some cases, a label or agent that selectively targets the 5'-end of an RNA molecule and not the 3'-end of an RNA molecule can be used. In some cases, a label or agent that selectively targets the intact 5'-end of an RNA molecule and not the intact 3'-end of an RNA molecule can be used. In some cases, a label or agent that selectively targets a derivative of an intact 5'-end of an RNA molecule and not an intact 3'-end of an RNA molecule can be used. In some cases, a label or agent that selectively targets an intact 5'-end of an RNA molecule and not a derivative of the 3'-end of an RNA molecule can be used. In some cases, a label or agent that selectively targets a derivative of an intact 5'-end of an RNA molecule and not a derivative of the 3'-end of an intact RNA molecule can be used.

In some cases, a label or agent that selectively targets the 3'-end of an RNA molecule and not the 5'-end of an RNA molecule can be used. In some cases, a label or agent that selectively targets the intact 3'-end of an RNA molecule and not the intact 5'-end of an RNA molecule can be used. In some cases, a label or agent that selectively targets a derivative of an intact 3'-end of an RNA molecule and not a derivative of the 5'-end of an RNA molecule can be used. In some cases, a label or agent that selectively targets an intact 3'-end of an RNA molecule and not a derivative of the 5'-end of an RNA molecule can be used. In some cases, a label or agent that selectively targets a derivative of an intact 3'-end of an RNA molecule and not a derivative of the 5'-end of an intact RNA molecule can be used.

In some cases, a label suitable to target a 5'-cap structure of an RNA molecule that would not be suitable to target the 5'-end of a degraded RNA that lacks a 5'-cap, is not suitable to target an intact 3'-poly(A) tail. For example, a label that would not be suitable to target the 5'-end of a degraded RNA that lacks a 5'-cap can target a 5'-cap structure of an RNA molecule more efficiently than intact 3'-poly(A) tail. For example, a label that would not be suitable to target the 5'-end of a degraded RNA that lacks a 5'-cap, can target a 5'-cap structure of an RNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than an intact 3'-poly(A) tail. For example, a label that would not be suitable to target the 5'-end of a degraded RNA that lacks a 5'-cap, can target a derivative of an intact 5'-cap structure of an RNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than an intact 3'-poly(A) tail. For example, a label that would not be suitable to target the 5'-end of a degraded RNA that lacks a 5'-cap, can target a derivative of an intact 5'-cap structure of an RNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a derivative of an intact 3'-poly(A) tail.

In some cases, a label suitable to target a 3'-poly(A) tail structure of an RNA molecule that would not be suitable to target the 3'-end of a degraded RNA that lacks a 3'-poly(A) tail, is not suitable to target an intact 5'-cap structure. For example, a label that would not be suitable to target the 3'-end of a degraded RNA that lacks a 3'-poly(A) tail can target a 3'-poly(A) tail structure of an RNA molecule more efficiently than intact 5'-cap structure. For example, a label that would not be suitable to target the 3'-end of a degraded RNA that lacks a 3'-poly(A) tail, can target a 3'-poly(A) tail structure of an RNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently an than an intact 5'-cap structure. For example, a label that would not be suitable to target the 3'-end of a degraded RNA that lacks a 3'-poly(A) tail, can target a derivative of an intact 3'-poly(A) tail structure of an RNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than an intact 5'-cap structure. For example, a label that would not be suitable to target the 3'-end of a degraded RNA that lacks a 3'-poly(A) tail, can target a derivative of an intact 3'-poly(A) tail structure of an RNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a derivative of an intact 5'-cap structure.

In some embodiments, a first label can be a first oligonucleotide with a first known sequence and a second label can be a second oligonucleotide with a second known sequence. In some embodiments, the first and second oligonucleotide labels contain the same sequence, a portion of the same sequence. In some embodiments, the first and second oligonucleotide labels contain different sequences. In some embodiments, a first label that is first oligonucleotide with a first known sequence can target a 3'-end of an RNA molecule and a second label that is a second oligonucleotide with a second known sequence can target a 5'-end of an RNA molecule. In some embodiments, a first label that is first oligonucleotide with a first known sequence can target a derivative of 3'-end of an RNA molecule and a second label that is a second oligonucleotide with a second known sequence can target a 5'-end of an RNA molecule. In some embodiments, a first label that is first oligonucleotide with a first known sequence can target a derivative of 3'-end of an RNA molecule and a second label that is a second oligonucleotide with a second known sequence can target a derivative of 5'-end of an RNA molecule.

In some embodiments, a first label can be an oligonucleotide with a known sequence and a second label can be a non-oligonucleotide label, such as a fluorophore. In some embodiments, a first label, that is an oligonucleotide with a known sequence, can target a 3'-end of an mRNA molecule, and a second label that is a non-oligonucleotide label, such as a fluorophore, can target a 5'-end. In some embodiments, a first label, that is an oligonucleotide with a known sequence, can target a derivative of a 3'-end of an mRNA molecule, and a second label that is a non-oligonucleotide label, such as a fluorophore, can target a 5'-end. In some embodiments, a first label, that is an oligonucleotide with a known sequence, can target a derivative of a 3'-end of an mRNA molecule, and a second label that is a non-oligonucleotide label, such as a fluorophore, can target a derivative of a 5'-end. In some embodiments, a label can be a 5'-adenylated oligonucleotide blocked at the 3'-end In some cases, to facilitate the labeling specifically towards the 5'-end, the 5'-end of the RNA molecules can be specifically modified such that the label does not label the 3'-end and does label the modified 5'-end. In some cases, to facilitate the labeling specifically towards the 5'-end, both the 3'- and the 5'-ends of the RNA molecules can be specifically modified such that the label does not label the modified 3'-end and does label the modified 5'-end. In some embodiments, to facilitate the labeling specifically towards the 5'-end, the 3'-end of the RNA molecules can be specifically modified or blocked. In some cases, a derivative of the 5'-cap can be formed using a reagent, such as a chemical. In some cases, a derivative of the 5'-cap can be formed using an enzyme. In some cases, the 5'-cap can be removed enzymatically, such as by using TAP as described herein, leaving a 5'-end phosphate group. In some cases, a 5'-end phosphate group can be selectively labeled. In some embodiments, a 5'-end phosphate group can be selectively labeled after an intact 3'-end of an mRNA molecule has been selectively labeled. In some embodiments, a TAP treated 5'-cap can be selectively labeled with a second label after an intact 3'-end of an mRNA molecule has been selectively labeled with a first label.

In some embodiments, a label can be used that targets a derivative of a 5'-cap of an mRNA molecule and not a 3'-poly(A) tail of an mRNA molecule. In some embodiments, a label can target a derivative of a 5'-cap of an mRNA molecule more efficiently than a 3'-poly(A) tail of an mRNA molecule. For example, a label can target a derivative of a 5'-cap of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 3'-poly(A) tail of an mRNA molecule. In other embodiments, a label can target an intact 5'-cap of an mRNA molecule and not a 3'-poly(A) tail of an mRNA molecule with a blocking group.

In some embodiments, a label can target a 5'-end phosphate group of an mRNA molecule and not a 3'-end of a poly(A) tail of an mRNA molecule. In some embodiments, a label can target a 5'-end phosphate group of an mRNA molecule more efficiently than a 3'-end of a poly(A) tail of an mRNA molecule. For example, a label can target a 5'-end phosphate group of an mRNA molecule at least about 2, 3, 4, 5, 6, 7, 8, 9, 10, 15, 20, 30, 40, 50, 60, 70, 80, 90, 100, 500, 1000, 5000, $1^{04}$, $1^{05}$, or $1^{06}$ times more efficiently than a 3'-end of a poly(A) tail of an mRNA molecule. For example, a label can target a 5'-end phosphate group of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a derivative of an intact 3'-poly(A) tail of an mRNA molecule.

In some embodiments, a label can target a 5'-end phosphate group of an mRNA molecule and not a labeled 3'-end of a poly(A) tail of an mRNA molecule. In some embodiments, a label can target a 5'-end phosphate group of an mRNA molecule more efficiently than a labeled 3'-end of the poly(A) tail of an mRNA molecule. For example, a label can target a 5'-end phosphate group of an mRNA molecule at least about 2, 3, 4, 5, 6, 7, 8, 9, 10, 15, 20, 30, 40, 50, 60, 70, 80, 90, 100, 500, 1000, 5000, $1^{04}$, $1^{05}$, or $1^{06}$ times more efficiently than a labeled 3'-end of the poly(A) tail of an mRNA molecule. For example, a label can target a 5'-end phosphate group of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a labeled derivative of an intact 3'-poly(A) tail of an mRNA molecule.

In some cases, the first or second termini of a nucleic acid molecule (e.g., mRNA) can have a blocking moiety that prevents labeling and therefore biases the labeling in favor of the other terminus or derivative thereof. In some embodiments, to achieve selective end labeling of mRNA, a first end of the mRNA can be protected, such as with a blocking moiety, such that the first end cannot be labeled while the second end is left unprotected such that the second end can be labeled. In some embodiments, the 5'-end of the mRNA can be protected such that the 5'-end cannot be labeled while the 3'-end is left unprotected such that the 3'-end can be labeled. In some embodiments, the 3'-end of the mRNA can be protected such that the 3'-end cannot be labeled while the 5'-end is left unprotected such that the 5'-end can be labeled.

Thus, in some embodiments, a label suitable to target a first terminus of an mRNA molecule may not be suitable to label a second terminus of an mRNA molecule with a blocking group. A label suitable to target a first terminus of an mRNA molecule can target a second terminus of an mRNA molecule with a blocking group less efficiently. For example, a label can target a first terminus of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a second terminus of an mRNA molecule with a blocking group.

In some embodiments, a 5'-adenylated oligonucleotide can be a blocking group. In some embodiments, a 5'-adenylated oligonucleotide can be label. In some embodiments, a 5'-adenylated oligonucleotide that is blocked at the 3'-end, such as by attachment to ddA or an $NH_2$ group, can be ligated to a 3'-end of a nucleotide using a ligase, such as T4 RNA ligase and has been described in Lau et al. (2001) *Science*, 294, 858-6. These 5' adenylated, 3' blocked oligodeoxynucleotides have been used for cloning short RNAs according to the procedure of Bartel. RNA ligase recognizes the activated adenylated oligo and covalently ligates its 5' end to the 3' OH of a second single stranded sequence in the absence of ATP. In a mixture of nucleic acids, use of the 5' adenylated, 3' blocked oligo with RNA ligase (w/o ATP) results in ligation of the target oligonucleotide only. The 5'-adenylated oligonucleotide that is blocked at the 3'-end can contain a target sequence for an amplification reaction, such as ddPCR. Subsequently, the 5'-end phosphate can be used as a site to introduce a second unique label, such as an amine reactive fluorophore via amine modification, or a second oligonucleotide tag containing a second target sequence for amplification, such as ddPCR, can be introduced at the 5'-end using a ligase, such as T4 RNA ligase.

In some embodiments, a label can target an intact 5' end of an mRNA molecule and not a 3'-end of the poly(A) tail of an mRNA molecule that is linked to a 5'-adenylated oligonucleotide blocked at the 3'-end. In some embodiments, a label can target an intact 5' end of an mRNA molecule more efficiently than a 3'-end of the poly(A) tail of an mRNA molecule that is linked to a 5'-adenylated oligonucleotide blocked at the 3'-end. For example, a label can target an intact 5' end of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 3'-end of the poly(A) tail of an mRNA molecule that is linked to a 5'-adenylated oligonucleotide blocked at the 3'-end.

In some embodiments, a label can target a derivative of an intact 5' end of an mRNA molecule and not a 3'-end of the poly(A) tail of an mRNA molecule that is linked to a 5'-adenylated oligonucleotide blocked at the 3'-end. In some embodiments, a label can target a derivative of an intact 5' end of an mRNA molecule more efficiently than a 3'-end of the poly(A) tail of an mRNA molecule that is linked to a 5'-adenylated oligonucleotide blocked at the 3'-end. For example, a label can target a derivative of an intact 5' end of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a derivative of a 3'-end of the poly(A) tail of an mRNA molecule that is linked to a 5'-adenylated oligonucleotide blocked at the 3'-end.

In some embodiments, a 5'-adenylated oligonucleotide blocked at the 3'-end can be ligated to a 3' end of an mRNA molecule and cannot be ligated to a 5'-end of an mRNA molecule. In some embodiments, a 5'-adenylated oligonucleotide blocked at the 3'-end can be ligated to a 3' end of an mRNA molecule more efficiently than to a 5'-end of an mRNA molecule. For example, a 5'-adenylated oligonucleotide blocked at the 3'-end can be ligated to a 3' end of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than to a 5'-end of an mRNA molecule.

In some embodiments, a 5'-adenylated oligonucleotide blocked at the 3'-end can be ligated to a 3' end of an mRNA molecule and cannot be ligated to a derivative of a 5'-end of an mRNA molecule. In some embodiments, a 5'-adenylated oligonucleotide blocked at the 3'-end can be ligated to a 3' end of an mRNA molecule more efficiently than to a derivative of a 5'-end of an mRNA molecule. For example, a 5'-adenylated oligonucleotide blocked at the 3'-end can be ligated to a 3' end of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than to a derivative of a 5'-end of an mRNA molecule.

In some embodiments, the 3'-end of the nucleic acid can be blocked and a ligase, such as T4 RNA ligase, can be used to facilitate labeling of the 5'-end of target nucleotide, such as with an oligonucleotide with a target sequence for amplification. For example, the method can comprise removing a 5'-cap structure from the mRNA using TAP, blocking the 3'-end of the RNA molecules; and ligating an oligonucleotide to the RNA by adding T4 RNA ligase and a labeled DNA or RNA primer and/or labeling the RNA with a fluorophore. In such embodiments, the oligonucleotide would ligate to RNA having a 5'-phosphate group. The 3'-end of the nucleic acid can be blocked, for example, by reaction with dideoxynucleotide adenine (ddA) and terminal deoxynucleotidyltransferase (TdT).

In some embodiments, a label can target a derivative of a 5'-cap of an mRNA molecule and not label a 3'-poly(A) tail of an mRNA molecule with a blocking group. In some embodiments, a label can target a derivative of a 5'-cap of an mRNA molecule more efficiently than a 3'-poly(A) tail of an mRNA molecule with a blocking group. For example, a label can target a derivative of a 5'-cap of an mRNA molecule without a blocking group at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 3'-poly(A) tail of an mRNA molecule with a blocking group. In other embodiments, a label can target an intact 5'-cap of an mRNA molecule and not a 3'-poly(A) tail of an mRNA molecule with a blocking group.

In some embodiments, a label can target a derivative of a 5'-cap of an mRNA molecule and not label a derivative of 3'-poly(A) tail of an mRNA molecule with a blocking group. In some embodiments, a label can target a derivative of a 5'-cap of an mRNA molecule more efficiently than a derivative of a 3'-poly(A) tail of an mRNA molecule with a blocking group. For example, a label can target a derivative of an intact 5'-cap of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a derivative of an intact 3'-poly(A) tail of an mRNA molecule with a blocking group.

In some embodiments, a label can target a 5'-end phosphate group of an mRNA molecule and not label an 3'-end of the poly(A) tail of an mRNA molecule with a blocking group. In some embodiments, a label can target a 5'-end phosphate group of an mRNA molecule more efficiently than a 3'-end of the poly(A) tail of an mRNA molecule with a blocking group. For example, a label can target a 5'-end phosphate group of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 3'-end of the poly(A) tail of an mRNA molecule with a blocking group.

In some embodiments, a label can target a 5'-end phosphate group of an mRNA molecule and not label a derivative of a 3'-end of the poly(A) tail of an mRNA molecule with a blocking group. In some embodiments, a label can target a 5'-end phosphate group of an mRNA molecule more efficiently than a derivative of a 3'-end of the poly(A) tail of an mRNA molecule with a blocking group. For example, a label can target a 5'-end phosphate group of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a derivative of an intact 3'-poly(A) tail of an mRNA molecule with a blocking group.

In some cases, to facilitate the labeling specifically towards the 3'-end, the 5'-end of the RNA molecules can be specifically modified, modified, or blocked such that a label does not target the 5'-end and does target an intact 3'-end or a derivative of an intact 3'-end. In some cases, a derivative of the 5'-cap can be formed using a reagent, such as a chemical or an enzyme. A method can comprise removing an intact 5'-cap of an mRNA molecule enzymatically, such by contacting TAP with the mRNA molecule. In some embodiments, the 5'-cap can be removed by using the enzyme TAP, leaving a 5'-end phosphate group that does not contain a ribose diol. The 3'-end diol can then be oxidized allowing selective labeling of the intact 3'-end of the poly(A) tail, such as with a unique first fluorophore. In some embodiments, another label, such as a second fluorophore that specifically labels the derivative of the 5'-cap, can then be used.

In some embodiments, a label can target an intact 3'-end of an mRNA molecule, or derivative thereof, and not label a 5'-end group of an mRNA molecule modified from an intact 5'-end. In some embodiments, a label can target an intact 3'-end of an mRNA molecule, or derivative thereof, more efficiently than a 5'-end group of an mRNA molecule modified from an intact 5'-end. For example, a label can target an intact 3'-end of an mRNA molecule, or derivative thereof, at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-end group of an mRNA molecule modified from an intact 5'-end.

In some embodiments, a label can target an intact 3'-poly(A) tail of an mRNA molecule, or derivative thereof, and not label a 5'-end of an mRNA molecule treated with a TAP enzyme. In some embodiments, a label can target an intact 3'-poly(A) tail of an mRNA molecule, or derivative thereof, more efficiently than a 5'-end of an mRNA molecule treated with a TAP enzyme. For example, a label can target an intact 3'-poly(A) tail of an mRNA molecule, or derivative thereof, at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-end of an mRNA molecule treated with a TAP enzyme.

In some embodiments, a label can target an intact 3'-poly(A) tail of an mRNA molecule, or derivative thereof, and not label a 5'-end phosphate group of an mRNA molecule. In some embodiments, a label can target an intact 3'-poly(A) tail of an mRNA molecule, or derivative thereof, more efficiently than a 5'-end phosphate group of an mRNA molecule. For example, a label can target an intact 3'-poly(A) tail of an mRNA molecule, or derivative thereof, at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-end phosphate group of an mRNA molecule.

As described above, labels can be used to specifically label derivatives of intact 3'-ends that no longer contain diols. These labels may not label intact 5'-ends. To facilitate the labeling specifically towards the 3'-end, the 3'-end of the RNA molecules can be specifically modified such that the label does label the modified 3'-end and does not label an intact 5'-end. In some embodiments, another label, such as a second fluorophore that specifically labels the intact 5'-ends and/or derivatives thereof can be used.

In some embodiments, the 2' and/or 3'-hydroxyl groups of the ribose diol of the 3'-end nucleotide of an mRNA molecule can be substituted, converted, or eliminated. Accordingly, only one or no hydroxyl group would be present on the 3'-end (and thus, no diol), and the 2' and/or 3'-hydroxyl groups on the ribose of the 5'-end nucleotide can be specifically oxidized to an aldehyde or dialdehyde, such as a 2',3'-dialdehyde, using the methods described herein. The aldehyde(s) can be reacted with numerous reagents, such as fluorescent labels or molecules comprising an amine functional group, such as hydrazine-containing molecules.

In order to substitute, convert, or eliminate the 2' and/or 3'-hydroxyl groups of the 3'-end nucleotide of an mRNA molecule a number of methods can be used. For example, a nucleoside 3',5'-diphosphate can be ligated to the terminal base at the 3'-end of the mRNA using an enzyme, such as RNA ligase. As another example, a nucleotide or polynucleotide comprising a 3'-end without a 2',3'-diol functional group can be added to the nucleotide at the 3'-end of the mRNA. As another example, the mRNA or mRNA fragment having a 2',3'-diol functional group on the base at the 3'-end of its poly(A) tail can be subjected to an alkaline hydrolysis reaction.

In some embodiments, a label cannot label a 3'-poly(A) tail with a nucleoside 3',5'-diphosphate ligated to the terminal base at the 3'-end of the mRNA, such as through the use of an enzyme, and can label an intact 5'-cap of an mRNA molecule. In some embodiments, a label can target a 3'-poly(A) tail with a nucleoside 3',5'-diphosphate ligated to the terminal base at the 3'-end of the mRNA less efficiently than an intact 5'-cap of an mRNA molecule. For example, a label can target a 3',5'-diphosphate ligated to the terminal base at the 3'-end of the mRNA at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than an intact 5'-cap of an mRNA molecule.

In some embodiments, a label cannot label a 3'-poly(A) tail with a nucleoside 3',5'-diphosphate ligated to the terminal base at the 3'-end of the mRNA, such as through the use of an enzyme, and can label a derivative of an intact 5'-cap of an mRNA molecule. In some embodiments, a label can target a 3'-poly(A) tail with a nucleoside 3',5'-diphosphate ligated to the terminal base at the 3'-end of the mRNA less efficiently than a derivative of an intact 5'-cap of an mRNA molecule. For example, a label can target a 3',5'-diphosphate ligated to the terminal base at the 3'-end of the mRNA at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than a derivative of an intact 5'-cap of an mRNA molecule.

In some embodiments, a label may not label a 3'-poly(A) tail attached to a nucleotide or polynucleotide comprising a 3'-end without a 2',3'-diol functional group, and can label an intact 5'-cap of an mRNA molecule. In some embodiments, a label can target a 3'-poly(A) tail attached to a nucleotide or polynucleotide comprising a 3'-end without a 2',3'-diol functional group less efficiently than an intact 5'-cap of an mRNA molecule. For example, a label can target a 3'-poly(A) tail attached to a nucleotide or polynucleotide comprising a 3'-end without a 2',3'-diol functional group at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than an intact 5'-cap of an mRNA molecule.

In some embodiments, a label may not label a 3'-poly(A) tail attached to a nucleotide or polynucleotide comprising a 3'-end without a 2',3'-diol functional group, and can label a derivative of an intact 5'-cap of an mRNA molecule. In some embodiments, a label can target a 3'-poly(A) tail attached to a nucleotide or polynucleotide comprising a 3'-end without a 2',3'-diol functional group less efficiently than a derivative of an intact 5'-cap of an mRNA molecule. For example, a label can target a 3'-poly(A) tail attached to a nucleotide or polynucleotide comprising a 3'-end without a 2',3'-diol functional group at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than a derivative of an intact 5'-cap of an mRNA molecule.

In some embodiments, a label may not label a 3'-poly(A) tail that has undergone an alkaline hydrolysis reaction and can label an intact 5'-cap of an mRNA molecule. In some embodiments, a label can target a 3'-poly(A) tail that has undergone an alkaline hydrolysis reaction less efficiently than an intact 5'-cap of an mRNA molecule. For example, a label can target a 3'-poly(A) tail that has undergone an alkaline hydrolysis reaction at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than an intact 5'-cap of an mRNA molecule.

In some embodiments, a label may not label a 3'-poly(A) tail that has undergone an alkaline hydrolysis reaction and can label a derivative of an intact 5'-cap of an mRNA molecule. In some embodiments, a label can target a 3'-poly(A) tail that has undergone an alkaline hydrolysis reaction less efficiently than a derivative of an intact 5'-cap of an mRNA molecule. For example, a label can target a 3'-poly(A) tail that has undergone an alkaline hydrolysis reaction at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than a derivative of an intact 5'-cap of an mRNA molecule.

In some embodiments, a label can target a 3'-poly(A) tail of an mRNA molecule and not label a 5'-cap of an mRNA molecule with a blocking group. In some embodiments, a label can target a 3'-poly(A) tail of an mRNA molecule more efficiently than a 5'-cap of an mRNA molecule with a blocking group. For example, a label can target a 3'-poly(A) tail of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-cap of an mRNA molecule with a blocking group. For example, a label can target a derivative of an intact 3'-poly(A) tail of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-cap of an mRNA molecule with a blocking group. For example, a label can target a derivative of an intact 3'-poly(A) tail of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a derivative of an intact 5'-cap of an mRNA molecule with a blocking group.

In some embodiments, a label can target a 3'-poly(A) tail of an mRNA molecule and not label a 5'-end phosphate group of an mRNA molecule with a blocking group. In some embodiments, a label can target a 3'-poly(A) tail of an mRNA molecule more efficiently than a 5'-end phosphate group of an mRNA molecule with a blocking group. For example, a label can target a 3'-poly(A) tail of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-end phosphate group of an mRNA molecule with a blocking group. For example, a label can target a derivative of a 3'-poly(A) tail of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-end phosphate group of an mRNA molecule with a blocking group.

In some embodiments, a label can target a 3'-poly(A) tail of an mRNA molecule and not label a 5'-adenylated end of an mRNA molecule with a blocking group. In some embodiments, a label can target a 3'-poly(A) tail of an mRNA molecule with a blocking group more efficiently than a 5'-adenylated end of an mRNA molecule with a blocking group. For example, a label can target a 3'-poly(A) tail of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times more efficiently than a 5'-adenylated end of an mRNA molecule with a blocking group. For example, a label can target a derivative of a 3'-poly(A) tail of an mRNA molecule at least about 2, 3, 4, 5, 6, 7, 8, 9, 10, 15, 20, 30, 40, 50, 60, 70, 80, 90, 100, 500, 1000, 5000, $10^4$, $10^5$, or $10^6$ times less efficiently than a 5'-adenylated end with a blocking group.

In other cases, to facilitate the labeling specifically towards the 5'-end, the 3'-end of the RNA molecules can be specifically modified such that the label does label the 5'-end and does not label the modified 3'-end.

5'-End Cap and 3'-Poly(A) Tail Structures

All intact or non-degraded mRNA generally possess two common sites, the 3'-poly(A) tail and the 5'-end cap sequence, in which the terminal ribose present on both ends comprise diol moieties (FIG. 9). In an mRNA molecule, only the two ends (5'-with a cap structure and 3'-with the last sugar 2',3'-OH) have these diols. The 5'-CAP structure can comprise an altered nucleotide on the 5'-end of RNA, for example, precursor messenger RNA and some other primary RNA transcripts. The 5'-capping process is generally vital for creation of mature messenger RNA, which can undergo translation. Capping can maintain the stability of the RNA while it undergoes translation. The 5'-cap structure can provide significant resistance to 5'-exonuclease activity and its absence can result in rapid degradation of the mRNA (e.g., see Mol. Biol. Med. 5: 1-14, 1988; Cell 32: 681-694, 1983). In some embodiments, the 5'-cap resembles the 3'-end of an RNA molecule because the 5'-carbon of the cap ribose can be bonded, and the 3'-carbon of the cap can be unbonded. The 5'-cap structure can prevent 5'-degradation in two ways. First, degradation of the mRNA by 5'-exonucleases can be prevented by functionally resembling a 3'-end. Second, protein complexes, such as the CAP Binding Complex (CBC) and/or the eukaryotic translation initiation factors eIF-4E and eIF-4G, associated with the 5'-cap structure can block the access of decapping enzymes to the cap. This can increase the half-life of the mRNA. The Cap Binding Complex (CBC) can comprises the 20 kD (CBP20) subunit and the 80 kD (CBP80) subunit. However, the 5'-cap may not provide protection from degradation by certain enzymes, such as RNAses.

Typically, the 5'-cap is found on the 5'-end of an mRNA molecule and comprises a 7-methylguanosine nucleotide linked to the 5'-nucleoside of the mRNA chain via an inverted 5'- to 5'-triphosphate linkage (FIG. 10). The phosphates of the cap are linked through phosphoanhydride bonds, which differ from the phosphodiester linkage between adjacent nucleosides of the RNA chain. This guanosine can be methylated on the 7 position directly after capping by any suitable enzyme, such as a methyl transferase, and can be referred to as a 7-methylguanylate cap ($m^7G$). Other modifications can include methylation of the 2' hydroxy-groups of the first 2 ribose sugars of the 5'-end of the mRNA. 5'-cap structures can include type 0 (m7G5'ppp5'X), type 1 (m7G5'ppp5'XmY), and type 2 (m7G5'ppp5'XmYmZ), differing in the number of 2'-O-methylated penultimate nucleotides. In some embodiments, the guanosine is methylated in the 2 and 7 positions. In some embodiments, the guanosine is trimethylated in the 2, 7 and 7 positions. As stated above, the sugar (ribose) of this specific nucleotide has a 2',3'-cis-diol functional group.

In vivo, capping of a 5'-triphosphorylated primary mRNA transcript occurs via several enzymatic steps (e.g., see Martin, S A et al., J. Biol. Chem. 250: 9322, 1975; Myette, J. R and Niles, E G, J. Biol. Chem. 271: 11936, 1996; M A Higman, et al., J. Biol. Chem. 267: 16430, 1992). The 5'-cap can be formed on nascent RNA chains by the sequential action of RNA triphosphatase, RNA guanylyltransferase, and RNA (guanine N7) methyltransferase. RNA triphosphatase can hydrolyze the gamma phosphate of triphosphate-terminated RNA to produce a diphosphate end and inorganic phosphate. RNA guanylyltransferase can catalyze a reversible two-step nucleotidyl transfer reaction. The enzyme and alpha phosphorus of GTP form a covalent enzyme-guanylate intermediate and releasing pyrophosphate. The enzyme can transfer the GMP to the 5'-diphosphate RNA end to form a G cap. RNA (guanine N7) methyltransferase can transfer the methyl group from S-adenosylmethionine (AdoMet) to the cap guanine to form an m7G cap releasing S-adenosylhomocysteine (AdoHcy).

In some embodiments, a capping enzyme, such as those mentioned herein, can be a facilitating agent for labeling. In some embodiments, labeling of the 5'-cap can be facilitated by RNA triphosphatase and RNA guanyltransferase enzymatic activities, and optionally, RNA guanine-7-methyltransferase enzymatic activity. Enzymes that can be used for capping of the 5'-end of mRNA of the present invention are well known in the art (e.g., see Shuman, S, Prog. Nucleic Acid Res. Mol. Biol. 66: 1-40, 2001; Shuman, S, Prog. Nucleic Acid Res. Mol. Biol. 50: 101-129, 1995; Bisaillon, M and Lemay, G, Virology 236: 1-7, 1997; Banerjee, A K, Microbiol. Rev. 44: 175-205, 1980). The active sites for the RNA triphosphatase, RNA guanyltransferase and guanine-7-methyltransferase enzymatic activities can be on single-component polypeptides, 2-component polypeptides (typically having RNA triphosphatase and RNA guanyltransferase activities), or on a 3-component polypeptide, from a cloned, recombinant or wild-type source. Genes encoding RNA triphosphatase, RNA guanyltransferase and guanine-7-methyltransferase from one source can complement deletions in one or all of these genes from another source. Thus, the capping enzymes can originate from one wild type source, or one or more of the RNA triphosphatase, RNA guanyltransferase, and/or guanine-7-methyltransferase activities can comprise a polypeptide from a different source, which polypeptides can each be encoded by a DNA sequence originating from the same biological source or by a DNA sequence originating from a different biological source.

RNA that results from the action of the RNA triphosphatase and the RNA guanyltransferase enzymatic activities, as well as RNA that is additionally methylated by the guanine-7-methyltransferase enzymatic activity, can be referred to as "5'-capped RNA" or "capped RNA", and the combination of one or more polypeptides having the enzymatic activities that result in "capped RNA" can be referred to as "capping enzyme systems" or, more simply, as "capping enzymes" herein. Capping enzyme systems, including cloned forms of such enzymes, have been identified and purified from many sources and are well known in the art (e.g., see Shuman, S, Prog. Nucleic Acid Res. Mol. Biol. 66: 1-40, 2001; Shuman, S, Prog. Nucleic Acid Res. Mol. Biol. 50: 101-129, 1995; and Banerjee, A K, Microbiol. Rev. 44: 175, 1980).

In some cases, the starting point for the capping process can be the unaltered 5'-end of a nucleotide molecule, such as an RNA molecule, which comprises a 5'-end nucleotide followed by three phosphate groups attached to the 5'-carbon. One of the terminal phosphate groups can be removed by any suitable enzyme, such as RNA terminal phosphatase, leaving two terminal phosphates. GTP can then be added to the terminal phosphates, by any suitable enzyme, such as a guanylyl transferase, losing two phosphate groups (from the GTP) in the process. This can result in the 5'- to 5'-triphosphate linkage. The 7-nitrogen of guanine can then be methylated by any suitable enzyme, such as a methyl transferase. In some embodiments, if the second base from the terminal is adenine, it can be methylated. In some embodiments, the third base from the terminus can be methylated.

Removal of the cap structure is catalyzed in vivo by a decapping holoenzyme composed of the catalytic Dcp2 subunit and the coactivator Dcp1, which can compete with eIF-4E to bind the cap. Decapping is regulated by decapping activators and inhibitors. In some embodiments, decapping of the 5'-cap can be catalyzed by a decapping complex made up of at least Dcp1 and Dcp2. In some embodiments, a decapping enzyme, such as those mentioned herein, can be a facilitating agent for labeling.

In some embodiments, pyrophosphatase, such as Tobacco Acid Pyrophoshatase (TAP) can be used to decap 5'-end caps from mRNA. In some embodiments, a pyrophosphatase, such as TAP, can be a facilitating agent for labeling. TAP hydrolyzes various pyrophosphate bonds, including those in adenosine triphosphate (ATP), cyclic nucleotides, and dinucleotides, but not those in RNA or DNA. TAP cleaves the pyrophosphate bond of the 5'-terminal methylated guanine nucleotide cap of eukaryotic messenger RNAs. TAP hydrolyzes the phosphoric acid anhydride bonds in the triphosphate bridge of the 5'-end cap structure, releasing the cap nucleoside and generating a 5'-phosphorylated terminus on a RNA molecule. Complete hydrolysis results in removal of the β- and γ-phosphates, leaving only the α-phosphate attached. In some embodiments, the resulting 5'-monophosphorylated terminus can be ligated to a 3'-hydroxylated terminus using T4 RNA Ligase or dephosphorylated with a phosphatase, such as an alkaline phosphatase for end labeling. In some embodiments, a ligase, such as T4 ligase, can be a facilitating agent for labeling. In some embodiments, a phosphatase, such as an alkaline phosphatase, can be a facilitating agent for labeling.

The resulting decapped 5'-phosphohorylated RNA can then be further manipulated. For example, intramolecular ligation using RNA Ligase of a viral genomic RNA after treatment with TAP can be used to determine the nucleic acid sequence of the 5' and 3' termini. Procedures involving ligation of oligoribonucleotides to TAP-treated RNAs followed by amplification of the ligated product can be used for mapping the 5'-termini of mRNAs. Removal of the cap structure using TAP can also allow for the RNA to be 5'-end labeled for sequencing or for use as a hybridization probe, for example, a TAP-treated RNA can be dephosphorylated with an alkaline phosphatase and then labeled using T4 Polynucleotide Kinase (PNK) and nucleotide with a label, such as a fluorescent or radioactive label. In some embodiments, a kinase, such as PNK, can be a facilitating agent for labeling.

In some embodiments, the uncapped RNA is a primary RNA transcript, meaning an RNA having a 5'-triphosphate group from an in vivo or an in vitro source. In some embodiments, the uncapped RNA is RNA having a 5'-diphosphate group rather than a primary RNA transcript having a 5'-triphosphate group. In some embodiments, the uncapped RNA comprising primary RNA transcripts or RNA having a 5'-diphosphate group lacks a poly(A) tail on the 3'-terminus. In some embodiments, the uncapped RNA comprising primary RNA transcripts or RNA having a 5'-diphosphate group comprises a poly(A) tail on the 3'-terminus.

In some embodiments, an intact mRNA molecule can only carry a 5'-label and not a 3'-label. In some embodiments, an intact mRNA molecule can only carry a 3'-label and not a 5'-label. Various other combinations of labels in degraded mRNA molecules would indicate lack of the correct chemistries at the ends of an intact mRNA molecule.

In some embodiments, the 5'-end or the 3'-end can be selectively labeled with a detectable label. For example, to label the 3'-end, the method can comprise enzymatically removing the 5'-cap followed by modification of the 3'-ribose diol allowing selective labeling of the 3'-end with a unique label, such as a fluorophore.

The 3'-poly(A) tail comprises multiple adenosine monophosphates. The poly(A) tail of mRNA is typically added to mRNA by polyadenylation. Polyadenylation can be the covalent linkage of one or more polyadenylyl moieties to an mRNA molecule. The poly(A) tail and the protein bound to it can help protect mRNA from degradation by exonucleases. However, the poly(A) tail may not protect mRNA from degradation by enzymes such as RNAses. Polyadenylation is also important for transcription termination, export of the mRNA from the nucleus, and translation.

Polyadenylation typically occurs during and immediately after transcription, where the mRNA chain is cleaved through the action of an endonuclease complex associated with RNA polymerase. After the cleavage of the mRNA, numerous adenosine residues are added to the free 3'-end at the cleavage site. This reaction can be catalyzed by polyadenylate polymerase.

Agents/Labels/Reporting Molecules

In various embodiments of the invention, target polynucleotides, such as mRNA can be labeled with labels, or reporter molecules. Labeling chemistry can use any suitable methods known in the art. Methods of labeling and labels suitable for labeling the intact 5' and 3'-ends are described herein. Enzymes that modify the 5'-ends of RNA are useful tools for characterizing and manipulating RNA molecules. For example, alkaline phosphatase (AP), such as APEX® alkaline phosphatase (EPICENTRE), shrimp alkaline phosphatase (USB, Cleveland, Ohio), or Arctic alkaline phosphatase (New England Biolabs, MA) converts the 5'-triphosphates of uncapped primary RNA and the 5'-monophosphates of RNA to 5'-hydroxyl groups, generating RNAs that have a 5'-hydroxyl group, but does not affect capped RNA. Nucleic acid pyrophosphatases (PPase), such as TAP, cleave the triphosphate groups of both capped and uncapped RNAs to synthesize RNAs that have a 5'-monophosphate group. A decapping enzyme, such as a yeast decapping enzyme, mammalian decapping enzyme, *Arabidopsis thaliana* decapping enzyme, or vaccinia virus decapping enzymes D9 or D10, can convert capped RNA to RNA that has a 5'-monophosphate group. A capping enzyme, such as SCRIPTCAP® capping enzyme, EPICENTRE, poxvirus capping enzyme, vaccinia virus capping enzyme, or *Saccharomyces cerevisiae* capping enzyme RNA triphosphatase, can convert RNA that has a 5'-triphosphate group or RNA that has a 5'-diphosphate group to capped RNA. Polynucleotide kinases (PNK), such as T4 PNK, can monophosphorylate hydroxyl groups on the 5'-ends of RNA molecules and remove monophosphate groups on the 3'-ends of RNA molecules, such as 3'-monophosphates generated by RNase A. In addition, 5'-exoribonucleases (XRN), such as *Saccharomyces cerevisiae* Xrn I exoribonuclease, can digest 5'-monophosphorylated RNA to mononucleotides, but generally does not digest RNA that has a 5'-triphosphate, 5'-cap, or 5'-hydroxyl group.

RNA ligase can also be used to facilitate labeling of intact end groups. This enzyme catalyzes phosphodiester bond formation specifically between a 5'-monophosphate in a donor RNA and a 3'-hydroxyl group in an acceptor oligonucleotide, such as an RNA acceptor oligonucleotide. Thus, RNAs that have a monophosphate group on their 5'-ends can be donor substrates for ligation to an acceptor nucleic acid that has a 3'-hydroxyl group using RNA ligase. RNA molecules that contain triphosphate, diphosphate, hydroxyl or capped 5'-end groups do not function as donor molecules for RNA ligases, such as T4 RNA ligase, EPICENTRE, or bacteriophage TS2126 RNA ligase. Thus, RNAs that have a hydroxyl group on their 5'-ends, whether present in a sample or obtained by treatment with AP, cannot serve as donor substrates for RNA ligase. Similarly, RNA molecules that contain a 3'-terminal blocked group, such as RNA molecules that have a 3'-phosphate group or a 3'-beta-methoxyphenylphosphate group, do not function as acceptor substrates for RNA ligase.

Other publications disclose use of alkaline phosphatase (AP), tobacco acid pyrophosphatase (TAP), and RNA ligase to manipulate m7G-capped eukaryotic mRNAs using oligo capping methods. For example, oligo capping methods and their use are disclosed in: World Patent Applications WO0104286; and WO 2007/117039 A1; U.S. Pat. No. 5,597,713; Suzuki, Y et al., Gene 200: 149-156, 1997; Suzuki, Y and Sugano, S, Methods in Molecular Biology, 175: 143-153, 2001, ed. by Starkey, M P and Elaswarapu, R, Humana Press, Totowa, N.J.; Fromont-Racine, M et al., Nucleic Acids Res. 21: 1683-4, 1993; and in Maruyama, K and Sugano, S, Gene 138: 171-174, 1994. In these methods, total eukaryotic RNA or isolated polyadenylated RNA is first treated with AP and then the AP is inactivated or removed. The AP converts RNA that has a 5'-triphosphate, such as an uncapped primary RNA, and RNA that has a 5'-monophosphate, to RNA that has a 5'-hydroxyl. The sample is then treated with TAP, which converts the 5'-capped eukaryotic mRNA to mRNA that has a 5'-monophosphate. The resulting 5'-monophosphorylated mRNA can then be ligated to an acceptor oligonucleotide using RNA ligase. The resulting mRNA can serve as a template for synthesis of first-strand cDNA that has a tag joined to its 3'-end. Then, double-stranded cDNA can be made using a second-strand cDNA synthesis primer that is complementary to the tag joined to the 3'-end of the first-strand cDNA.

Different reactions are described in the literature to modify diol groups within RNA in a chemical reaction (Proudnikov D. and Mirzabekov A. Nucleic Acid Res. 22, 4535-4542 (1996) and reference cited therein). For example, the diol group in RNA can be converted into dialdehyde groups by oxidation (Czworkowski J et al., Biochemistry 30(19):4821-30 (1991); Odom 0 W Jr et al., Biochemistry 19(26):5947-54 (1980)). Periodate-mediated oxidation of vicinal diol groups provides one of the few methods to selectively modify the 3'-terminal ribose in RNA molecules. Thereafter, periodate oxidized ribonucleotides can be subsequently converted to fluorescent nucleic acid molecules by reaction with fluorescent hydrazines, hydroxylamines and amines (Hileman R E et al., Bioconjug Chem, 5(5):436-44 (1994)]. In some cases, the dialdehyde groups in periodate-oxidized ribonucleotides can be used to introduce a label in a second chemical reaction, such as with a hydrazine group. Reaction conditions for the modification of diol groups within RNA in a chemical reaction are disclosed in U.S. Pat. Nos. 5,962,272 and 6,022,715. In some cases, the labeling reaction is performed directly on a sample containing RNA. In a different embodiment, the labeling reaction is performed on modified RNA. In another embodiment, the labeling reaction is performed on RNA immobilized on a solid support. In another embodiment, the labeling reaction is performed on RNA that is not immobilized on a solid support.

In some cases, sodium periodate and/or lead tetraacetate can be used in solution to open saccharide rings between vicinal diols of intact mRNA ends, leaving two aldehyde groups. Because the process requires vicinal diols, periodate oxidation can be used to selectively label the intact ends of mRNA containing vicinal diols instead of ends of cleaved mRNA that do not have vicinal diols. Thus, the cis-diols on the 5'- and/or 3'-terminal ribose of RNA can be cleaved to generate aldehydes by periodate oxidation and then be covalently linked with any amine-containing dye, such as dye-hydrazides, carbazides, hydroxylamines, cadaverines, ethylenediamines and glycine moieties (Hansske F, Cramer F. Methods Enzymol. 1979; 59:172-81, and Wu T P, Ruan K C, Liu W Y. Nucleic Acids Res. 1996 Sep. 1; 24(17):3472-3). For example, the 3'- and/or 5'-terminus of RNA can be oxidized, selectively or non-selectively as described above, into dialdehyde(s) by reacting with sodium periodate and can then be labeled with fluorescein-5-thiosemicarbazide through the condensation reaction between carbazide and aldehyde. Fluorescent labels with an attached hydrazine group can be efficiently coupled with an aldehyde group and hydrazine bonds can be stabilized by reduction with sodium cyanoborohydride. Alternatively, ethylenediamine can be used. The aldimine bond between the aldehyde group in oxidized RNA and ethylenediamine can be stabilized by reduction with sodium cyanoborohydride and the primary amine group introduced at these sites can be used for attachment of isothiocyanate or succinimide derivatives of fluorescent dyes. Fluorescent labeling can be carried out in solution or on a reverse phase column.

In some cases, the 5'-end of mRNA with an intact 5'-end cap structure can be labeled by covalent attachment of a probe. For example, RNA can be treated with a phosphatase, such as calf intestinal phosphatase (CIP). The phosphatase removes the 5'-phosphate from partial mRNA transcripts. Because the phosphatase does not affect the capped mRNA, after treatment of the phosphatase treated mRNA with a pyrophosphatase to remove the cap, such as TAP as described above, the only mRNA molecules in the sample with an exposed 5'-phosphate are those which contained an intact 5-end cap prior to treatment of the sample with the phosphatase and pyrophosphatase. In some embodiments, the label is attached to the RNA covalently. For example, labels can be covalently attached via an exposed 5'-phosphate, such as by carboiimide activation of the 5'-phosphate and attachment with amine-terminated dye or biotin. In some embodiments, the label is attached to the RNA non-covalently. For example, the label can be attached to the RNA through hydrogen bonds, ionic bonds, van der Waals forces, and/or hydrophobic interactions.

In some embodiments, the label is not a sequence specific label. For example, a label can be attached to an mRNA end irrespective of the base of the nucleotide comprising a ribose with a diol moiety and/or the identity or sequence of bases upstream or downstream of the end being labeled. For example, a label can be attached to an mRNA end with an adenosine, uracil, cytosine, thymidine, or guanine base comprising a ribose diol nonspecifically.

The label is most preferably a fluorescent dye. Fluorescent dyes can be detected in droplets in real time with high resolution, and the availability of many fluorescent dyes with distinct excitation and emission wavelengths allow monitoring many labels in one experiment. Preferably, sets of fluorescent dyes are selected so as to allow for a simultaneous detection of more than one dye in the same reaction. A set of dyes that can be detected at the same time include, but are not limited to, Cy3, Cy5, FAM, JOE, TAMRA, ROX, dR110, dR6G, dTAMRA, dROX, or any mixture thereof (refer to Table 2 below for details on those dyes). Any of those dyes can be used individually or in any combination to practice the present invention. More preferably, a dye should allow for single molecule detection. Examples for the use of fluorescence methods in single molecule detection have been described by Joo C et al., Annu Rev. Biochem. 77, 51-76 (2008). A large number of fluorescent dyes has been synthesized, and are commercially available in different formats. This includes fluorescent dyes having a linker region and a hydrazine group that allows for coupling to RNA in a reaction with dialdehyde groups. For examples on such compounds refer to the catalog of Invitrogen. The present invention is not limited to the use of a specific fluorescent dye, but different dyes can be applied to the same effect. The linker region can consist of a carbon backbone, can contain sulfur atoms, ketone groups, or diethylene glycol groups, or dodecaethylene glycol groups. The length of the linker can vary where the backbone is a linear molecule of 1 to 20 atoms. A linker can contain groups of atoms that allow for selective removal of the label in a chemical reaction as, for example, disclosed in PCT Patent Publication No. WO2003/048387.

Non-limiting examples of labels that can be used include 5-FAM (also called 5-carboxyfluorescein; also called Spiro (isobenzofuran-1(3H), 9'-(9H)xanthene)-5-carboxylic acid, 3',6'-dihydroxy-3-oxo-6-carboxyfluorescein); 5-Hexachloro-Fluorescein; ([4,7,2',4',5',7'-hexachloro-(3',6'-dipivaloyl-fluoresceinyl)-6-carboxyli-c acid]); 6-Hexachloro-Fluorescein; ([4,7,2',4',5',7'-hexachloro-(3',6'-dipivaloylfluoresceinyl)-5-carboxylic acid]); 5-Tetrachloro-Fluorescein; ([4,7,2',7'-tetra-chloro-(3',6'-dipivaloylfluoresceinyl)-5-carboxylic acid]); 6-Tetrachloro-Fluorescein; ([4,7,2',7'-tetrachloro-(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyeamino)naphthalene-1-sulfonic acid); 1,5-IAEDANS (5-((((2-iodoacetyeamino)ethyeamino)naphthalene-1-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-pr-oprionic acid); Quasar®-670 dye (Biosearch Technologies); Cal Fluor® Orange dye (Biosearch Technologies); Rox dyes; Max dyes (Integrated DNA Technologies), tetrachlorofluorescin (TET), 4,7,2'-trichloro-7'-phenyl-6-carboxyfluorescein (VIC), HEX, Cy3, Cy 3.5, Cy 5, Cy 5.5, Cy 7, tetramethylrhodamine, ROX, and JOE as well as suitable derivatives thereof. The label can be an Alexa Fluor dye, such as Alexa Fluor 350, 405, 430, 488, 532, 546, 555, 568, 594, 633, 647, 660, 680, 700, and 750. The label can be Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X. The label can be at the 5'-end of a probe, 3'-end of the probe, at both the 5'- and 3'-end of a probe, or internal to the probe. A unique label can be used to detect each different locus in an experiment, for example two termini of a target polynucleotide, such as mRNA.

Non-limiting examples of dye-hydrazides that can be used for labeling include Alexa Fluor®-hydrazides and salts thereof, 1-pyrenebutanoic acid-hydrazide, 7-diethylaminocoumarin-3-carboxylic acid-hydrazide (DCCH) Cascade Blue® hydrazides and salts thereof, biocytin-hydrazide, 2-acetamido-4-mercaptobutanoic acid-hydrazide (AMBH), BODIPY® FL-hydrazide, biotin-hydrazide, Texas Red®-hydrazide, biocytin-hydrazide, luminol (3-aminophthalhydrazide), and Marina Blue® hydrazide. Non-limiting examples of dye-ethylenediamines that can be used for labeling include 5-dimethylaminonaphthalene-1-(N-(2-aminoethyl))sulfonamide (dansyl ethylenediamine), Cascade Blue® ethylenediamine and salts thereof, N-(2-aminoethyl)-4-amino-3,6-disulfo-1,8-naphthalimide (lucifer yellow ethylenediamine) and salts thereof, N-(biotinoyl)-N'-(iodoacetyl) ethylenediamine, N-(2-aminoethyl)biotinamide, hydrobromide (biotin ethylenediamine), 4,4-difluoro-5,7-dimethyl-4-bora-3a,4a-diaza-s-indacene-3-propionyl ethylenediamine and salts thereof (BODIPY® FL EDA), Lissamine™ rhodamine B ethylenediamine, and DSB-X™ biotin ethylenediamine (desthiobiotin-X ethylenediamine, hydrochloride).

Non-limiting examples of dye-cadaverines that can be used for labeling include 5-dimethylaminonaphthalene-1-(N-(5-aminopentyl))sulfonamide (dansyl cadaverine), 5-(and-6)-((N-(5 aminopentyl)amino) carbonyl)tetramethylrhodamine (tetramethylrhodamine cadaverine), N-(5-aminopentyl)-4-amino-3,6-disulfo-1,8-naphthalimide and salts thereof (lucifer yellow cadaverine), N-(5-aminopentyl)biotinamide and salts thereof (biotin cadaverine), biotin-X cadaverine (5-(((N-(biotinoyl)amino) hexanoyl)amino) pentylamine and salts thereof, Texas Red® cadaverine (Texas Red® C5), 5-(((4-(4, 4-difluoro-5-(2-thienyl)-4-bora-3a,4a-diaza-s-indacene-3-yl)phenoxy)acetyl)amino) pentylamine and salts thereof (BODIPY® TR cadaverine), Oregon Green® cadaverine, Alexa Fluor® cadaverine, and 5-((5-aminopentyl)thioureidyl)fluorescein and salts thereof (fluorescein cadaverine).

In some embodiments, a label can comprise an antibody specific to the intact 5'-cap. The antibody can be attached to a dye or reporter molecule to allow detection of the antibody bound to the intact 5'-cap structure. The 5'-cap antibody can be a Tri-Methyl Guanosine Cap (3mG Cap) Antibody or an anti-7-methylguanosine antibody.

Sample Partitioning

After labeling of the ends of target nucleic acids in a sample using any of the methods described herein, the sample containing the labeled and/or unlabeled nucleotides can be separated into a plurality of spatially isolated partitions, such as droplets.

A partition can be a separated portion of a bulk volume. A partition can be a sample partition (or a reagent partition) generated from a sample (or a reagent) included in the bulk volume. Partitions generated from a bulk volume can be substantially uniform in size or can have distinct sizes (e.g., sets of partitions of two or more discrete, uniform sizes). Partitions can be liquid partitions, which are partitions that have a liquid periphery and/or are at least predominantly, by volume, a liquid phase. Exemplary liquid partitions are droplets or slugs A droplet can be a small volume of a first liquid that is encapsulated by an immiscible second liquid, such as a continuous phase of an emulsion (and/or by a larger droplet). The volume of a droplet, and/or the average volume of droplets in an emulsion, can, for example, be less than about one microliter (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) can have a diameter (or an average diameter) of less than about 1000, 100, or 10 micrometers, or about 1000 to 10 micrometers, among others. A droplet can be spherical or nonspherical. A droplet can be a simple droplet or a compound droplet.

In a preferred embodiment, the spatially isolated partitions are droplets within an emulsion. Any of the systems, methods, apparatuses, compositions, or kits, as described in U.S. application Ser. No. 12/862,542 can be used for generating spatially isolated partitions within an emulsion or for mixing small volumes of fluid by coalescence of multiple emulsions. Any of the systems, methods, apparatuses, or compositions, as described in U.S. application. Ser. Nos. 12/962,502, 12/962,507, 12/963,523, and 12/962,511 can be used for generating spatially isolated partitions within an emulsion, for transporting droplets, or for performing droplet-based assays. FIGS. 15 A and B display droplet formation as a droplet is pinched by inflow of oil from the sides and stretching/necking down as the droplet pulls away from the bulk fluid, respectively.

The present disclosure includes compositions and methods using droplet digital PCR. The droplets described herein can include emulsion compositions (or mixtures of two or more immiscible fluids) described in U.S. Pat. No. 7,622,280, and droplets generated by devices described in International Application No. PCT/US2009/005317, filed Sep. 23, 2009. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Splitting a sample into small reaction volumes as described herein can enable the use of reduced amounts of reagents, thereby lowering the material cost of the analysis. Reducing sample complexity by partitioning also improves the dynamic range of detection because higher-abundance molecules are separated from low-abundance molecules in different compartments, thereby allowing lower-abundance molecules greater proportional access to reaction reagents, which in turn enhances the detection of lower-abundance molecules.

Droplets can be generated having an average diameter of about, less than about, or more than about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of said droplets does not vary by more than plus or minus 5% of the average size of said droplets. In some cases, the droplets are generated such that the size of said droplets does not vary by more than plus or minus 2% of the average size of said droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in a fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing a PCR reaction, including nucleotides, primers, probe(s) for fluorescent detection, template nucleic acids, DNA polymerase enzyme, and optionally, reverse transcriptase enzyme. The aqueous phase can comprise one or more buffers and/or additives described herein.

The oil phase can comprise a fluorinated base oil which can be additionally stabilized by combination with a fluorinated surfactant such as a perfluorinated polyether. In some cases, the base oil can be one or more of HFE 7500, FC-40, FC-43, FC-70, or another common fluorinated oil. In some cases, the anionic surfactant is Ammonium Krytox (Krytox-AM), the ammonium salt of Krytox FSH, or morpholino derivative of Krytox-FSH. Krytox-AS can be present at a concentration of about, more than about, or less than about 0.1%, 0.2%, 0.3%, 0.4%, 0.5%, 0.6%, 0.7%, 0.8%, 0.9%, 1.0%, 2.0%, 3.0%, or 4.0% w/w. In some preferred embodiments, the concentration of Krytox-AS is 1.8%. In other preferred embodiments, the concentration of Krytox-AS is 1.62%. Morpholino derivative of Krytox-FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% w/w. The concentration of morpholino derivative of Krytox-FSH can be about 1.8%. The concentration of morpholino derivative of Krytox-FSH can be about 1.62%.

The oil phase can further comprise an additive for tuning the oil properties, such as vapor pressure or viscosity or surface tension. Non-limiting examples include perfluorooctanol and 1H,1H,2H,2H-Perfluorodecanol. 1H,1H,2H,2H-Perfluorodecanol can be added to a concentration of about, more than about, or less than about 0.05%, 0.06%, 0.07%, 0.08%, 0.09%, 1.00%, 1.25%, 1.50%, 1.75%, 2.00%, 2.25%, 2.50%, 2.75%, or 3.00% w/w. 1H,1H,2H,2H-Perfluorodecanol can be added to a concentration of about 0.18% w/w.

The emulsion can be formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50, 60, 70, 80, 90, or 95 degrees Celsius. In some cases this heating occurs using a thermocycler. During the heating process, a fluid or mineral oil overlay can be used to prevent evaporation. Excess continuous phase oil can or may not be removed prior to heating. The biocompatible capsules can be resistant to coalescence and/or flocculation across a wide range of thermal and mechanical processing.

Following conversion, the capsules can be stored at about, more than about, or less than about 3, 4, 5, 6, 7, 8, 9, 10, 15, 20, 25, 30, 35, or 40 degrees Celsius. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

In some embodiments, the emulsions or droplets can be encapsulated by a skin and/or can be stabilized. In some embodiments, the droplets may not be encapsulated by a skin. The skin-encapsulated droplets, or capsules, can be resistant to coalescence, aggregation, and breakage over a wide range of thermal and mechanical processing conditions. Any of the systems, methods, apparatuses, compositions, and kits, as described in U.S. application Ser. Nos. 12/976,827 and 12/976,816, can be used for making and using a stabilized emulsion.

The capsules can contain one or more polynucleotides and can resist coalescence, particularly at high temperatures. Accordingly, PCR amplification reactions can occur at a very high density (e.g., number of reactions per unit volume). In some cases, greater than about 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a PCR reaction to occur, e.g., primers, probes, dNTPs, DNA or RNA polymerases, etc. These capsules exhibit resistance to coalescence and flocculation across a wide range of thermal and mechanical processing.

The plurality of spatially isolated partitions of the sample containing the labeled and/or unlabeled nucleotides can be generated such that the nucleic acid is present at an average concentration of not greater than about 5 copies per partition or droplet. For example, the plurality of spatially isolated partitions of the sample containing the labeled and/or unlabeled nucleotides can be generated such that the nucleic acid is present at an average concentration of 1, 2, 3, 4, or 5 copies per partition or droplet.

In some embodiments, the sample containing the labeled and/or unlabeled nucleotides can be separated into a plurality of spatially isolated partitions randomly. For example, the sample containing the labeled and/or unlabeled nucleotides can be separated into a plurality of spatially isolated partitions such that each partition can contain an average concentration of not greater than about 5 copies of any nucleic acid present in the sample per partition or droplet.

In some embodiments, the sample containing the labeled and/or unlabeled nucleotides can be separated into a plurality of spatially isolated partitions such that the separating is independent of the size of the nucleic acid. For example, a first nucleotide of one size can be separated into a spatially isolated partition at substantially the same ratio as a second nucleotide of a size smaller or longer than the first nucleotide is separated into another spatially isolated partition. As another example, a sample containing labeled and/or unlabeled nucleotides of various sizes or lengths can be separated into a plurality of spatially isolated partitions such that the various sized nucleotides are distributed throughout the partitions substantially equally independent of the size of the nucleotides being separated.

In some embodiments, the sample containing the labeled and/or unlabeled nucleotides can be separated into a plurality of spatially isolated partitions such that the separating is independent of the labeling present on the nucleic acid. For example, a sample containing a 5'-labeled nucleotide, a 3'-labeled nucleotide, a 5'- and 3'-labeled nucleotide, and an unlabeled nucleotide can be separated can be separated into a plurality of spatially isolated partitions such that each of the 5'-labeled nucleotide, 3'-labeled nucleotide, 5'- and 3'-labeled nucleotide, and unlabeled nucleotide are separated into partitions at substantially the same ratio at which each of the various nucleotides are present in the sample before separating. For example, the label present on the nucleic acids in the sample do not substantially affect the partitioning rate at which each of the variously labeled nucleotides are separated into partitions.

Target Polynucleotides

In various embodiments of the invention, nucleic acids are used as substrates for further manipulation. A nucleic acid can be derived from a sample. A sample can be a compound, composition, and/or mixture of interest, from any suitable source(s). A sample is the general subject of interest for a test that analyzes an aspect of the sample, such as an aspect related to one or more labels analyte that can be present in the sample, such as the amount of mRNA degradation of a sample. Samples can be analyzed in their natural state, as collected, and/or in an altered state, for example, following labeling, storage, preservation, extraction, lysis, dilution, concentration, purification, filtration, mixing with one or more reagents, pre-amplification (e.g., to achieve target enrichment by performing limited cycles (e.g., <15) of PCR on sample prior to PCR), removal of amplicon (e.g., treatment with uracil-d-glycosylase (UDG) prior to PCR to eliminate any carry-over contamination by a previously generated amplicon (i.e., the amplicon is digestable with UDG because it is generated with dUTP instead of dTTP)), partitioning, or any combination thereof, among others. Samples can include nasopharyngeal wash, blood, plasma, cell free plasma, buffy coat, saliva, urine, stool, sputum, mucous, wound swab, tissue biopsy, milk, a fluid aspirate, a swab (e.g., a nasopharyngeal swab), and/or tissue, cultured cells, primary cells, bacteria, spores, viruses, small organisms, any of the clinical samples listed above, or the like. A sample, such as a sample containing nucleic acids, can be obtained from any suitable source such as a serum sample, a plasma sample, a cell sample, a tissue sample, an organ sample, a cultured cell line, a biopsy sample, or a fluid sample containing a cell. A sample can be obtained from any suitable organism, such as a plant, animal sample, fungi, bacteria, protist, monera, virus, mitochondria, or chloroplast. In some embodiments the nucleic acid can be obtained from a human.

A nucleic acid can be a nucleotide polymer, and unless otherwise limited, can include known analogs of natural nucleotides that can function in a similar manner (e.g., hybridize) to naturally occurring nucleotides. The nucleic acid molecule can be an RNA molecule, preferably an mRNA molecule. In some embodiments, the nucleic acid molecule can be a DNA molecule, such as a cDNA molecule. In some cases, a nucleic acid sample can derive from biological samples or more specifically from fluids of biological origin, such as blood or serum.

For instance, it can contain viral RNA or other potential parasites from the blood of an individual human; or the RNA can be obtained from purified cells, including flow-sorted cells from dissected tissue, where cells can be labeled with a selectable fluorescent antibody for cell sorting or by the transgenic expression of a marker such as the green fluorescent protein (GFP) or by using other methods known to a person trained in the art. RNA can further be obtained by recent technologies for the isolation of individual cells including, but not limited to, laser capture microdissection or cell aspiration after micro injection. Such cells can be selected based on their morphology or biological features to drive the analysis of specific questions. Moreover, cells can be fractionated to isolate RNA from defined parts of a cell including, but not limited to, different organelles Preferably, RNA can be isolated from the cell's nucleus or the cell's cytoplasm.

Any nucleic acid molecule as applied to perform the invention can be obtained or prepared by any method known to a person skilled in the art including, but not limited to, those described by Sambrook J. and Russuell D. W., Molecular Cloning, A Laboratory Manual, Cold Spring Harbor Laboratory Press, New York, 2001. Other protocols can be found in the public domain. In addition, many providers offer commercial solutions and reagents to isolate RNA or DNA from a sample. For example, RNA can be isolated by purification kits including, but not limited to, TRizolR from Invitrogen, QuickExtract™ FFPE RNA Extraction Kit from Epicentre, or the PicoPure™ RNA Isolation Kit from Molecular Devices for RNA isolation from a single cell. It is within the scope of the invention that RNA can be isolated from organelles or derived from a cell fractionation experiment by any such procedure. RNA purified by such means can be further fractionated according to size or any other features suitable for enrichment including, but not limited to, a hybridization reaction.

A polynucleotide or oligonucleotide can refer to a polymeric form of nucleotides of any length, either deoxyribonucleotides or ribonucleotides, or analogs thereof. Polynucleotides can have any three dimensional structure, and can perform any function, known or unknown. The following are non limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. Polynucleotide sequences, when provided, are listed in the 5'- to 3'-direction, unless stated otherwise.

Nucleic acids can be double- or triple-stranded nucleic acids, as well as single-stranded molecules. In double- or triple-stranded nucleic acids, the nucleic acid strands need not be coextensive, for example, a double-stranded nucleic acid need not be double-stranded along the entire length of both strands.

A nucleic acid can encompass any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications can include base modifications such as 2'-position sugar modifications, 5-position pyrimidine modifications, 8-position purine modifications, modifications at cytosine exocyclic amines, substitutions of 5-bromo-uracil, backbone modifications, and unusual base pairing combinations such as the isobases isocytidine and isoguanidine, and the like.

More particularly, in certain embodiments, nucleic acids can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Nucleic acids can also be linked nucleic acids (LNAs), which are described in U.S. Pat. Nos. 6,794,499, 6,670,461, 6,262,490, and 6,770,748, which are incorporated herein by reference in their entirety for their disclosure of LNAs.

Nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as translation, DNA replication, PCR amplification, reverse transcription, or from a combination of those processes.

A target polynucleotide or target nucleic acid can be a nucleic acid molecule or polynucleotide in a starting population of nucleic acid molecules having a target sequence whose presence, amount, extent of degradation and/or nucleotide sequence, or changes in these, are desired to be determined. In general, a target polynucleotide is a stranded RNA molecule, and can be derived from any source of or process for generating single stranded RNA molecules. A target polynucleotide or target nucleic acid can be a nucleic acid in any sample as described herein.

A target polynucleotide or target nucleic acid can be a non-degraded or degraded RNA molecule. For example, a non-degraded RNA molecule originating from an mRNA molecule can have a 5'-cap and can have a 3'-poly(A) tail. As another example, a degraded RNA molecule originating from an mRNA molecule may not have a 5'-cap but can have a 3'-poly(A) tail. As another example, a degraded RNA molecule originating from an mRNA molecule can have a 5'-cap but may not have a 3'-poly(A) tail. As described above, labeling methods can be selected such that both ends of an intact mRNA molecule are labeled and only one of a degraded mRNA molecule is labeled.

Thus, a target polynucleotide or target nucleic acid can be a non-degraded RNA molecule with one or more labels, such as two labels attached; or a degraded RNA molecule originating from an mRNA molecule that can have one or none of the mRNA specific end structures. In some embodiments, a target polynucleotide or target nucleic acid can be a degraded RNA molecule with no labels.

A target nucleic acid can be in a reference sample. A reference sample can be a sample with a known amount of nucleic acid degradation. For example, a reference sample can comprise nucleic acids, such as mRNA, that can be fully degraded, partially degraded, or substantially not degraded. For example, a reference sample can comprise a total mRNA level wherein about 100%, 99%, 98%, 97%, 96%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1% or 0% of the mRNA is fully degraded. For example, a reference sample can comprise a total mRNA level wherein 0-100%, 0-90%, 0-80%, 0-70%, 0-60%, 0-50%, 0-40%, 0-30%, 0-20%, 0-10%, 10-100%, 10-90%, 10-80%, 10-70%, 10-60%, 10-50%, 10-40%, 10-30%, 10-20%, 20-100%, 20-90%, 20-80%, 20-70%, 20-60%, 20-50%, 20-40%, 20-30%, 30-100%, 30-90%, 30-80%, 30-70%, 30-60%, 30-50%, 30-40%, 40-100%, 40-90%, 40-80%, 40-70%, 40-60%, 40-50%, 50-100%, 50-90%, 50-80%, 50-70%, 50-60%, 60-100%, 60-90%, 60-80%, 60-70%, 70-100%, 70-90%, 70-80%, 80-100%, 80-90%, or 90-100% of the mRNA is fully degraded. For example, a reference sample can comprise a total mRNA level wherein about 100%, 99%, 98%, 97%, 96%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1% or 0% of the mRNA is partially degraded. For example, a reference sample can comprise a total mRNA level wherein 0-100%, 0-90%, 0-80%, 0-70%, 0-60%, 0-50%, 0-40%, 0-30%, 0-20%, 0-10%, 10-100%, 10-90%, 10-80%, 10-70%, 10-60%, 10-50%, 10-40%, 10-30%, 10-20%, 20-100%, 20-90%, 20-80%, 20-70%, 20-60%, 20-50%, 20-40%, 20-30%, 30-100%, 30-90%, 30-80%, 30-70%, 30-60%, 30-50%, 30-40%, 40-100%, 40-90%, 40-80%, 40-70%, 40-60%, 40-50%, 50-100%, 50-90%, 50-80%, 50-70%, 50-60%, 60-100%, 60-90%, 60-80%, 60-70%, 70-100%, 70-90%, 70-80%, 80-100%, 80-90%, or 90-100% of the mRNA is partially degraded. For example, a reference sample can comprise a total mRNA level wherein about 100%, 99%, 98%, 97%, 96%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1% or 0% of the mRNA is substantially not degraded. For example, a reference sample can comprise a total mRNA level wherein 0-100%, 0-90%, 0-80%, 0-70%, 0-60%, 0-50%, 0-40%, 0-30%, 0-20%, 0-10%, 10-100%, 10-90%, 10-80%, 10-70%, 10-60%, 10-50%, 10-40%, 10-30%, 10-20%, 20-100%, 20-90%, 20-80%, 20-70%, 20-60%, 20-50%, 20-40%, 20-30%, 30-100%, 30-90%, 30-80%, 30-70%, 30-60%, 30-50%, 30-40%, 40-100%, 40-90%, 40-80%, 40-70%, 40-60%, 40-50%, 50-100%, 50-90%, 50-80%, 50-70%, 50-60%, 60-100%, 60-90%, 60-80%, 60-70%, 70-100%, 70-90%, 70-80%, 80-100%, 80-90%, or 90-100% of the mRNA is substantially not degraded.

A reference sample can be a sample with a known amount of nucleic acid that is labeled at two intact ends. A reference sample can be a sample with a known amount of nucleic acid that is labeled at one intact end but not another end that is not intact. A reference sample can be a sample with a known amount of nucleic acid that is labeled at one intact end but not another end that is not intact and a known amount of nucleic acid that is labeled at both intact ends. A reference sample can be a sample with a known amount of nucleic acid that is not labeled at either end that is not intact. A reference sample can be a sample with a known amount of nucleic acid that is labeled at one intact end but not another end that is not intact, a known amount of nucleic acid that is labeled at both intact ends, and a known amount of nucleic acid that is not labeled at either end that is not intact. A reference sample can be a sample with a known amount of nucleic acid that is labeled at one intact end but not another end that is not intact and a known amount of nucleic acid that is not labeled at either end that is not intact. A reference sample can be a sample with a known amount of nucleic acid that is labeled at both intact ends and a known amount of nucleic acid that is not labeled at either end that is not intact.

A target sequence can be a nucleic acid sequence on a single strand of nucleic acid. A target sequence can be a portion of a gene, a regulatory sequence, genomic DNA, cDNA, RNA including mRNA, miRNA, and rRNA, or others. A target sequence can be a target sequence from a sample or a secondary target such as a product of an amplification reaction. A target sequence can be embedded in a molecule that includes the nucleotide sequence of a target nucleic acid, such as, for example, the amplification product obtained by amplifying a target nucleic acid or the cDNA produced upon reverse transcription of an RNA target nucleic acid.

A nucleotide probe or probe can be a polynucleotide used for detecting or identifying its corresponding target polynucleotide in a hybridization reaction. Thus, a probe can be hybridizable to one or more target polynucleotides. Probes can be perfectly complementary to one or more target polynucleotides in a sample, or contain one or more nucleotides that are not complemented by a corresponding nucleotide in the one or more target polynucleotides in a sample.

As used herein, complementary can refer to the capacity for precise pairing between two nucleotides. For example, if a nucleotide at a given position of a nucleic acid is capable of hydrogen bonding with a nucleotide of another nucleic acid, then the two nucleic acids can be considered to be complementary to one another at that position. Complementarity between two single-stranded nucleic acid molecules can be partial, in which only some of the nucleotides bind, or it can be complete when total complementarity exists between the single-stranded molecules. The degree of complementarity between nucleic acid strands can have significant effects on the efficiency and strength of hybridization between nucleic acid strands.

Hybridization and annealing can be a reaction in which one or more polynucleotides react to form a complex that is stabilized via hydrogen bonding between the bases of the nucleotide residues. The hydrogen bonding can occur by Watson Crick base pairing, Hoogstein binding, or in any other sequence specific manner. The complex can comprise two strands forming a duplex structure, three or more strands forming a multi stranded complex, a single self hybridizing strand, or any combination of these. A hybridization reaction can constitute a step in a more extensive process, such as the initiation of a PCR or other amplification reactions, or the enzymatic cleavage of a polynucleotide by a ribozyme. A first sequence that can be stabilized via hydrogen bonding with the bases of the nucleotide residues of a second sequence is said to be "hybridizable" to said second sequence. In such a case, the second sequence can also be said to be hybridizable to the first sequence.

A complement of a given sequence can be a sequence that is fully or substantially complementary to and hybridizable to the given sequence. In general, a first sequence that is hybridizable to a second sequence or set of second sequences can be specifically or selectively hybridizable to the second sequence or set of second sequences, such that hybridization to the second sequence or set of second sequences is preferred (for example, thermodynamically more stable under a given set of conditions, such as stringent conditions commonly used in the art) to hybridization with non-target sequences during a hybridization reaction. Hybridizable sequences can share a degree of sequence complementarity over all or a portion of their respective lengths, such as between 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

A hybridized polynucleotide can be a polynucleotide in a complex that is stabilized via hydrogen bonding between the bases of the nucleotide residues. The hydrogen bonding can occur by Watson Crick base pairing, Hoogstein binding, or in any other sequence specific manner. The complex can comprise two strands forming a duplex structure, three or more strands forming a multi stranded complex, a single self hybridizing strand, or any combination of these. The hybridization reaction can constitute a step in a more extensive process, such as the initiation of a PCR reaction, or the enzymatic cleavage of a polynucleotide by a ribozyme. A sequence hybridized with a given sequence can be the complement of the given sequence.

Specific hybridization can be a binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

Complementary can be the capacity for precise pairing between two nucleotides. For example, if a nucleotide at a given position of a nucleic acid is capable of hydrogen bonding with a nucleotide of another nucleic acid, then the two nucleic acids can be considered to be complementary to one another at that position. Complementarity between two single-stranded nucleic acid molecules can be "partial," in which only some of the nucleotides bind, or it can be complete when total complementarity exists between the single-stranded molecules. The degree of complementarity between nucleic acid strands has significant effects on the efficiency and strength of hybridization between nucleic acid strands.

An oligonucleotide can be a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

A primer can be an oligonucleotide that is capable of hybridizing or annealing with a nucleic acid and serving as an initiation site for nucleotide (RNA or DNA) polymerization under appropriate conditions (for example, in the presence of four different nucleoside triphosphates and an agent for polymerization, such as DNA or RNA polymerase or reverse transcriptase) in an appropriate buffer and at a suitable temperature. The appropriate length of a primer can depend on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. A primer length can be the portion of an oligonucleotide or nucleic acid that hybridizes to a complementary target sequence and/or can prime nucleotide synthesis. Short primer molecules generally require cooler temperatures to form sufficiently stable hybrid complexes with the template. A primer need not reflect the exact sequence of the template but must be sufficiently complementary to hybridize with a template. A primer site or primer binding site can be the segment of the target nucleic acid to which a primer hybridizes. A construct with presenting a primer binding site can be a "priming ready construct or amplification ready construct.

A primer can be said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

Expression can be the process by which a polynucleotide is transcribed into mRNA and/or the process by which the transcribed mRNA (also referred to as a transcript) is subsequently being translated into peptides, polypeptides, or proteins. The transcripts and the encoded polypeptides can be a gene product. If the polynucleotide is derived from genomic DNA, expression can include splicing of the mRNA in a eukaryotic cell.

The input nucleic acid can be RNA, for example mRNA, or DNA, for example cDNA. The cDNA can be generated from RNA, e.g., mRNA. The input nucleic acid can be of a specific species, for example, human, rat, mouse, other animals, plants, bacteria, algae, viruses, and the like. The input nucleic acid also can be from a mixture of genomes of different species such as host-pathogen, bacterial populations and the like. The input DNA can be cDNA made from a mixture of genomes of different species. Alternatively, the input nucleic acid can be from a synthetic source. The input nucleic can be cell-free RNA or DNA. The cell-free RNA or DNA can be obtained from, e.g., a serum or plasma sample. The input RNA or DNA can originate from one or more chromosomes. For example, if the input RNA or DNA is from a human, the RNA or DNA can originate from one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The RNA or DNA can originate from plasmid DNA, cosmid DNA, bacterial artificial chromosome (BAC), or yeast artificial chromosome (YAC). The input RNA or DNA can be from more than one individual or organism. The input RNA or DNA can be double stranded or single stranded, or in some cases triple stranded. The input nucleic acid can be a hybrid comprising RNA and DNA on the same strand or in complementary strands. The input RNA or DNA can originate from part of chromatin. The input RNA or DNA can be associated with histones. The methods described herein can be applied to high molecular weight nucleic acids, such as is isolated from tissues or cell culture, for example, as well as highly degraded nucleic acids, such as cell-free nucleic acids from blood and urine and/or nucleic acids extracted from formalin-fixed, paraffin-embedded tissues, for example.

The different samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject can be an animal, including but not limited to, an animal such as a cow, a pig, a mouse, a rat, a chicken, a cat, a dog, etc., and is usually a mammal, such as a human. Samples can also be artificially derived, such as by chemical synthesis. In some embodiments, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which can or may not include target polynucleotides.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods can be preceded by an enzyme digestion step to help eliminate unwanted protein from the sample, e.g., digestion with proteinase K, or other like proteases. See, e.g., U.S. Pat. No. 7,001,724. If desired, RNase inhibitors can be added to the lysis buffer. For certain cell or sample types, it can be desirable to add a protein denaturation/digestion step to the protocol. Purification methods can be directed to isolate DNA, RNA, or both. When both DNA and RNA are isolated together during or subsequent to an extraction procedure, further steps can be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the invention, such as to remove excess or unwanted reagents, reactants, or products.

Amplification

Any of the systems and methods as described in U.S. application Ser. No. 13/072,673 can be used for detection of spaced droplets and labels contained therein. Detection can involve sensing or detecting the droplets themselves and/or contents of the droplets. The detection of droplets themselves can include determining the presence or absence of a droplet (or a plurality of droplets) and/or a characteristic(s) of the droplet, such as its size (e.g., radius or volume), shape, type, and/or aggregation state, among others. The detection of the contents of droplets can include determining the nature of the contents (e.g., whether or not the droplet contains a sample(s)) and/or a characteristic of the contents (e.g., whether or not the contents have undergone a reaction, such as labeling or PCR, the extent of any such reaction, etc.).

The detection of droplets and their contents, if both are detected, can be performed independently or coordinately, in any suitable order. For example, the detection can be performed serially (one droplet at a time), in parallel, in batch, and so forth.

The detection of droplets and their contents can be performed using any technique(s) or mechanism(s) capable of yielding, or being processed to yield, the desired information. These mechanisms can include optical techniques (e.g., absorbance, transmission, reflection, scattering, birefringence, dichroism, fluorescence, phosphorescence, etc.), electrical techniques (e.g., capacitance), and/or acoustic techniques (e.g., ultrasound), among others. The fluorescence techniques, in turn, can include fluorescence intensity, fluorescence polarization (or fluorescence anisotropy) (FP), fluorescence correlation spectroscopy (FCS), fluorescence recovery after photobleaching (FRAP), total internal reflection fluorescence (TIRF), fluorescence resonance energy transfer (FRET), fluorescence lifetime, and/or fluorescence imaging, among others.

A droplet sensor can be used to generate and detect scattered light, and a reaction sensor can be used to generate and detect fluorescence, among other approaches. These systems can be used for a PCR reaction; however, the techniques can apply more generally to any reaction, such as a biochemical reaction, capable of generating, or being modified to generate, a detectable signal.

For example, a sample can be optionally first combined with reagents in a droplet, and the droplet can be thermocycled to induce PCR. It can then be desirable to measure the fluorescence of the droplets to determine which, if any, contained one or more target nucleotide sequences. This generally involves illuminating the droplets with radiation at a wavelength chosen to induce fluorescence, or a change in a characteristic of the fluorescence, from one or more fluorescent probes associated with the amplified PCR target sequence(s). For example, in an exemplary fluorescence intensity assay, if a relatively large intensity of fluorescence is detected, this indicates that PCR amplification of the target nucleotide occurred in the droplet, and thus that the target was present in that portion of the sample. Conversely, if no fluorescence or a relatively small intensity of fluorescence is detected, this indicates that PCR amplification of the target nucleotide did not occur in the droplet, and thus that a target was likely not present in that portion of the sample. In other fluorescence based embodiments, the extent of reaction could be determined from a decrease in fluorescence intensity, instead of a decrease, and/or a change in one or more other fluorescence parameters, including polarization, energy transfer, and/or lifetime, among others.

Any of the systems, apparatuses, and methods as described in U.S. application Ser. No. 13/245,575 can be used for performing droplet-based tests of reactions, such as nucleic acid amplification, that are controlled and/or calibrated using signals detected from droplets.

In some embodiments, the methods described herein can make use of nucleic acid amplification. In some embodiments the target nucleic acids and/or, target nucleic acids labeled with an oligonucleotide, such as a primer, on the 3'- and or 5'-end, such as a 5'-adenylated oligonucleotide that is blocked at the 3'-end as described above, can contain a target sequence for an amplification reaction, such as ddPCR. Amplification of target nucleic acids can be performed by any means known in the art. Amplification can be performed by thermal cycling or isothermally. In exemplary embodiments, amplification can be achieved by the polymerase chain reaction (PCR), such as reverse transcriptase-PCR (RT-PCR).

Some aspects of the invention comprise the amplification of polynucleotide molecules or sequences within the polynucleotide molecules. Amplification generally refers to a method that can result in the formation of one or more copies of a nucleic acid or polynucleotide molecule or in the formation of one or more copies of the complement of a nucleic acid or polynucleotide molecule. Amplifications can be used in the invention, for example, to amplify or analyze a polynucleotide bound to a solid surface or in solution. The amplifications can be performed, for example, after archiving the samples in order to analyze the archived polynucleotide.

In some aspects of the invention, exponential amplification of nucleic acids or polynucleotides is used. These methods often depend on the product catalyzed formation of multiple copies of a nucleic acid or polynucleotide molecule or its complement. The amplification products are sometimes referred to as "amplicons." One such method for the enzymatic amplification of specific single stranded sequences of RNA to cDNA is reverse transcription polymerase chain reaction (RT-PCR).

RT-PCR is a variant of polymerase chain reaction (PCR) well known in the art where a RNA strand is reverse transcribed into its DNA complement (complementary DNA, or cDNA) using the enzyme reverse transcriptase, and the resulting cDNA is amplified using PCR. The in vitro amplification procedure of PCR is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers. Other amplification techniques that can be used in the methods of the provided invention include, e.g., AFLP (amplified fragment length polymorphism) PCR (see e.g.: Vos et al. 1995. AFLP: a new technique for DNA fingerprinting. Nucleic Acids Research 23: 4407-14), allele-specific PCR (see e.g., Saiki R K, Bugawan T L, Horn G T, Mullis K B, Erlich H A (1986). Analysis of enzymatically amplified beta-globin and HLA-DQ alpha DNA with allele-specific oligonucleotide probes Nature 324: 163-166), Alu PCR, assembly PCR (see e.g., Stemmer W P, Crameri A, Ha K D, Brennan T M, Heyneker H L (1995). Single-step assembly of a gene and entire plasmid from large numbers of oligodeoxyribonucleotides Gene 164: 49-53), assymetric PCR (see e.g., Saiki R K supra), colony PCR, helicase dependent PCR (see e.g., Myriam Vincent, Yan Xu and Huimin Kong (2004). Helicase-dependent isothermal DNA amplification EMBO reports 5 (8): 795-800), hot start PCR, inverse PCR (see e.g., Ochman H, Gerber A S, Hartl D L. Genetics. 1988 November; 120(3):621-3), in situ PCR, intersequence-specific PCR or IS SR PCR, digital PCR, linear-after-the-exponential-PCR or Late PCR (see e.g., Pierce K E and Wangh L T (2007). Linear-after-the-exponential polymerase chain reaction and allied technologies Real-time detection strategies for rapid, reliable diagnosis from single cells Methods Mol. Med. 132: 65-85), long PCR, nested PCR, real time PCR (RT-PCR), duplex PCR, multiplex PCR, quantitative PCR, or single cell PCR. Additional examples of PCR techniques that can be used include, but are not limited to, quantitative PCR, quantitative fluorescent PCR (QF-PCR), multiplex fluorescent PCR (MF-PCR), single cell PCR, restriction fragment length polymorphism PCR (PCR-RFLP), PCR-RFLP/RT-PCR-RFLP, in situ polony PCR, in situ rolling circle amplification (RCA), bridge PCR, picotiter PCR, droplet digital PCR, and emulsion PCR.

Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938. Amplification of target nucleic acids can occur on a bead. In other embodiments, amplification does not occur on a bead. Amplification can be by isothermal amplification, e.g., isothermal linear amplification. A hot start PCR can be performed wherein the reaction is heated to 95° C. for two minutes prior to addition of the polymerase or the polymerase can be kept inactive until the first heating step in cycle 1. Hot start PCR can be used to minimize nonspecific amplification. Other strategies for and aspects of amplification are described in U.S. Patent Application Publication No. 2010/0173394 A1, published Jul. 8, 2010, which is incorporated herein by reference.

Another method for amplification involves amplification of a single stranded polynucleotide using a single oligonucleotide primer. The single stranded polynucleotide that is to be amplified contains two non-contiguous sequences that are substantially or completely complementary to one another and, thus, are capable of hybridizing together to form a stem-loop structure. This single stranded polynucleotide already can be part of a polynucleotide analyte or can be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5'-tail comprising a promoter, a second DNA primer, reverse transcriptase, RNase-H, T7 RNA polymerase, NTP's and dNTP's.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTP's, and Q-beta-replicase.

Another method for amplifying nucleic acids is known as 3SR and is similar to NASBA except that the RNase-H activity is present in the reverse transcriptase. Amplification by 3SR is an RNA specific target method whereby RNA is amplified in an isothermal process combining promoter directed RNA polymerase, reverse transcriptase and RNase H with target RNA. See for example Fahy et al. PCR Methods Appl. 1:25-33 (1991).

Another method for amplifying nucleic acids is the Transcription Mediated Amplification (TMA) used by Gen-Probe. The method is similar to NASBA in utilizing two enzymes in a self-sustained sequence replication. See U.S. Pat. No. 5,299,491 herein incorporated by reference.

Another method for amplification of nucleic acids is Strand Displacement Amplification (SDA) (Westin et al 2000, Nature Biotechnology, 18, 199-202; Walker et al 1992, Nucleic Acids Research, 20, 7, 1691-1696), which is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Another method for amplification of nucleic acids is Rolling Circle Amplification (RCA) (Lizardi et al. 1998, Nature Genetics, 19:225-232). RCA can be used to amplify single stranded molecules in the form of circles of nucleic acids. In its simplest form, RCA involves the hybridization of a single primer to a circular nucleic acid. Extension of the primer by a DNA polymerase with strand displacement activity results in the production of multiple copies of the circular nucleic acid concatenated into a single DNA strand.

In some embodiments of the invention, RCA is coupled with ligation. For example, a single oligonucleotide can be used both for ligation and as the circular template for RCA. This type of polynucleotide can be referred to as a "padlock probe" or a "RCA probe." For a padlock probe, both termini of the oligonucleotide contain sequences complementary to a domain within a nucleic acid sequence of interest. The first end of the padlock probe is substantially complementary to a first domain on the nucleic acid sequence of interest, and the second end of the padlock probe is substantially complementary to a second domain, adjacent to the first domain near the first domain. Hybridization of the oligonucleotide to the target nucleic acid results in the formation of a hybridization complex. Ligation of the ends of the padlock probe results in the formation of a modified hybridization complex containing a circular polynucleotide. In some cases, prior to ligation, a polymerase can fill in the gap by extending one end of the padlock probe. The circular polynucleotide thus formed can serve as a template for RCA that, with the addition of a polymerase, results in the formation of an amplified product nucleic acid. The methods of the invention described herein can produce amplified products with defined sequences on both the 5'- and 3'-ends. Such amplified products can be used as padlock probes.

Some aspects of the invention utilize the linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20): E87) can be used. In some cases the methods of the invention can create a "polymerase colony technology," or "polony." referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). The methods of the invention provide new methods for generating and using polonies.

Techniques for amplification of target and reference sequences are known in the art and include the methods described in U.S. Pat. No. 7,048,481. Briefly, the techniques can include methods and compositions that separate samples into small droplets, in some instances with each containing on average less than about 5, 4, 3, 2, or one target nucleic acid molecule (polynucleotide) per droplet, amplifying the nucleic acid sequence in each droplet and detecting the presence of a target nucleic acid sequence. In some cases, the sequence that is amplified is present on a probe to the nucleotide, rather than the nucleotide itself. In some cases, at least 200, 175, 150, 125, 100, 90, 80, 70, 60, 50, 40, 30, 20, 10, or 0 droplets have zero copies of a target nucleic acid. Information about an amplification reaction can be entered or stored into a database.

Primers (e.g., probes) for labeling target nucleic acids and/or for performing amplification reactions can be designed according to known parameters for avoiding secondary structures and self-hybridization. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can be able to hybridize to the target nucleotides described herein. In some embodiments, about 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers are used.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. The primers can have an identical melting temperature. The melting temperature of a primer can be about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. In some embodiments, the melting temperature of the primer is about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C.

The lengths of the primers can be extended or shortened at the 5'-end or the 3'-end to produce primers with desired melting temperatures. One of the primers of a primer pair can be longer than the other primer. The 3'-annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer can be calculated using software programs such as Net Primer. The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5'-half of the primers can be incorporated into the products from each loci of interest; thus the TM can be recalculated based on both the sequences of the 5'-half and the 3'-half of each primer.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about 35, or about cycle 35 to about cycle 40. After the initial cycles of amplification, the 5'-half of the primers can be incorporated into the products from each loci of interest, thus the TM can be recalculated based on both the sequences of the 5'-half and the 3'-half of each primer.

Any DNA polymerase that catalyzes primer extension can be used including but not limited to E. coli DNA polymerase, Klenow fragment of E. coli DNA polymerase 1, T7 DNA polymerase, T4 DNA polymerase, Taq polymerase, Pfu DNA polymerase, Pfx DNA polymerase, Tth DNA polymerase, Vent DNA polymerase, bacteriophage 29, REDTaq™. Genomic DNA polymerase, or sequenase. A thermostable DNA polymerase can be used. The DNA polymerase can have 3'- to 5'-exonuclease activity. The DNA polymerase can possess 5'- to 3'-exonuclease activity. The DNA polymerase can possess both 3'- to 5'-exonuclease activity and 5'- to 3'-exonuclease activity.

Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1 to about 45, about 10 to about 45, about 20 to about 45, about 30 to about 45, about 35 to about 45, about 10 to about 40, about 10 to about 30, about 10 to about 25, about 10 to about 20, about 10 to about 15, about 20 to about 35, about 25 to about 35, about 30 to about 35, or about 35 to about 40.

Thermocycling reactions can be performed on samples contained in droplets. The droplets can remain intact during thermocycling. Droplets can remain intact during thermocycling at densities of greater than about 10,000 droplets/mL, 100,000 droplets/mL, 200,000 droplets/mL, 300,000 droplets/mL, 400,000 droplets/mL, 500,000 droplets/mL, 600,000 droplets/mL, 700,000 droplets/mL, 800,000 droplets/mL, 900,000 droplets/mL or 1,000,000 droplets/mL. In other cases, two or more droplets can coalesce during thermocycling. In other cases, greater than 100 or greater than 1,000 droplets can coalesce during thermocycling. In other cases, less than 20% of the droplets coalesce during thermocycling.

Solution and reagents for performing a PCR reaction can include buffers. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, dTTP, in concentrations of about, more than about, or less than about 50, 100, 200, 300, 400, 500, 600, or 700 µM each. In some cases, a non-canonical nucleotide, e.g., dUTP is added to amplification reaction to a concentration of about, more than about, or less than about 50, 100, 200, 300, 400, 500, 600, or 700, 800, 900, or 1000 µM. In some cases, magnesium chloride ($MgCl_2$) is added to an amplification reaction at a concentration of about, more than about, or less than about 1.0, 2.0, 3.0, 4.0, or 5.0 mM. The concentration of $MgCl_2$ can be about 3.2 mM.

A non-specific blocking agent such as BSA or gelatin from bovine skin can be used, wherein the gelatin or BSA is present in a concentration range of approximately 0.1 to about 0.9% w/v. Other possible blocking agents can include betalactoglobulin, casein, dry milk, or other common blocking agents. In some cases, preferred concentrations of BSA and gelatin are about 0.1% w/v.

In some embodiments, an amplification reaction can also comprise one or more additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). The one or more additives can include, e.g., 2-pyrrolidone, acetamide, N-methylpyrolidone (NMP), B-hydroxyethylpyrrolidone (HEP), propionamide, NN-dimethylacetamide (DMA), N-methylformamide (MMP), NN-dimethylformamide (DMF), formamide, N-methylacetamide (MMA), dimethyl sulfoxide (DMSO), polyethylene glycol, betaine, tetramethylammonium chloride (TMAC), 7-deaza-2'-deoxyguanosine, bovine serum albumin (BSA), T4 gene 32 protein, glycerol, or nonionic detergent (Triton X-100, Tween 20, Nonidet P-40 (NP-40), Tween 40, SDS (e.g., about 0.1% SDS)), salmon sperm DNA, sodium azide, betaine (N,N,N-trimethylglycine; [carboxymethyl]trimethylammonium), formamide, trehalose, dithiothreitol (DTT), betamercaptoethanol (BME), a plant polysaccharide, or an RNase inhibitor.

In some embodiments, an amplification reaction comprises one or more buffers. The one or more buffers can comprise, e.g., TAPS, bicine, Tris, Tricine, TAPSO, HEPES, TES, MOPS, PIPES, cacodylate, SSC, ADA, ACES, cholamine chloride, acetamidoglycine, glycinamide, maleate, phosphate, CABS, piperidine, glycine, citrate, glycylglycine, malate, formate, succinate, acetate, propionate, pyridine, piperazine, histidine, bis-tris, ethanolamine, carbonate, MOPSO, imidazole, BIS-TRIS propane, BES, MOBS, triethanolamine (TEA), HEPPSO, POPSO, hydrazine, Trizma (tris), EPPS, HEPPS, bicine, HEPBS, AMPSO, taurine (AES), borate, CHES, 2-amino-2-methyl-1-propanol (AMP), ammonium hydroxide, methylamine, or MES.

In some cases, a non-ionic Ethylene Oxide/Propylene Oxide block copolymer is added to an amplification reaction in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

Primers for amplification within the aqueous phase of droplets can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µM. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µM. The concentration of primers can be about 0.5 µM. The aqueous phase can comprise one or more probes for fluorescent detection, at a concentration of about, more than about, or less than about 0.05, 0.1, 0.2, 0.3, 0.4, 0.5, 0.6, 0.7, 0.8, 0.9, 1.0, 1.2, 1.4, 1.6, 1.8, or 2.0 µM. The aqueous phase can comprise one or more probes for fluorescent detection, at a concentration of about 0.05 to about 2.0, about 0.1 to about 2.0, about 0.25 to about 2.0, about 0.5 to about 2.0, about 0.05 to about 1, about 0.1 to about 1, or about 0.1 to about 0.5 µM. The concentration of probes for fluorescent detection can be about 0.25 µM. Amenable ranges for target nucleic acid concentrations in PCR are between about 1 pg and about 500 ng.

The primers provided herein can be conjugated to signaling agent. A first primer can be conjugated to a first signaling agent and a second primer can conjugated to a second signaling agent. In some embodiments, a plurality of such first and second primers can be used in the methods and compositions herein, wherein said primers are conjugated to the same signaling agent (e.g., identical fluorophore) or to different signaling agents (e.g., fluorophores of different colors). A first signaling agent can be a fluorescent marker of a first color and a second signaling agent can be a fluorescent marker of a second color.

Primers can be universal primers and can be designed by methods known in the art. In some embodiments, the primer is a random sequence. The universal primer can be selected to ensure that it does not bind the target polynucleotide in an assay, or to other non-target polynucleotides likely to be in a sample (e.g., genomic DNA outside the region occupied by the target polynucleotide).

A label (fluorophore, dye) used on a primer (e.g., a Taqman primer) to detect a target nucleic acid sequence or reference nucleic acid sequence in the methods described herein can be, e.g., 6-carboxyfluorescein (FAM), tetrachlorofluorescin (TET), 4,7,2'-trichloro-7'-phenyl-6-carboxyfluorescein (VIC), HEX, Cy3, Cy 3.5, Cy 5, Cy 5.5, Cy 7, tetramethylrhodamine, ROX, and JOE. The label can be an Alexa Fluor dye, e.g., Alexa Fluor 350, 405, 430, 488, 532, 546, 555, 568, 594, 633, 647, 660, 680, 700, and 750. The label can be Cascade Blue, Marina Blue, Oregon Green 500, Oregon Green 514, Oregon Green 488, Oregon Green 488-X, Pacific Blue, Rhodamine Green, Rhodol Green, Rhodamine Green-X, Rhodamine Red-X, and Texas Red-X. The label can be at the 5'-end of a primer, 3'-end of the primer, at both the 5'- and 3'-end of a primer, or internal to the primer. A unique label can be used to detect each different target nucleic acid end.

A primer, such as a Taqman primer, can comprise a quencher, such as a 3'-quencher. The 3'-quencher can be, for example, TAMARA, DABCYL, BHQ-1, BHQ-2, or BHQ-3. In some cases, a quencher used in the methods provided herein is a black hole quencher (BHQ). In some cases, the quencher is a minor groove binder (MGB). In some cases, the quencher is a fluorescent quencher. In other cases, the quencher is a non-fluorescent quencher (NFQ).

A primer can be about, or at least about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases long. A primer can be about 8 to about 40, about 10 to about 40, about 10 to about 35, about 10 to about 30, about 10 to about 25, about 10 to about 20, about 15 to about 40, about 15 to about 35, about 15 to about 30, about 15 to about 25, about 15 to about 20, about 18 to about 40, about 18 to about 35, about 18 to about 30, about 18 to about 25, or about 18 to 22 bases.

Detection and Enumeration

Detection of labels and/or reporter molecules in droplets can be used to assess the degradation of target nucleotides in a sample. In some embodiments, detection of labels and/or reporter molecules in droplets can be used to quantify the degradation of target nucleotides in a sample. In some embodiments detection of labels and/or reporter molecules in droplets from a reference sample, such as those described herein, can be used to quantify the degradation of target nucleotides in a sample.

Detection can be done by any suitable method known in the art, such as by spectroscopic detection of fluorescent labels or by testing the presence of amplification from one or more partitioned mRNA molecules, such as it is performed by techniques related to digital PCR (dPCR), described in further detail elsewhere in this application.

Fluorescence detection can be achieved using a variety of detector devices equipped with a module to generate excitation light that can be absorbed by a fluorescer, as well as a module to detect light emitted by the fluorescer. In some cases, samples (such as droplets) can be detected in bulk. For example, samples can be allocated in plastic tubes that are placed in a detector that measures bulk fluorescence from plastic tubes. In some cases, one or more samples (such as droplets) can be partitioned into one or more wells of a plate, such as a 96-well or 384-well plate, and fluorescence of individual wells can be detected using a fluorescence plate reader.

In some cases, the detector further comprises handling capabilities for droplet samples, with individual droplets entering the detector, undergoing detection, and then exiting the detector. For example, a flow cytometry device can be adapted for use in detecting fluorescence from droplet samples. In some cases, a microfluidic device equipped with pumps to control droplet movement is used to detect fluorescence from droplets in single file. In some cases, droplets are arrayed on a two-dimensional surface and a detector moves relative to the surface, detecting fluorescence at each position containing a single droplet.

Following acquisition of detection data, such as fluorescence detection data, a computer can be used to store and process the data. Computer-executable logic can be employed to perform such functions as subtraction of background, such as background fluorescence, assignment of target and/or reference sequences, and quantification of the data. A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods of the present invention.

Detection can be used for enumerating a number of spatially isolated partitions comprising a label. Detection can be used for enumerating a number of spatially isolated partitions comprising only one label. Detection can be used for enumerating a number of spatially isolated partitions comprising two labels. Detection can be used for enumerating a number of spatially isolated partitions comprising no label.

In some cases, detection can be used for enumerating the number of spatially isolated partitions comprising two labels in a plurality of sample partitions and for enumerating the number of spatially isolated partitions comprising only one label in the plurality of sample partitions. In some cases, the amount of nucleic acid degradation can be determined by comparing the number of spatially isolated partitions comprising two labels in a plurality of sample partitions to the number of spatially isolated partitions comprising only one label in the plurality of sample partitions. The total number of partitions in a plurality of partitions can be about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, 200,000, 500,000, 750,000, or 1,000,000. The total number of partitions can be about 500 to about 1,000,000, about 500 to about 500,000, about 500 to about 250,000, about 500 to about 100,000, about 1000 to about 1,000,000, about 1000 to about 500,000, about 1000 to about 250,000, about 1000 to about 100,000, about 10,000 to about 1,000,000, about 10,000 to about 100,000, or about 10,000 to about 50,000.

In some cases, the amount of nucleic acid degradation can be determined by comparing the number of spatially isolated partitions comprising two labels in a plurality of sample partitions and the number of spatially isolated partitions comprising only one label in the plurality of sample partitions to the number of spatially isolated partitions in the plurality of sample partitions comprising no label. In some cases, the amount of nucleic acid degradation can be determined by comparing the number of spatially isolated partitions comprising two labels in a plurality of sample partitions to the number of spatially isolated partitions in the plurality of sample partitions comprising no label. In some cases, the amount of nucleic acid degradation can be determined by comparing the number of spatially isolated partitions comprising only one label in the plurality of sample partitions to the number of spatially isolated partitions in the plurality of sample partitions comprising no label.

In another embodiment, the amount of nucleic acid degradation can be determined by comparing the number of spatially isolated partitions comprising two labels in a plurality of sample partitions, the number of spatially isolated partitions comprising only one label in the plurality of sample partitions, and the number of spatially isolated partitions comprising no label in the plurality of sample partitions to the total amount of the nucleic acid in the sample. In some cases, the amount of nucleic acid degradation can be determined by comparing the number of spatially isolated partitions comprising two labels in a plurality of sample partitions and the number of spatially isolated partitions comprising no label to the total amount of the nucleic acid in the sample.

In some cases, the amount of nucleic acid degradation can be determined by comparing the number of spatially isolated partitions comprising only one label in a plurality of sample partitions and the number of spatially isolated partitions comprising no label to the total amount of the nucleic acid in the sample. In some cases, the amount of nucleic acid degradation can be determined by comparing the number of spatially isolated partitions comprising two labels in a plurality of sample partitions to the total amount of the nucleic acid in the sample. In some cases, the amount of nucleic acid degradation can be determined by comparing the number of spatially isolated partitions comprising one label in a plurality of sample partitions to the total amount of the nucleic acid in the sample. In some cases, the amount of nucleic acid degradation can be determined by comparing the number of spatially isolated partitions comprising no label in a plurality of sample partitions to the total amount of the nucleic acid in the sample.

Determining the amount of degradation for the nucleic acid can be accomplished using an algorithm.

A digital readout assay, e.g., digital PCR, can be used to count targets (e.g., target nucleic acids) by partitioning the targets in a sample and identifying partitions containing the target. A digital readout is an all or nothing analysis in that it specifies whether a given partition contains the target of interest, but does not necessarily indicate how many copies of the target are in the partition. For example, a single polynucleotide containing two targets can be in a partition, but under normal analysis conditions, the partition will only be considered to contain one target. If the targets on the same polynucleotide are separated by a large number of base pairs, some of the target nucleic acid sequences can be separated by fragmentation during purification of a sample—some linked target nucleic acid sequences may not remain physically linked after sample preparation. Digital PCR is described generally, e.g., at Vogelstein and Kinzler (1999) *PNAS* 96:9236-9241. Digital PCR can be performed on portions of a sample to determine the presence/absence, concentration, and/or copy number of a nucleic acid target in the sample, based on how many of the sample portions support amplification of the target. Digital PCR can (or may not) be performed as endpoint PCR. Digital PCR can (or may not) be performed as real-time PCR for each of the partitions. Droplet digital PCR can be used to measure restriction enzyme efficiency and specificity.

PCR theoretically results in an exponential amplification of a nucleic acid sequence (analyte) from a sample. By measuring the number of amplification cycles required to achieve a threshold level of amplification (as in real-time PCR), one can theoretically calculate the starting concentration of nucleic acid. In practice, however, there are many factors that make the PCR process non-exponential, such as varying amplification efficiencies, low copy numbers of starting nucleic acid, and competition with background contaminant nucleic acid. Digital PCR is generally insensitive to these factors, since it does not rely on the assumption that the PCR process is exponential. In digital PCR, individual nucleic acid molecules are separated from the initial sample into partitions, then amplified to detectable levels. Each partition then provides digital information on the presence or absence of each individual target nucleic acid molecule, such as the labeled nucleotides described herein, within each partition. When enough partitions are measured using this technique, the digital information can be consolidated to make a statistically relevant measure of starting concentration for the nucleic acid target (analyte) in the sample.

The concept of digital PCR can be extended to other types of analytes, besides nucleic acids. In particular, a signal amplification reaction can be utilized to permit detection of a single copy of a molecule of the analyte in individual droplets, to permit data analysis of droplet signals for other analytes (e.g., using an algorithm based on Poisson statistics). Exemplary signal amplification reactions that permit detection of single copies of other types of analytes in droplets include enzyme reactions.

In general, Reverse Transcriptase-dPCR can involve spatially isolating (or partitioning) individual polynucleotides from a sample and carrying out a RT-polymerase chain reaction on each partition. The partition can be, e.g., a well (e.g., wells of a microwell plate), capillary, dispersed phase of an emulsion, a chamber (e.g., a chamber in an array of miniaturized chambers), a droplet, or a nucleic acid binding surface. The sample can be distributed so that each partition has about 0, 1, 2, 3, 4, or 5 target polynucleotides. Each partition can have, on average, less than 5, 4, 3, 2, or 1 copies of a target nucleic acid per partition (e.g., droplet). In some cases, at least 0, 1, 2, 3, 4, 5, 6, 7, 8, 9, 10, 20, 30, 40, 50, 60, 70, 80, 90, 100, 125, 150, 175, or 200 partitions (e.g., droplets) have zero copies of a target nucleic acid. After RT-PCR, and in some embodiments PCR amplification, the number of partitions with or without a PCR product can be enumerated. The total number of partitions can be about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, 200,000, 500,000, 750,000, or 1,000,000. The total number of partitions can be about 500 to about 1,000,000, about 500 to about 500,000, about 500 to about 250,000, about 500 to about 100,000, about 1000 to about 1,000,000, about 1000 to about 500,000, about 1000 to about 250,000, about 1000 to about 100,000, about 10,000 to about 1,000,000, about 10,000 to about 100,000, or about 10,000 to about 50,000.

In some cases, the RT-dPCR is RT droplet digital PCR. In some embodiments of a RT droplet digital PCR experiment, less than about 0.00001, 0.00005, 0.00010, 0.00050, 0.001, 0.005, 0.01, 0.05, 0.1, 0.5, 1, 2, 2.5, 3, 3.5, 4, 4.5, 5, 6, 7, 8, 9, or 10 copies of target polynucleotide can detected. In some cases, less than about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide are detected. In some cases, the droplets described herein are generated at a rate of greater than 1, 2, 3, 4, 5, 10, 50, 100, 200, 300, 400, 500, 600, 700, 800, 900, or 1000 droplets/second.

Droplet digital PCR (ddPCR) can offer a practical solution for validating copy number variations identified by next generation sequencers and microarrays. Methods using ddPCR can empower one person to screen many samples, e.g., hundreds of samples, for nucleic acid degradation in a single work shift. In some cases, a ddPCR workflow is provided that involves using one or more restriction enzymes to separate tandem copies of a target nucleic acid sequence prior to assembling a duplex TaqMan® assay that includes reagents to detect both a target nucleic acid, such as a labeled target nucleic acid, and a reference nucleic acid, such as a nucleic acid with a known amount of label, for example a nucleic acid with an oligonucleotide or primer attached the intact 5' end. When ddPCR is used, the reaction mixture can then be partitioned into about, less than about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, 200,000, 500,000, 750,000, 1,000,000, 2,000,000, 3,000,000, 4,000,000, 5,000,000, 6,000,000, 7,000,000, 8,000,000, 9,000,000, or 10,000,000 nanoliter droplets that can be thermo-cycled to end-point before being analyzed. In some cases, the droplets are greater than one nanoliter; in other cases, the droplets are less than one nanoliter (e.g., picoliter). The number of droplets per reaction can be about 1000 to about 1,000,000, about 1000 to about 750,000, about 1000 to about 500,000, about 1000 to about 250,000, about 1000 to about 100,000, about 1000 to about 50,000, about 1000 to about 30,000, about 1000 to about 10,000, about 10,000 to about 1,000,000, about 10,000 to about 750,000, about 10,000 to about 500,000, about 10,000 to about 250,000, about 10,000 to about 100,000, about 10,000 to about 50,000, or about 10,000 to about 30,000. The number of droplets per reaction can be about 20,000 to about 1,000,000, about 20,000 to about 750,000, about 20,000 to about 500,000, about 20,000 to about 250,000, about 20,000 to about 200,000, about 20,000 to about 50,000, about 50,000 to about 100,000, about 50,000 to about 200,000; or about 50,000 to about 300,000. The droplet volumes can have any suitable size. In some embodiments, the volumes can have a diameter or characteristic cross-sectional dimension of about 10 to 1000 micrometers. Each volume can be partitioned to contain any suitable average concentration of nucleic acid.

An analysis can occur in a two-color reader. The fraction of positive-counted droplets can enable the absolute concentrations for the target and reference nucleic acid sequences (e.g., nucleic acids labeled according the methods provided herein) to be measured. This information can be used to determine a relative amount of mRNA degradation. This low-cost method can reliably generate nucleic acid degradation measurements with 95% confidence intervals.

The nucleic acid that is partitioned can have any suitable characteristics. The nucleic acid can include genetic material of the subject (e.g., the subject's genomic DNA and/or RNA), messenger RNA of the subject, and/or cDNA derived from RNA of the subject, among others. The nucleic acid can have any suitable average length.

An integrated, rapid, flow-through thermal cycler device can be used in the methods described herein. See, e.g., International Application No. PCT/US2009/005317, filed Sep. 23, 2009. In such an integrated device, a capillary is wound around a cylinder that maintains 2, 3, or 4 temperature zones. As droplets flow through the capillary, they are subjected to different temperature zones to achieve thermal cycling. The small volume of each droplet results in an extremely fast temperature transition as the droplet enters each temperature zone.

A digital PCR device (e.g., droplet digital PCR device) for use with the methods, compositions, and kits described herein can detect multiple signals (see e.g. U.S. Provisional Patent Application No. 61/454,373, filed Mar. 18, 2011, herein incorporated by reference in its entirety).

Droplet digital PCR can involve the generation of thousands of discrete, robust microdroplet reactors per second. ddPCR can involve standard thermal cycling with installed-base instruments, which can make digital data accessible immediately to researchers. Rapid interrogation of each droplet can yield counts of target molecules present in the initial sample.

Figure 16:
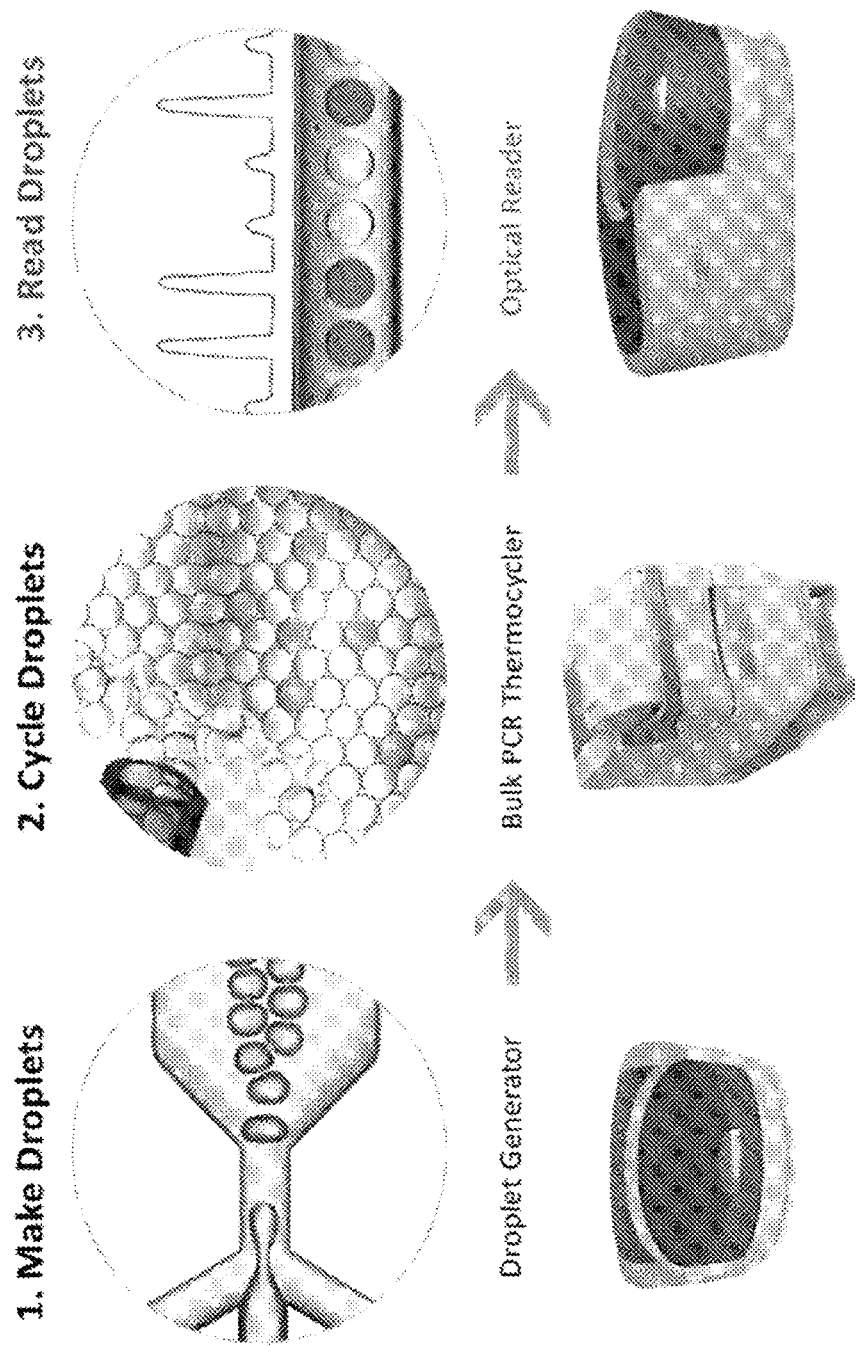
FIG. 16 depicts a typical work flow diagram of digital PCR analysis.

FIG. 16 illustrates an example of a general workflow for a ddPCR experiment. As shown in FIG. 16, the process can start by partitioning a sample, such as a labeled nucleic acid sample, into multiple partitions, such as droplets, followed by thermal cycling the sample in a thermal cycler. The fluorescence of the droplets can then be detected using a reader, such as an optical reader.

The length of storage of nucleic acids can impact the accuracy of future measurements. Extended storage can cause reduction in the mRNA estimated. For example, extended storage can result in nucleic acid degradation. The length of storage of a nucleic acid sample can be about, or less than about, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 hrs. The length of storage of a nucleic acid sample can be about, or less than about, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days. The length of storage of a nucleic acid sample can be about, or less than about, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years.

The storage temperature of a nucleic acid sample, (e.g., a digested nucleic acid sample) can be about, or less than about 4, 0, −10, −20, −30, −40, −50, −60, −70, −80, −90, −100, −110, −120, −130, −140, −150, −160, −170, −180, −190, or −200° C.

This application incorporates by reference in their entirety for all purposes the following materials: U.S. Pat. No. 7,041,481, issued May 9, 2006; U.S. Patent Application Publication No. 2010/0173394 A1, published Jul. 8, 2010; and Joseph R. Lakowicz, Principles of Fluorescence Spectroscopy (2nd Ed. 1999).

Kits

Provided herein are kits for carrying out the methods of the provided invention. The kits can comprise one or more restriction enzymes, devices, buffers, reagents, and instructions for use. A kit can comprise a restriction enzyme, a buffer, a salt, and instructions for use. A kit can comprise one or more primers and one or more probes. In some cases, a kit comprises one or more labels restriction enzyme, four primers, and two probes. In another embodiment, a kit comprises one or more labels restriction enzyme, at least four primers, and one or more labels probe. In another embodiment, a kit comprises one or more labels restriction enzyme at least four primers, and at least two probes.

Any of the compositions described herein can be comprised in a kit. The kit can contain enzymes and/or reagents useful for ligation, cleavage and or amplification. The kit can contain a DNA-polymerase. The kit can contain reagents for amplification, for example reagents useful for single primer isothermal amplification methods. The kit can contain reagents for attaching labels to nucleic acids. The can further contain reporter molecules attached to chemically active reagents. In some embodiments, the kit contains reporter moieties linked to oligonucleotides. The oligonucleotides can comprise sequences that are identical or complementary to target polynucleotides of the invention. The oligonucleotides can comprise primer sequences for performing amplification of the target nucleotides. The kit can further optionally contain reagents for sequencing, for example, reagents useful for next-generation massively parallel sequencing methods.

The containers of the kits can generally include one or more labels vial, test tube, flask, bottle, syringe or other containers, into which a component can be placed, and preferably, suitably aliquoted. Where there is more than one component in the kit, the kit also can generally contain a second, third or other additional container into which the additional components can be separately placed. However, various combinations of components can be comprised in a container.

When the components of the kit are provided in one or more liquid solutions, the liquid solution can be an aqueous solution. However, the components of the kit can be provided as dried powder(s). When reagents and/or components are provided as a dry powder, the powder can be reconstituted by the addition of a suitable solvent.

A kit can include instructions for employing the kit components as well the use of any other reagent not included in the kit. Instructions can include variations that can be implemented. In one aspect, the invention provides kits containing any one or more of the elements disclosed in the above methods and compositions. In some embodiments, a kit comprises a composition of the invention, in one or more containers.

In some embodiments, the invention provides kits comprising agents, labeling molecules, enzymes, and/or oligonucleotides described herein. In some embodiments, a kit comprises one or more of: a first labeling molecule, an enzyme that is capable of removing a 5'-end cap from an RNA, an amine reactive label, an RNA ligase, a first oligonucleotide comprising a primer binding sequence blocked at the 3'-end, an oligonucleotide tag comprising a primer binding sequence one or more labels agent that is capable of facilitating labeling a ribose diol group at an end of a nucleic acid. A kit can comprise one or more labels agent that is capable of facilitating labeling a ribose diol group at an end of a nucleic acid, a first labeling molecule, an enzyme that is capable of removing a 5'-end cap from an RNA, and an amine reactive label. A kit can comprise an enzyme that is capable of removing a 5'-end cap from an RNA, an RNA ligase, a first oligonucleotide, wherein the oligonucleotide is blocked at the 3'-end and wherein the first oligonucleotide comprises a primer binding sequence, and an amine reactive label. A kit can comprise one or more labels agent that is capable of facilitating labeling a ribose diol group at an end of a nucleic acid, a first labeling molecule, an enzyme that is capable of removing a 5'-end cap from an RNA, an RNA ligase, and an oligonucleotide tag, wherein the oligonucleotide tag comprises a primer binding sequence. A kit can comprise an enzyme that is capable of removing a 5'-end cap from an RNA, an RNA ligase, a first oligonucleotide, wherein the first oligonucleotide is blocked at the 3'-end and wherein the first oligonucleotide comprises a first primer binding sequence, and an oligonucleotide tag, wherein the oligonucleotide tag comprises a second primer binding sequence. The first labeling molecule or an amine reactive label can be any of those described herein and can comprise a fluorophore. The RNA ligase can be T4 RNA ligase. Any of the kits described herein can further comprise an RNA dependent polymerase. Any of the kits described herein can further comprise a second labeling molecule. Any of the kits described herein can further comprise one or more buffers suitable for one or more of the elements contained in the kit. Elements of the kit can further be provided, without limitation, in any suitable amounts and/or using any of the combinations (such as in the same kit or same container) described above or any other suitable combination known in the art. The kits can further comprise additional agents, such as those described above, for use according to the methods of the invention. The kit elements can be provided in any suitable container, including but not limited to test tubes, vials, flasks, bottles, ampules, syringes, or the like. The agents can be provided in a form that can be directly used in the methods of the invention, or in a form that requires preparation prior to use, such as in the reconstitution of lyophilized agents. Agents can be provided in aliquots for single-use or as stocks from which multiple uses, such as in a number of reaction, can be obtained.

Conventional techniques can be used in the methods described herein. Such conventional techniques can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000), Lehninger, (2004) Principles of Biochemistry $4^{th}$ Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

EXAMPLES

Non-Selective End Labeling

A nucleic acid sample containing mRNA after storage is contacted with sodium periodate to nonselectively oxidize intact 5'- and 3'-ends forming aldehydes from the diol moieties. A fluorescent label with a hydrazine linkage is then added to the nucleic acid sample and the aldehydes are labeled. The nucleic acid sample is partitioned into a plurality of emulsion droplets. The fluorescence intensity of the droplets is measured. The number of droplets containing high fluorescence, medium fluorescence and substantially no fluorescence is determined. An algorithm is used to determine the amount of degradation of mRNA in the sample.

Selective End Labeling

A nucleic acid sample containing mRNA after storage is contacted with TAP to selectively remove the 5'-cap structure leaving a 5'-monophosphate group. The sample is divided into subsample 1 and subsample 2. Subsample 1 is contacted with sodium periodate to selectively oxidize intact 3'-ends forming aldehydes from the diol moieties. A fluorescent label with a hydrazine linkage is then added to the nucleic acid sample and the aldehydes formed selectively at the intact 3'-ends are labeled. Subsample 2 is contacted with sodium periodate to selectively oxidize intact 3'-ends forming aldehydes from the diol moieties. A 5'-adenylated oligonucleotide blocked at the 3'-end is ligated to a 3' end of an mRNA molecule. Subsample 2 is then contacted with a label containing an amine modification or with a T4 RNA Ligase and an oligonucleotide to label the 5'-end selectively. Each of the subsamples are then partitioned into a plurality of emulsion droplets. The fluorescence intensity of the droplets is measured. The number of droplets containing high fluorescence, medium fluorescence and substantially no fluorescence is determined for each subsample. An algorithm is used to determine the amount of degradation of mRNA in the sample. Linkage between the two assays is evaluated to determine the amount of degradation of mRNA in the sample.

What is claimed is:

1. A method of detecting degradation of mRNA, the method comprising:
   (a) contacting a sample comprising mRNA with at least one agent to covalently attach an oligonucleotide label to a first end of RNA molecules having a first end structure and to covalently attach an oligonucleotide label to a second end of mRNA molecules having a second end structure;
   (b) separating the sample into a plurality of spatially isolated partitions;
   (c) enumerating a first number of spatially isolated partitions comprising an oligonucleotide label covalently attached to the first end of an mRNA molecule and an oligonucleotide label covalently attached to the second end of an mRNA molecule, and a second number of spatially isolated partitions comprising an oligonucleotide label covalently attached only to the first end or only to the second end of an mRNA molecule; and
   (d) determining an amount of degradation for the mRNA based on the enumerating, wherein the step of determining comprises comparing the first number and the second number to one another.

2. The method of claim 1, wherein the separating is randomized.

3. The method of claim 1, wherein covalent attachment of an oligonucleotide label to the first end of mRNA molecules and covalent attachment of an oligonucleotide label to the second end of mRNA molecules is not sequence specific.

4. The method of claim 1, wherein the second end of mRNA molecules having a 3'-phosphate group or a 2'-3'-linked phosphate group are not substantially labeled with an oligonucleotide label by the step of contacting.

5. The method of claim 1, wherein the first end of mRNA molecules having a 5'-phosphate group and the second end of mRNA molecules having a 3'-hydroxyl group are substantially labeled with an oligonucleotide label by the step of contacting.

6. The method of claim 1, wherein the at least one agent comprises a ligase.

7. The method of claim 1, wherein the second end of mRNA molecules including a ribose diol group are substantially labeled by the step of contacting.

8. The method of claim 1, wherein mRNA molecules comprising an intact 5'-end cap are substantially labeled by the step of contacting.

9. The method of claim 1, wherein the spatially isolated partitions are droplets within an emulsion.

10. The method of claim 1, wherein the determining is accomplished using an algorithm.

11. The method of claim 8, wherein the at least one agent comprises a decapping enzyme.

12. The method of claim 6, wherein the at least one agent comprises a T4 RNA ligase.

13. The method of claim 1, wherein the oligonucleotide covalently attached to the second end comprises, before attachment, a 5'-adenylated end, a blocked 3'-end, and a target sequence for an amplification reaction.

14. The method of claim 13, wherein the amplification reaction is ddPCR.

15. The method of claim 1, further comprising enumerating a number of spatially isolated partitions comprising mRNA from a reference sample.

16. The method of claim 15, the sample being a test sample, wherein the steps of contacting, separating, and enumerating are also performed with a reference sample, and wherein the step of determining an amount of degradation for the mRNA based on the enumerating comprises comparing the number for the test sample and the number for the reference sample with one another.

17. The method of claim 1, further comprising determining a concentration of mRNA in the sample.

18. The method of claim 1, wherein the oligonucleotide covalently attached to the first end has a different sequence from the oligonucleotide covalently attached to the second end.

* * * * *